United States Patent

Takada

(10) Patent No.: US 8,415,032 B2
(45) Date of Patent: Apr. 9, 2013

(54) MATERIAL FOR ORGANIC ELECTROLUMINESCENCE DEVICE AND ORGANIC ELECTROLUMINESCENCE DEVICE

(75) Inventor: Saki Takada, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 13/393,194

(22) PCT Filed: Aug. 17, 2010

(86) PCT No.: PCT/JP2010/064127
§ 371 (c)(1),
(2), (4) Date: Feb. 28, 2012

(87) PCT Pub. No.: WO2011/024733
PCT Pub. Date: Mar. 3, 2011

(65) Prior Publication Data
US 2012/0153273 A1    Jun. 21, 2012

(30) Foreign Application Priority Data
Aug. 31, 2009 (JP) .................... 2009-201146

(51) Int. Cl.
*H01L 51/54* (2006.01)
*C09K 11/06* (2006.01)

(52) U.S. Cl.
USPC ...... 428/690; 428/917; 252/301.16; 548/103; 313/504; 313/506; 257/40; 257/102; 257/E51.044

(58) Field of Classification Search ............ None
See application file for complete search history.

(56) References Cited

U.S. PATENT DOCUMENTS

| | | | |
|---|---|---|---|
| 7,915,415 B2 | 3/2011 | Knowles et al. | |
| 2003/0189216 A1 | 10/2003 | Kamatani et al. | |
| 2005/0037236 A1 | 2/2005 | Kamatani et al. | |
| 2007/0190359 A1 | 8/2007 | Knowles et al. | |
| 2008/0160345 A1 | 7/2008 | Inoue et al. | |
| 2008/0297033 A1 | 12/2008 | Knowles et al. | |
| 2010/0141125 A1 | 6/2010 | Otsu et al. | |
| 2010/0141126 A1 | 6/2010 | Otsu et al. | |
| 2011/0073849 A1 | 3/2011 | Knowles et al. | |

FOREIGN PATENT DOCUMENTS

| | | |
|---|---|---|
| JP | 2003-068467 A | 3/2003 |
| JP | 2004-131463 A | 4/2004 |
| JP | 2007-091718 A | 4/2007 |
| JP | 2008-010651 A | 1/2008 |
| JP | 2008-179607 A | 8/2008 |
| JP | 2008-311607 A | 12/2008 |
| JP | 2009-526071 A | 7/2009 |
| WO | 03-077609 A1 | 9/2003 |
| WO | 2008-140114 A1 | 11/2008 |
| WO | 2008-140115 A1 | 11/2008 |
| WO | 2008-143059 A1 | 11/2008 |
| WO | 2010-032663 A1 | 3/2010 |
| WO | 2010-064621 A1 | 6/2010 |

OTHER PUBLICATIONS

International Search Report (PCT/ISA/210) issued Sep. 21, 2010 in PCT/JP2010/064127.
Written Opinion (PCT/ISA/237) issued Sep. 21, 2010 in PCT/JP2010/064127.
Japanese Office Action issued Nov. 25, 2009, in Japanese Patent Application No. 2009-201146.

*Primary Examiner* — Michael H Wilson
(74) *Attorney, Agent, or Firm* — Morgan, Lewis & Bockius LLP

(57) ABSTRACT

A material for an organic electroluminescence device including a phosphorescent metal complex containing a monoanionic bidentate ligand represented by the following formula (A1-1) or formula (A3-1) as defined in the specification and a non-radiative metal having an atomic weight of 40 or more, an organic electroluminescence device including the material for an organic electroluminescence device, and a light emitting unit, a display unit and an illumination unit each including the organic electroluminescence device are provided.

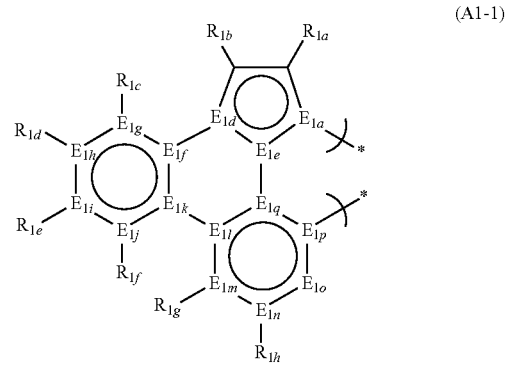

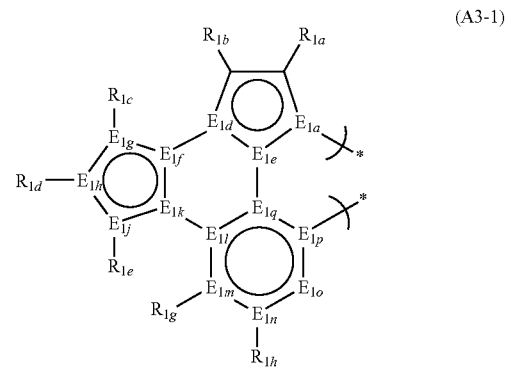

8 Claims, 2 Drawing Sheets

F CONTENT AND EXTERNAL QUANTUM EFFICIENCY

F CONTENT AND SUBLIMATION APTITUDE

MATERIAL FOR ORGANIC ELECTROLUMINESCENCE DEVICE AND ORGANIC ELECTROLUMINESCENCE DEVICE

TECHNICAL FIELD

The present invention relates to a material for organic electroluminescence device and an organic electroluminescence device.

BACKGROUND ART

In recent years, in view of the fact that light emission with a high brightness is obtainable through low-voltage driving, an organic electroluminescence device (hereinafter also referred to as "device" or "organic EL device") has been actively researched and developed. In general, the organic electroluminescence device is constituted of an organic layer including a light emitting layer and a pair of electrodes interposing this light emitting layer therebetween, and energy of an exciton generated through recombination of an electron injected from a cathode and a hole injected from an anode is utilized for the light emission.

In recent years, an improvement of efficiency of the device is being advanced by using a phosphorescent material. For example, an organic electroluminescence device having enhanced luminous efficiency and device durability is researched by using an iridium complex, a platinum complex or the like as the phosphorescent material.

Also, a dope-type device using a light emitting layer having a light emitting material doped in a host material is widely employed.

US-A-2008/297033 and JP-A-2008-311607 disclose iridium complexes containing a condensed ring azole ligand, having high durability and capable of achieving blue light emission.

SUMMARY OF INVENTION

However, organic EL devices using an iridium complex disclosed in US-A-2008/297033 and JP-A-2008-311607 involve such a problem that the luminous efficiency is low. Also, there is involved such a problem that light emission obtained from such an organic EL device is long in a wavelength so that the light emission does not become purely blue. Though it is possible to improve the luminous efficiency by introducing an alkyl substituent into a specified position of the iridium complex, the durability is lowered, and therefore, it is demanded that the luminous efficiency and the durability are compatible with each other.

Also, in general, a material used for an organic EL device is required to have a very high purity, and therefore, there are often obtained purified products by means of zone melting or sublimation purification. However, according to investigations made by the present inventors, since the phosphorescent metal complexes disclosed in US-A-2008/297033 and JP-A-2008-311607 have such a characteristic feature that they melt at the time of sublimation purification, the surface area is small, and a time required at the time of sublimation purification is long. Thus, an improvement is required from the viewpoint of productivity.

An object of the invention is to provide a material for organic EL device which is able to be used for an organic EL device, displays excellent luminous efficiency and durability, has light emitting characteristics with an excellent hue and is excellent from the viewpoint of productivity. Also, another object of the invention is to provide an organic electroluminescence device using this material for organic EL device.

In order to solve the foregoing problems, the present inventors made extensive and intensive investigations. As a result, it has been found that it is possible to make both durability and luminous efficiency compatible with each other by using a complex obtained by introducing a certain number or more of fluorine atoms as a substituent into a ligand having a condensed ring azole structure. Also, it has been clarified that the foregoing complex is suppressed in melting, is short in a time required for sublimation purification and is able to provide a high-performance material within a short period of time. That is, the invention can be achieved by the following means.

[1] A material for an organic electroluminescence device, comprising:

a phosphorescent metal complex containing a monoanionic bidentate ligand represented by the following formula (A1-1) or formula (A3-1), and a non-radiative metal having an atomic weight of 40 or more:

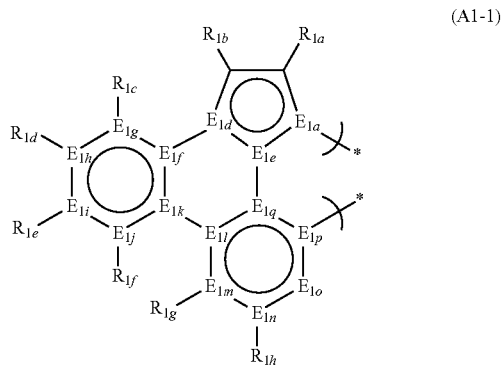

(A1-1)

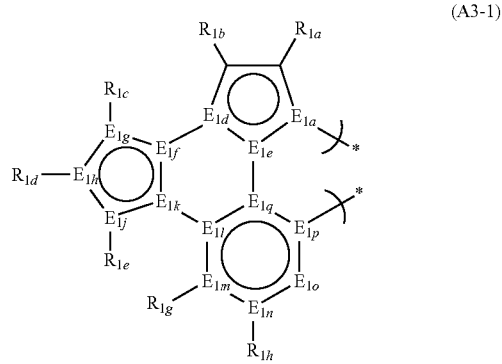

(A3-1)

wherein
each of $E_{1a}$, $E_{1d}$ to $E_{1n}$, $E_{1p}$, and $E_{1q}$ independently represents a carbon atom or a hetero atom;
at least one of $E_{1a}$, $E_{1a}$ and $E_{1e}$ represents a nitrogen atom;
$E_{1o}$ represents CH or a nitrogen atom;
each of $R_{1a}$ to $R_{1h}$ independently represents a hydrogen atom, a fluorine atom, a hydrocarbon substituent or a fluorine-substituted hydrocarbon substituent consisting only of a carbon atom, a hydrogen atom and a fluorine atom; and
$R_{1a}$ to $R_{1h}$ may be bonded to each other to form a ring, provided that a content of a fluorine atom in the phosphorescent metal complex is 7% by mass or more; and that each of structures represented by the formulae (A1-1) and (A3-1) has a 18 π-electron structure in total.

[2] The material for an organic electroluminescence device as described in [1] above, wherein the monoanionic bidentate ligand is a monoanionic bidentate ligand represented by the following formula (A1-3) or (A3-3):

(A1-3)

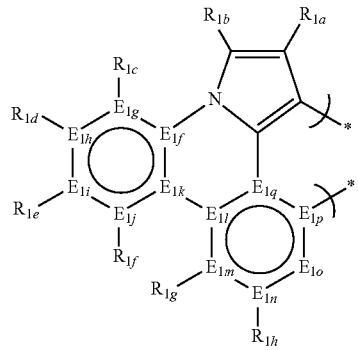

(A3-3)

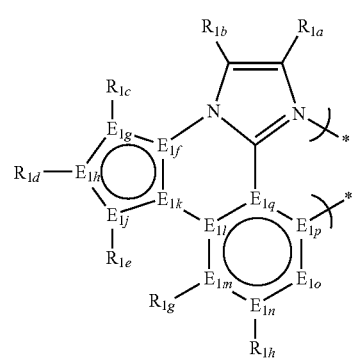

wherein
$E_{1f}$ to $E_{1q}$ and $R_{1a}$ to $R_{1h}$ are synonymous with those in the formulae (A1-1) and (A3-1); and
each of structures represented by the formulae (A1-3) and (A3-3) has a 18 π-electron structure in total.

[3] The material for an organic electroluminescence device as described in [2] above,
wherein the phosphorescent metal complex is a phosphorescent metal complex represented by the following formula (A10):

(A10)

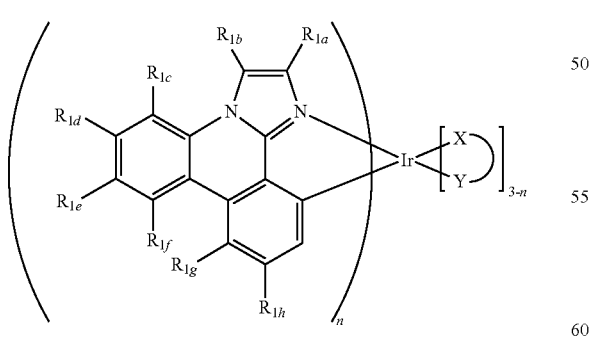

wherein
$R_{1a}$ to $R_{1h}$ are synonymous with those in the formulae (A1-3) and (A3-3);
X-Y represents at least one monoanionic bidentate ligand selected from the group consisting of the following I-1 to I-14; and n represents an integer of from 1 to 3:

I-1
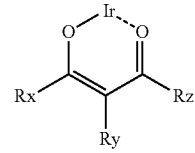

I-2
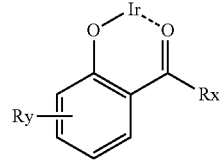

I-3
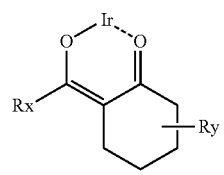

I-4
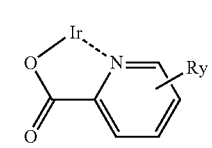

I-5
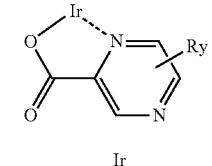

I-6
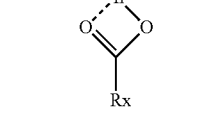

I-7
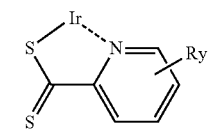

I-8
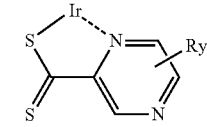

I-9
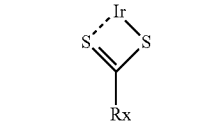

I-10
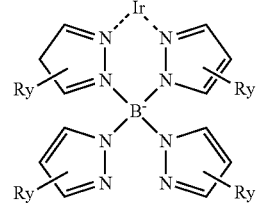

-continued

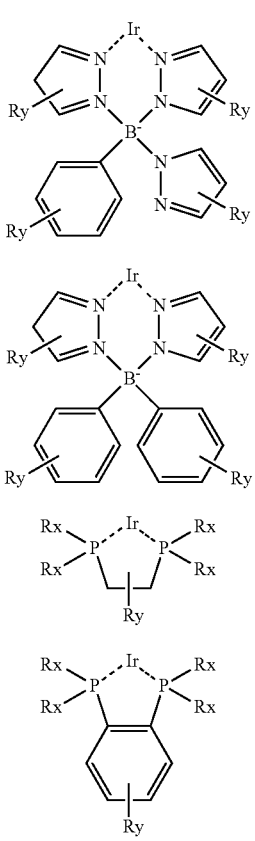

I-11

I-12

I-13

I-14 wherein
each of Rx, Ry and Rz independently represents a hydrogen atom, a fluorine atom, a hydrocarbon substituent or a fluorine-substituted hydrocarbon substituent consisting only of a carbon atom, a hydrogen atom and a fluorine atom.

[4] The material for an organic electroluminescence device as described in [3] above,
wherein the phosphorescent metal complex represented by the formula (A10) is a phosphorescent metal complex represented by the following formula (A10-1):

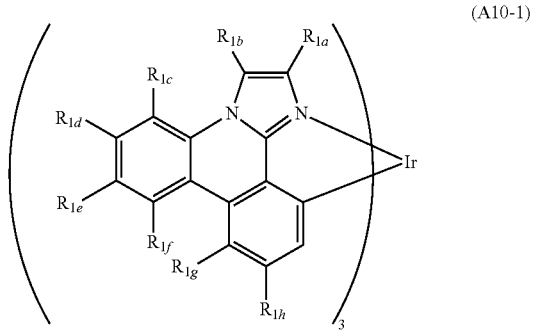

(A10-1)

wherein
$R_{1a}$ to $R_{1h}$ are synonymous with those in the formula (A10).

[5] The material for an organic electroluminescence device as described in [3] above, wherein the phosphorescent metal complex represented by the formula (A10) is a phosphorescent metal complex represented by the following formula (A20):

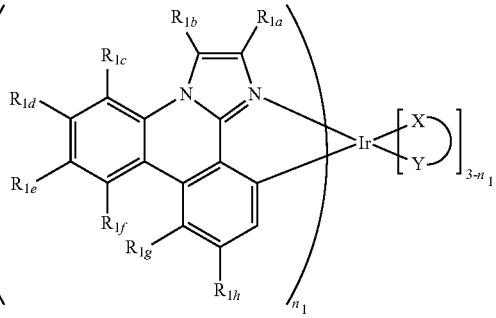

(A20)

wherein
each of $R_{1a}$ to $R_{1c}$ independently represents a hydrogen atom or a hydrocarbon substituent;
$R_{1a}$ to $R_{1h}$ may be bonded to each other to form a ring;
$n_1$ represents 1 or 2; and
X-Y, Rx, Ry and Rz are synonymous with those in the formula (A10).

[6] An organic electroluminescence device, comprising:
a substrate having thereon a pair of electrodes; and
at least one layer of organic layers including a light emitting layer between the pair of electrodes,
wherein the material for an organic electroluminescence device as described in any one of [1] to [5] above is contained in at least one layer of the organic layers.

[7] The organic electroluminescence device as described in [6] above,
wherein the material for an organic electroluminescence device as described in any one of [1] to [5] is contained in the light emitting layer.

[8] A light emitting unit, comprising:
the organic electroluminescence device as described in [6] or [7] above.

[9] A display unit, comprising:
the organic electroluminescence device as described in [6] or [7] above.

[10] An illumination unit, comprising:
the organic electroluminescence device as described in [6] or [7] above.

DESCRIPTION OF EMBODIMENTS

Figure 1:
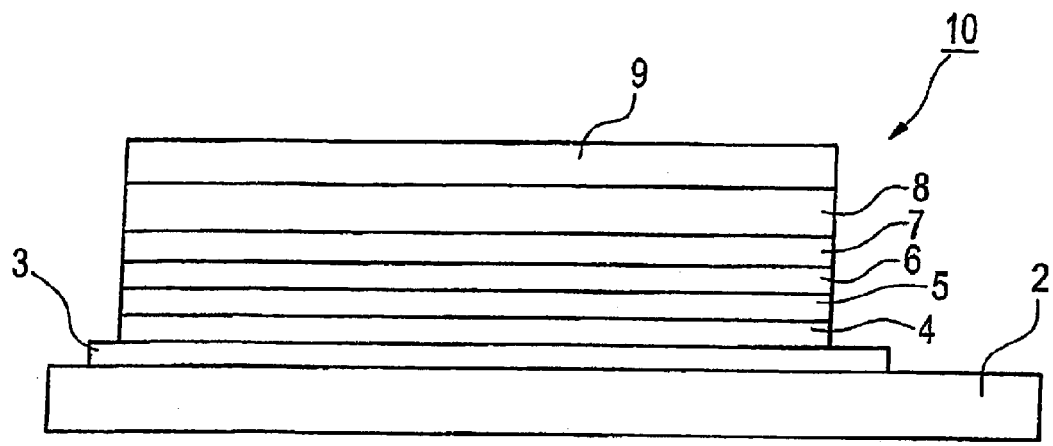
FIG. 1 is a diagrammatic view showing an example (first embodiment) of a layer constitution of an organic EL device according to the invention.

In the description for the formulae of the invention, it is expressed that not only the hydrogen atom includes its isotopes (for example, a deuterium atom, etc.), but atoms constituting each substituent include isotopes thereof.

In the invention, the terms "carbon atom number" of a substituent such as an alkyl group are meant to include the case where the substituent such as an alkyl group may be substituted with other substituent and also include the carbon atom number of such other substituent.

The material for organic EL device of the invention contains a phosphorescent metal complex containing a monoanionic bidentate ligand represented by the following formula (A1-1) or formula (A3-1), and a non-radiative metal having an atomic weight of 40 or more (this phosphorescent metal complex will be hereinafter sometimes referred to as "specified phosphorescent metal complex").

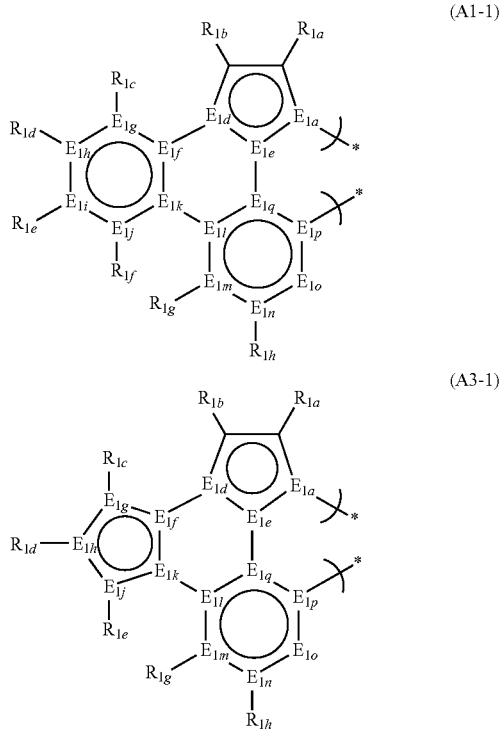

In the formulae (A1-1) and (A3-1), each of $E_{1a}$, $E_{1d}$ to $E_{1n}$, $E_{1p}$ and $E_{1q}$ independently represents a carbon atom or a hetero atom; at least one of $E_{1a}$, $E_{1d}$ and $E_{1e}$ represents a nitrogen atom; $E_{1o}$ represents CH or a nitrogen atom; each of $R_{1a}$ to $R_{1h}$ independently represents a hydrogen atom, a fluorine atom, a hydrocarbon substituent or a fluorine-substituted hydrocarbon substituent consisting only of a carbon atom, a hydrogen atom and a fluorine atom; and $R_{1a}$ to $R_{1h}$ may be bonded to each other to form a ring, provided that a content of a fluorine atom in the phosphorescent metal complex is 7% by mass or more; and that each of structures represented by the formulae (A1-1) and (A3-1) has a 18 π-electron structure in total. (In this specification, mass ratio is equal to weight ratio.)

In the invention, by selecting a ligand such that the content of the fluorine atom is 7% by mass or more relative to the total molecular weight of the complex, not only the luminous efficiency can be largely enhanced without lowering the durability of the device using this material, but a sublimation purification time of the material can be shortened.

In general, it is well known that by introducing a fluorine atom into a ligand of a metal complex, a frontier orbit of the complex is influenced by its electronic effect, and an energy gap is changed, and therefore, a light emission wavelength is changed. However, in the invention, it has been clarified that by introducing fluorine, not only the light emission wavelength can be controlled, but the luminous efficiency can be largely improved. It is known that in an Ir complex, a highly excited state derived from the d-d* transition takes a value close to minimum triplet energy (see *Inorg. Chem.*, 2006, page 8907). However, in this complex, a probability of transition into this highly excited state is high, and energy of radiationless deactivation is especially remarkable, and therefore, it has been estimated that the luminous efficiency may be likely low. It may be supposed that the fact that by introducing a fluorine atom thereinto, the fluorine atom effectively makes the highly excited state instable, thereby blocking a route as a main factor of deactivation is a cause of enhancing the efficiency.

Also, when the content of the fluorine atom in the complex is less than 7% by mass, its effect is not sufficiently displayed. In this respect, it may be supposed that in order that a difference between the minimum triplet energy and the energy in a highly excited state may be made sufficiently large, thereby preventing the transition into a highly excited state from occurring, it is necessary to introduce a certain content or more of a fluorine atom.

When the content of the fluorine atom of the phosphorescent metal complex is less than 7% by mass, the minimum triplet energy and the energy in a highly excited state are not sufficiently separated from each other, and the transition into a highly excited state still possibly takes place, and therefore, an effect of the invention, i.e., an enhancement of the luminous efficiency, is not proved.

Also, the phosphorescent metal complexes disclosed in US-A-2008/297033 and JP-A-2008-311607 have a ligand with a large surface area and have a structure where the ligand is three-dimensionally spread by an octahedral 6-coordinate structure. For that reason, the packing state among molecules does not become close but is in a state where a number of voids are present, and a chemical potential of the solid state is not stabilized so much. Therefore, it may be supposed that melting takes place in vacuo at the time of sublimation purification, thereby reducing a sublimation rate. It may be considered that when a fluorine atom is introduced into the ligand as in the invention, packing in the solid state is improved by an effect of fluorine having a strong electronegativity for attracting an electron cloud, and mutual stabilization of molecules in a solution state is inhibited due to a reduction in an intermolecular interaction to increase the chemical potential, thereby obtaining an improving effect of the sublimation purification time.

Also, there is a close relation between a crystal form and a sublimation temperature, and it may be guessed that the fact that by introducing a fluorine atom, the crystal form of a coarse body is changed is also one of the factors.

In the thus obtained material, a voltage increase to be caused following driving when formed into a device is small.

It may be estimated that this is caused due to the fact that since the time when it is exposed to a high temperature at the time of sublimation purification is short, the kind of impurities to be contained is different as compared with usual materials. Though various causes for which the voltage increases at the time of device driving may be considered, charge transporting properties of the material having been decomposed within the light emitting layer are poor, and therefore, it may be considered that a flow of both charges is disturbed. A possibility that infinitesimal impurities promote the decomposition within the luminescence device has already been suggested, and it may be supposed that this decomposition route was altered by changing the purification method.

When the content of the fluorine atom of the specified phosphorescent metal complex is excessively high, the improving effect of the sublimation purification time becomes inversely small, and the complex is coagulated in the device prepared using the obtained material so that the hue is deteriorated, too. For those reasons, the content of the fluorine atom of the specified phosphorescent metal complex is preferably 7% by mass or more and not more than 50% by mass, and more preferably 10% by mass or more and not more than 35% by mass.

In the invention, though the specified phosphorescent metal complex has a content of the fluorine atom of 7% by mass or more, it may be one containing a fluorine atom only in the main ligand, may be one containing a fluorine atom only in the ancillary ligand, or may be one containing a fluorine atom in both the main ligand and the ancillary ligand. The metal complex containing a fluorine atom in the main ligand is preferable because the effect of the invention is highly obtainable. Also, the metal complex containing a fluorine atom only in the ancillary ligand is preferable in view of the fact that the synthesis is easy as compared with the metal complex containing a fluorine atom in the main ligand. In this respect, the phosphorescent metal complex in the invention has a bidentate ligand represented by the formula (A1-1) or (A3-1) as a main ligand.

The bidentate ligand represented by either one of the formulae (A1-1) and (A3-1) is hereunder described.

In this respect, in the formulae of the ligand in the invention, * represents a coordination site to the metal; and each of a bond between $E_{1a}$ and the metal and a bond between $E_{1p}$ and the metal may be independently a covalent bond or a coordination bond. (Bidentate ligand represented by either one of the formulae (A1-1) and (A3-1))

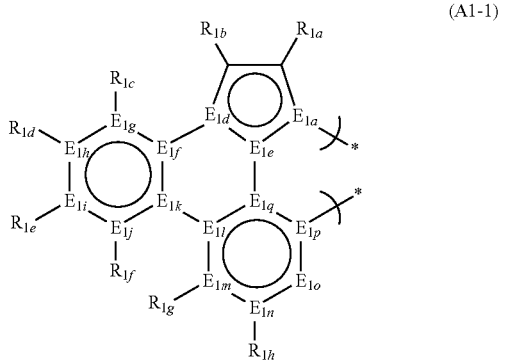

(A1-1)

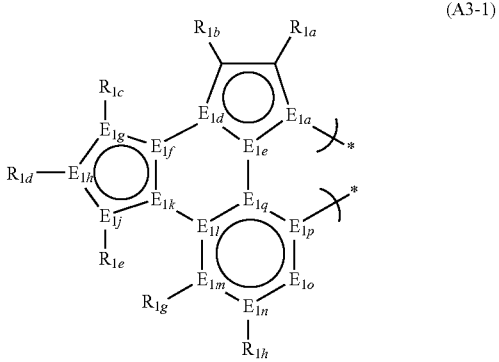

(A3-1)

In the formulae (A1-1) and (A3-1), each of $E_{1a}$, $E_{1d}$ to $E_{1n}$, $E_{1p}$ and $E_{1q}$ independently represents a carbon atom or a hetero atom; at least one of $E_{1a}$, $E_{1d}$ and $E_{1e}$ represents a nitrogen atom; $E_{1o}$ represents CH or a nitrogen atom; each of $R_{1a}$ to $R_{1h}$ independently represents a hydrogen atom, a fluorine atom, a hydrocarbon substituent or a fluorine-substituted hydrocarbon substituent consisting only of a carbon atom, a hydrogen atom and a fluorine atom; and $R_{1a}$ to $R_{1h}$ may be bonded to each other to form a ring, provided that a content of a fluorine atom in the phosphorescent metal complex is 7% by mass or more; and that each of structures represented by the formulae (A1-1) and (A3-1) has a 18 π-electron structure in total.

The hetero atom as referred to herein means an atom other than a carbon atom or a hydrogen atom. Examples of the hetero atom include oxygen, nitrogen, phosphorus, sulfur, selenium, arsenic, chlorine, bromine, silicon and fluorine.

The bidentate ligand may be bonded to other ligand to form a tridentate, tetradentate, pentadentate or hexadentate ligand.

Each of $E_{1a}$, $E_{1d}$ to $E_{1n}$, $E_{1p}$ and $E_{1q}$ independently represents a carbon atom or a hetero atom, and preferably a carbon atom or a nitrogen atom. Also, $E_{1a}$ and $E_{1p}$ are each an atom having a bond to the metal, and preferably an atom different from each other for the reason of keeping chemical stability of the complex.

The 5-membered ring formed of $E_{1a}$ to $E_{1e}$ represents a 5-membered heterocyclic ring. Specific examples of the 5-membered heterocyclic ring include pyrrole, imidazole and pyrazole. Of those, imidazole and pyrazole are preferable, and imidazole is more preferable.

Also, it is preferable that at least one of $E_{1a}$ to $E_{1e}$ represents a hetero atom; it is more preferable that at least one of $E_{1a}$ to $E_{1e}$ represents a nitrogen atom; and it is especially preferable that two of $E_{1a}$ to $E_{1e}$ represent a nitrogen atom. In the case where two of $E_{1a}$ to $E_{1e}$ represent a nitrogen atom, it is preferable that two of $E_{1a}$, $E_{1d}$ and $E_{1e}$ represent a nitrogen atom; it is more preferable that $E_{1a}$ and $E_{1d}$, or $E_{1a}$ and $E_{1e}$ represent a nitrogen atom; and it is further preferable that $E_{1a}$ and $E_{1d}$ represent a nitrogen atom.

The ring formed of $E_{1f}$ to $E_{1k}$ is a 5-membered or 6-membered aromatic hydrocarbon ring or heterocyclic ring, and preferably a 6-membered aromatic hydrocarbon ring. Specific examples of the ring formed of $E_{1f}$ to $E_{1k}$ include benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine and triazine. Of those, benzene is preferable.

$E_{1o}$ represents CH or a nitrogen atom. That is, $E_{1o}$ does not have a substituent. According to the investigations made by the present inventors, a complex in which $E_{1o}$ has a substituent is lowered in durability and efficiency and also lowered in stability against thermal exposure. It may be considered that this is caused due to the fact that the bond length to the metal atom is expanded by a steric hindrance effect by the substituent, and non-radiative deactivation is easy to take place due to expansion and contraction of this bond, and therefore, luminous efficiency is lowered. Also, it may be supposed that in view of the facts that the length of the bond is expanded and that the chemical stability is lowered, the device driving durability and heat stability are lowered.

$E_{1o}$ is preferably CH.

The ring formed of $E_{1l}$ to $E_{1q}$ is a 6-membered aromatic hydrocarbon ring or heterocyclic ring, and preferably a 6-membered aromatic hydrocarbon ring. Specific examples of the ring formed of $E_{1l}$ to $E_{1q}$ include benzene, pyridine, pyrazine, pyrimidine, pyridazine and triazine. Of those, pyridine and benzene are preferable, and benzene is more preferable.

Each of $R_{1a}$ to $R_{1h}$ independently represents a hydrogen atom, a fluorine atom, a hydrocarbon substituent or a fluorine-substituted hydrocarbon substituent consisting only of a carbon atom, a hydrogen atom and a fluorine atom; and $R_{1a}$ to $R_{1h}$ may be bonded to each other to form a ring.

The hydrocarbon substituent is a monovalent or divalent, chained, branched or cyclic substituent and means a substituent consisting only of a carbon atom and a hydrogen atom.

Examples of the monovalent hydrocarbon substituent include an alkyl group having from 1 to 20 carbon atoms; an alkyl group having from 1 to 20 carbon atoms and substituted with one or more groups selected among an alkyl group having from 1 to 20 carbon atoms, a cycloalkyl group having from 3 to 8 carbon atoms and an aryl group; a cycloalkyl group having from 3 to 8 carbon atoms; a cycloalkyl group having from 3 to 8 carbon atoms and substituted with one or more groups selected among an alkyl group having from 1 to 20 carbon atoms, a cycloalkyl group having from 3 to 8 carbon atoms and an aryl group; an aryl group having from 6 to 18 carbon atoms; and an aryl group substituted with one or more groups selected among an alkyl group having from 1 to 20 carbon atoms, a cycloalkyl group having from 3 to 8 carbon atoms and an aryl group.

Examples of the divalent hydrocarbon group include —CH₂—, —CH₂CH₂—, —CH₂CH₂CH₂— and a 1,2-phenylene group.

The hydrocarbon substituent is preferably an alkyl group having from 1 to 20 carbon atoms or an aryl group. Specific examples of the alkyl group which is preferable include a methyl group, an ethyl group, an isopropyl group, an n-butyl group, an isobutyl group, a neopentyl group and an n-hexyl group. Of those, a methyl group, an isopropyl group and a neopentyl group are more preferable. Specific examples of the aryl group which is preferable include a phenyl group, a naphthyl group and an anthranyl group, each of which may be substituted with a hydrocarbon substituent. In that case, though a preferred range of the hydrocarbon substituent to be substituted is the same as that in the foregoing hydrocarbon substituent, it is preferable that a total number of carbon atoms is not more than 20 from the viewpoints of properly controlling the molecular weight and imparting a vapor deposition aptitude.

Examples of the fluorine-substituted hydrocarbon substituent include groups obtained by substituting at least one hydrogen atom of each of the foregoing hydrocarbon substituents with a fluorine atom.

At least one of $R_{1a}$ to $R_{1h}$ is preferably a fluorine atom or a fluorine-substituted hydrocarbon substituent, and more preferably an alkyl group represented by —$C_mH_lF_{2m-l+1}$ (wherein m represents an integer of from 0 to 10; and l represents an integer of from 0 to 2 m) or an aryl group having from 6 to 10 carbon atoms and substituted with at least one fluorine atom. A preferred range of the alkyl group or the aryl group, each of which is substituted with fluorine, is the same as that in the foregoing hydrocarbon substituent. From the viewpoint of suppressing phase separation, a number of fluorine atoms to be contained in one hydrocarbon substituent is preferably not more than 10, and more preferably not more than 6.

Examples of the fluorine-substituted hydrocarbon substituent include the following groups.

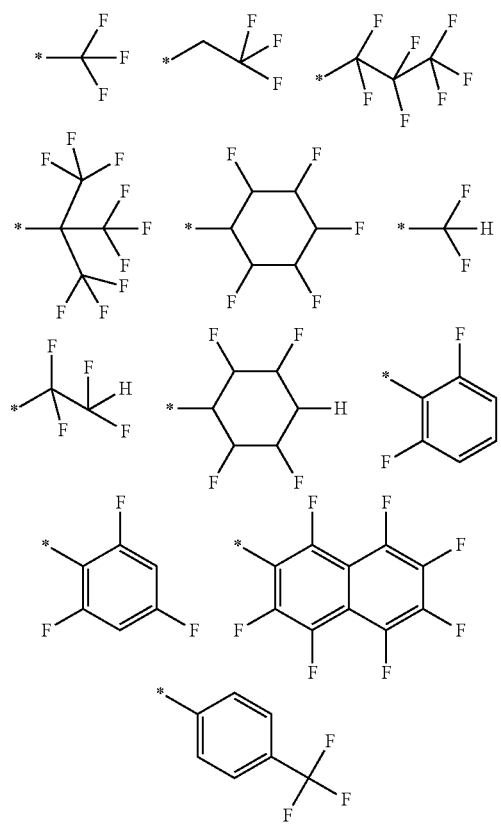

Also, from the viewpoint of chemical stability of the complex, at least one of $R_{1a}$ to $R_{1h}$ is preferably a substituted or unsubstituted aryl group having a dihedral angle against the mother structure of 70 degrees or more, more preferably a substituent represented by the following formula ss-1, and further preferably a 2,6-disubstituted aryl group. It is the most preferable that $R_{1b}$ is a 2,6-disubstituted aryl group.

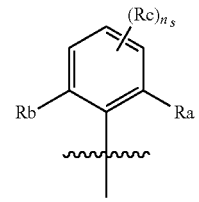

ss-1

In the formula ss-1, each of Ra and Rb independently represents a hydrogen atom, a fluorine atom, an alkyl group, a fluorine-substituted alkyl group, an aryl group or a fluorine-substituted aryl group; Rc represents a fluorine atom, an alkyl group, a fluorine-substituted alkyl group, an aryl group or a fluorine-substituted aryl group; $n_s$ represents an integer of from 0 to 3; and in the case where $n_s$ is 2 or more, each Rc may be the same as or different from every other Rc.

The alkyl group represented by each of Ra, Rb and Rc has preferably from 1 to 30 carbon atoms, more preferably from 1 to 20 carbon atoms, and especially preferably from 1 to 10 carbon atoms, and examples thereof include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl and trifluoromethyl. Of those, a methyl group and an isopropyl group are preferable.

The aryl group represented by each of Ra, Rb and Rc has preferably from 6 to 30 carbon atoms, more preferably from 6 to 20 carbon atoms, and especially preferably from 6 to 12 carbon atoms, and examples thereof include phenyl, o-methylphenyl, m-methylphenyl, p-methylphenyl, 2,6-xylyl, p-cumenyl, mesityl, naphthyl and anthranyl. Of those, a phenyl group, a 2,6-xylyl group and a mesityl group are preferable, and a phenyl group is more preferable.

Examples of the fluorine-substituted alkyl group or the fluorine-substituted aryl group represented by each of Ra, Rb and Rc include those obtained by substituting one or more hydrogen atoms of each of the foregoing alkyl groups or aryl groups with a fluorine atom. A preferred range of the hydrocarbon structure is the same as that in the alkyl group or the aryl group.

It is preferable that at least one of Ra and Rb is selected among a fluorine atom, an alkyl group, a fluorine-substituted alkyl group, an aryl group and a fluorine-substituted aryl group; it is more preferable that at least one of Ra and Rb is selected among a fluorine atom, an alkyl group and a fluorine-substituted alkyl group; it is further preferable that both of Ra and Rb are a fluorine atom, an alkyl group or a fluorine-substituted alkyl group; and it is the most preferable that both of Ra and Rb are a fluorine atom, a methyl group, a trifluoromethyl group or an isopropyl group.

Also, $n_s$ is preferably 0 or 1.

Examples of the 2,6-disubstituted aryl group which is preferable include a 2,6-dimethylphenyl group, a 2,6-difluorophenyl group, a pentafluorophenyl group, a 2,6-di(trifluoromethyl)phenyl group, a 2,4,6-trimethylphenyl group, a 2,6-diisopropylphenyl group, a 2,4,6-triisopropylphenyl group, a 2,4,6-trifluorophenyl group, a 2,6-dimethyl-4-phenylphenyl group, a 2,6-dimethyl-4-(2,6-dimethylpyridin-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, a 2,6-diisopropyl-4-(3,5-dimethylphenyl)phenyl group, a 2,6-diisopropyl-4-(pyridin-4-yl)phenyl group, a 2,6-di(3,5-dimethylphenyl)phenyl group and substituents obtained by substituting each of those groups with one or more fluorine atoms.

On the other hand, it is preferable that at least one of $R_{1a}$ to $R_{1h}$ is an alkyl group or a fluorine-substituted alkyl group. In particular, it is more preferable that $R_{1e}$ is an alkyl group or a fluorine-substituted alkyl group. It is preferable that the alkyl group or the fluorine-substituted alkyl group has a structure in which it is branched at a site far from the benzyl position composed of 4 or more carbon atoms. The alkyl group or the fluorine-substituted alkyl group is preferably a methyl group, a trifluoromethyl group, a hexafluoroisopropyl group, an isopropyl group, a neopentyl group or a nonafluoroneopentyl group, and more preferably a neopentyl group.

It is preferable that at least one of $R_{1a}$ and $R_{1b}$ is an electron-donating group; it is more preferable that $R_{1a}$ is an electron-donating substituent; and it is the most preferable that $R_{1a}$ is a methyl group.

In the invention, the bidentate ligand represented by either one of the formulae (A1-1) and (A3-1) is preferably a monoanionic bidentate ligand represented by the formula (A1-1).

The bidentate ligand represented by the formula (A1-1) or (A3-1) is preferably a monoanionic bidentate ligand represented by the following formula (A1-2) or (A3-2).

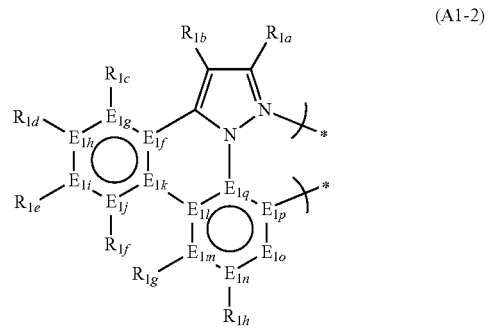

(A1-2)

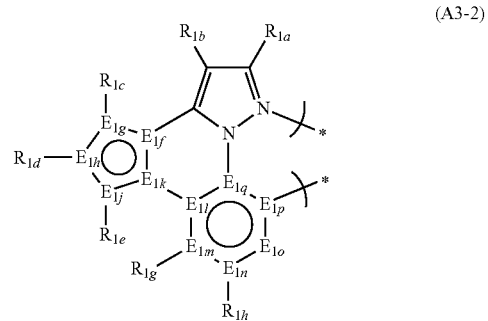

(A3-2)

In the formulae (A1-2) and (A3-2), definitions and preferred ranges of $E_{1f}$ to $E_{1k}$, $E_{1l}$ to $E_{1q}$ and $R_{1a}$ to $R_{1b}$ are the same as those in the formulae (A1-1) and (A3-1); and each of structures represented by the foregoing formulae has a 18 π-electron structure in total.

The monoanionic bidentate ligand represented by each of the formulae (A1-1) and (A3-1) is more preferably a monoanionic bidentate ligand represented by the following formula (A1-3) or (A3-3).

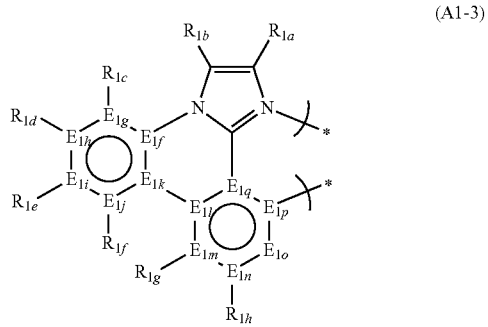

(A1-3)

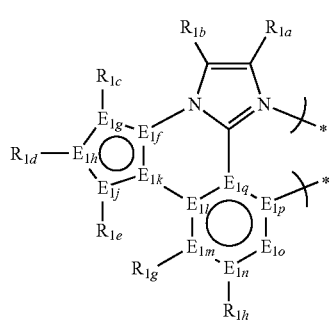

(A3-3)

In the formulae (A1-3) and (A3-3), definitions and preferred ranges of $E_{1f}$ to $E_{1k}$, $E_{1l}$ to $E_{1q}$ and $R_{1a}$ to $R_{1h}$ are the same as those in the formulae (A1-1) and (A3-1); and each of structures represented by the foregoing formulae has a 18 π-electron structure in total.

The monoanionic bidentate ligand represented by each of the formulae (A1-3) and (A3-3) is preferably a monoanionic bidentate ligand represented by the following formula (A1-4) or (A3-4).

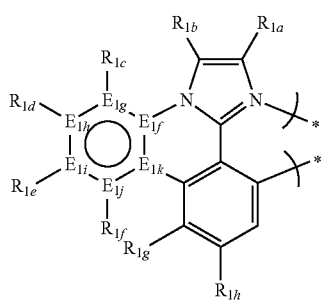

(A1-4)

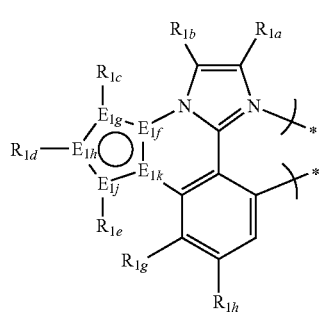

(A3-4)

In the formulae (A1-4) and (A3-4), definitions and preferred ranges of $E_{1f}$ to $E_{1k}$ and $R_{1a}$ to $R_{1h}$ are the same as those in the formulae (A1-3) and (A3-3). In particular, the monoanionic bidentate ligand represented by the formula (A1-4) is preferable. Also, each of structures represented by the foregoing formulae has a 18 π-electron structure in total.

The monoanionic bidentate ligand represented by the formula (A1-4) is preferably a monoanionic bidentate ligand represented by the following formula (A1-5).

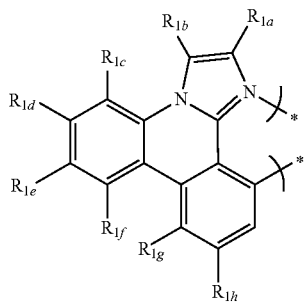

(A1-5)

In the formula (A1-5), definitions and preferred ranges of $R_{1a}$ to $R_{1h}$ are the same as those in the formula (A1-4).

The monoanionic bidentate ligand represented by the formula (A1-5) is preferably a monoanionic bidentate ligand represented by the following formula (A1-6), (A1-7) or (A1-8).

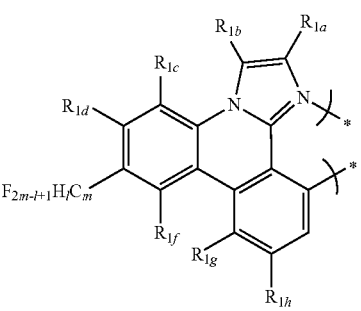

(A1-6)

In the formula (A1-6), definitions and preferred ranges of $R_{1a}$ to $R_{1h}$ are the same as those in the formula (A1-5); m represents an integer of from 0 to 10; and l represents an integer of from 0 to 2 m.

In the formula (A1-6), m is preferably an integer of from 3 to 6. Also, it is preferable that $-C_mH_lF_{2m-l+1}$ has two or more fluorine atoms. Also, it is preferable that $-C_mH_l F_{2m-l+1}$ is branched in one or more places; and it is more preferable that $-C_mH_lF_{2m-l+1}$ is branched in one or more places and does not have a branched chain at the benzyl position.

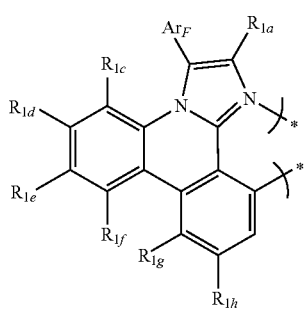

(A1-7)

In the formula (A1-7), definitions and preferred ranges of $R_{1a}$ to $R_{1h}$ are the same as those in the formula (A1-5); and $Ar_F$ represents an aryl group having from 6 to 10 carbon atoms and substituted with one or more fluorine atoms or fluorine atom-containing substituents.

It is preferable that $Ar_F$ has a substituent at an ortho-position thereof; and it is more preferable that $Ar_F$ is a 2,6-disubstituted phenyl group.

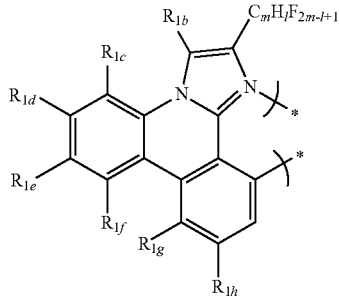

(A1-8)

In the formula (A1-8), definitions and preferred ranges of $R_{1a}$ to $R_{1h}$ are the same as those in the formula (A1-5); m represents an integer of from 0 to 10; and l represents an integer of from 0 to 2 m.

In the formula (A1-8), m is preferably an integer of not more than 3. It is preferable that the group represented by $—C_mH_lF_{2m-l+1}$ has two or more fluorine atoms.

The metal in the specified phosphorescent metal complex according to the invention is selected among non-radiative metals having an atomic weight of 40 or more. Such a metal is more preferably any one of Re, Ru, Os, Rh, Ir, Pd, Pt, Cu and Au; further preferably Os, Ir or Pt; and especially preferably Ir or Pt. From the viewpoints of high luminous efficiency, high complex stability and carrier balance control of hole and electron transport within the light emitting layer, the metal is most preferably Ir.

In the invention, the metal complex composed of the main ligand represented by any one of the formulae (A1-1) to (A3-4) may be constituted of a combination of a main ligand or a tautomer thereof and an ancillary ligand or a tautomer thereof, or all of the ligands of the metal complex may be constituted only of a partial structure represented by a main ligand or a tautomer thereof.

Furthermore, the metal complex according to the invention may have, as an ancillary ligand, a ligand which is well-known as a so-called ligand by those skilled in the art and which is used for the formation of a conventionally known metal complex (also referred to as "coordination compound"), if desired.

From the viewpoint of suitably obtaining the effects described in the invention, the metal complex is preferably constituted of one or two kinds of ligands, and more preferably one kind of a ligand. From the viewpoint of easy synthesis during the introduction of a reactive group into the complex molecule, the metal complex is also preferably constituted of two kinds of ligands.

As the ligand which is used for conventionally known metal complexes, there are various known ligands. Examples thereof include ligands described in, for example, H. Yersin, *Photochemistry and Photophysics of Coordination Compounds*, published by Springer-Verlag, 1987; and YAMAMOTO, Akio, *Organometallic Chemistry—Principles and Applications*, published by Shokabo Publishing Co., Ltd., 1982 (for example, halogen ligands (preferably, a chlorine ligand), nitrogen-containing heteroaryl ligands (for example, bipyridyl, phenanthroline, etc.) and diketone ligands (for example, acetylacetone, etc.). The ancillary ligand of the invention is preferably a diketone or a picolinic acid derivative.

Specific examples of the ancillary ligand are enumerated below, but it should not be construed that the invention is limited thereto.

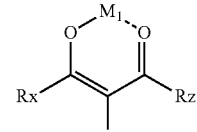

I-1

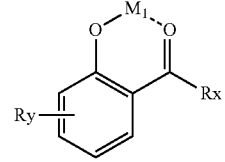

I-2

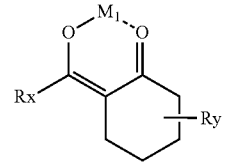

I-3

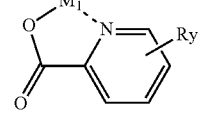

I-4

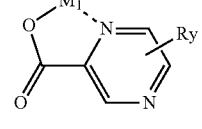

I-5

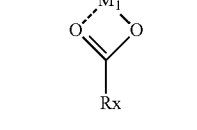

I-6

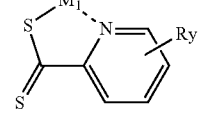

I-7

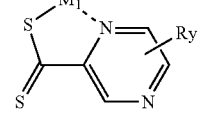

I-8

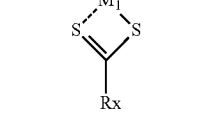

I-9

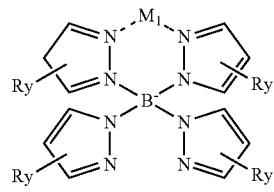

I-10

I-11
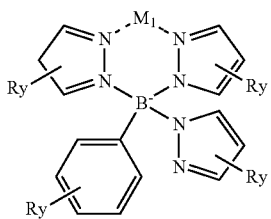

I-12
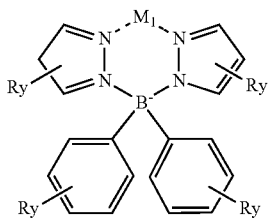

I-13
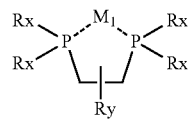

I-14
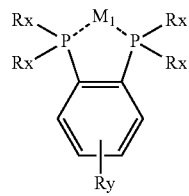

In the foregoing examples of the ancillary ligand, $M_1$ represents a non-radiative metal atom having an atomic weight of 40 or more and coordinating to each of the formulae (A1-1) to (A1-8) and (A3-1) to (A3-4). Each of Rx, Ry and Rz independently represents a hydrogen atom, a fluorine atom, a hydrocarbon substituent or a fluorine-substituted hydrocarbon substituent consisting only of a carbon atom, a hydrogen atom and a fluorine atom. In view of the facts that a complex synthesis method is generally known and that the synthesis is easy, I-1, I-4 and I-5 are preferable, with I-4 being the most preferable. In the case where such an ancillary ligand contains a fluorine atom or a fluorine-substituted hydrocarbon substituent, the ancillary ligand can be synthesized by a known synthesis example by using a corresponding ligand precursor. For example, similar to the method disclosed on page 37 of JP-A-2008-311607, it can be synthesized by a method described below while using commercially available difluoroacetylacetone.

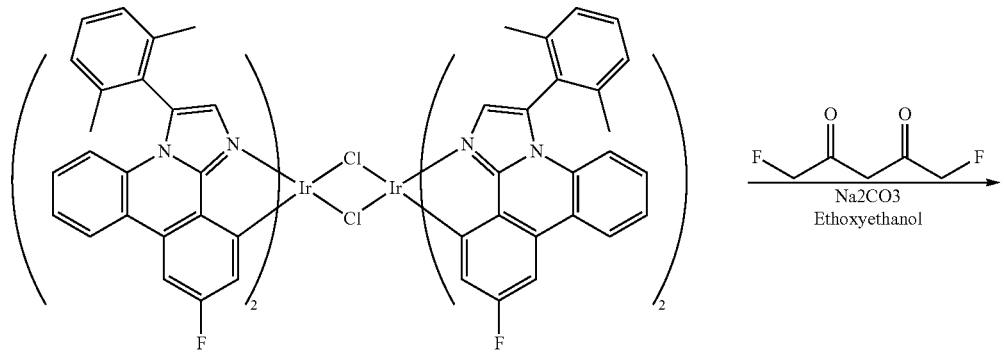

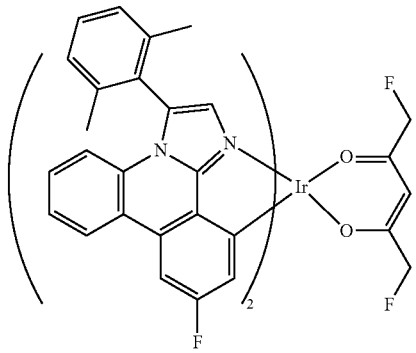

A definition and a preferred range of the hydrocarbon substituent or the fluorine-substituted hydrocarbon substituent consisting only of a carbon atom, a hydrogen atom and a fluorine atom are the same as the definitions and preferred ranges of $R_{1a}$ to $R_{1b}$ in the formulae (A1-1) to (A1-8) and (A3-1) to (A3-4).

In the invention, the phosphorescent metal complex containing a monoanionic bidentate ligand represented by any one of the formulae (A1-1) and (A3-1) and a metal having an atomic weight of 40 or more and having a content of a fluorine atom of 7% by mass or more is preferably a phosphorescent metal complex represented by the following formula (A10).

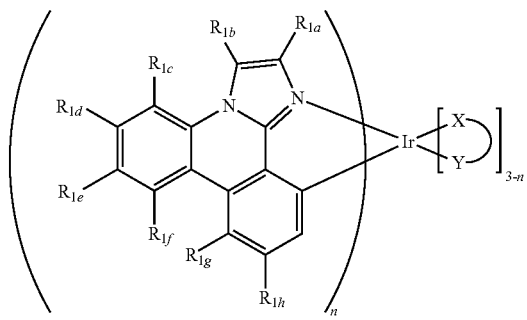

(A10)

In the formula (A10), definitions and preferred ranges of $R_{1a}$ to $R_{1h}$ are the same as those in the formulae (A1-1) and (A3-1); X-Y represents at least one monoanionic bidentate ligand selected from the group consisting of the foregoing I-1 to I-14; and n represents an integer of from 1 to 3.

X-Y represents an ancillary ligand, and specifically, the same ligands as described previously can be suitably used. X-Y is more preferably an acetylacetonate ligand or a substituted acetylacetonate ligand.

The phosphorescent metal complex represented by the foregoing formula (A10) includes the case where n is 3 (the case where an ancillary ligand is not contained) and the case where n is 1 or 2 (the case where an ancillary ligand is contained).

What n is 3 is preferable for the reasons that many light emitting coloring matter structures are contained and that the durability is enhanced.

In the case where n is 3, the foregoing formula (A10) is represented by the following formula (A10-1).

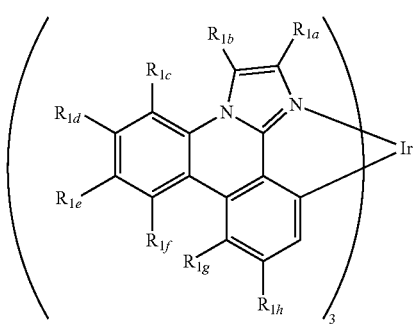

(A10-1)

In the formula (A10-1), definitions and preferred ranges of $R_{1a}$ to $R_{1h}$ are the same as those in the formula (A10).

In the invention, the specified phosphorescent metal complex represented by the foregoing formula (A10) is preferably represented by the following formula (A10-2).

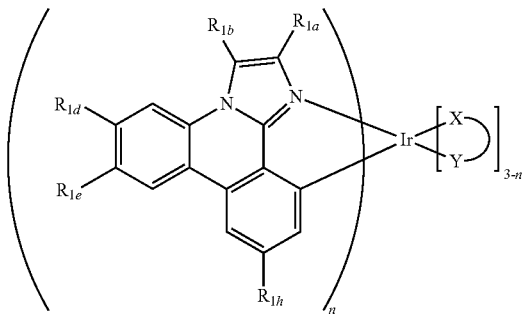

(A10-2)

In the formula (A10-2), definitions and preferred ranges of $R_{1a}$, $R_{1b}$, $R_{1d}$, $R_{1e}$ and $R_{1h}$ are the same as those in the formula (A10).

The phosphorescent metal complex represented by the formula (A10-2) is preferably a phosphorescent metal complex represented by the following formula (A11), (A12) or (A13).

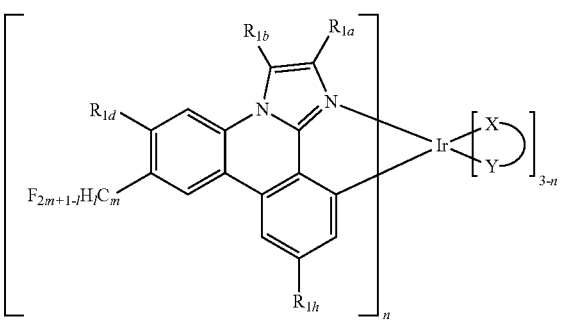

(A11)

In the formula (A11), definitions and preferred ranges of $R_{1d}$, $R_{1b}$, $R_{1a}$, $R_{1h}$ and X-Y are the same as those in the formula (A10-2); m represents an integer of from 0 to 10; l represents an integer of from 0 to 2 m; and n represents an integer of from 1 to 3.

In the formula (A11), m is preferably an integer of from 3 to 6. Also, it is preferable that —$C_mF_{2m-l+1}$ has two or more fluorine atoms. Also, it is preferable that —$C_mH_lF_{2m-l+1}$ is branched in one or more places; and it is more preferable that —$C_mH_lF_{2m-l+1}$ is branched in one or more places and does not have a branched chain at the benzyl position. n is preferably 3.

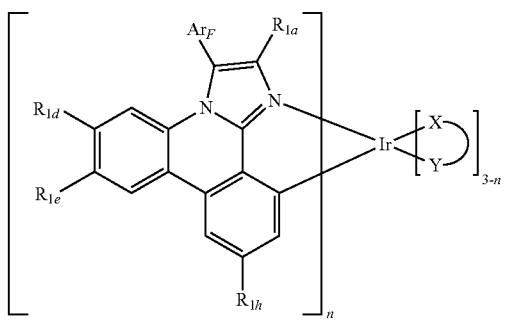

(A12)

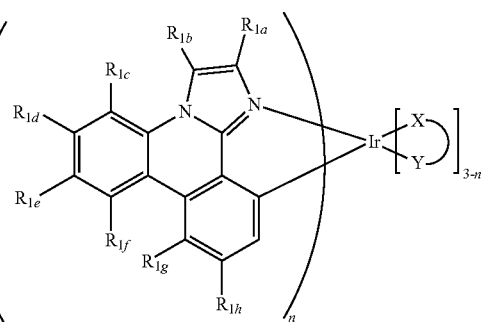

(A20)

In the formula (A12), definitions and preferred ranges of $R_{1a}$, $R_{1d}$, $R_{1e}$, $R_{1h}$ and X-Y are the same as those in the formula (A10-2); $Ar_F$ represents an aryl group having from 6 to 10 carbon atoms and substituted with one or more fluorine atoms or fluorine atom-containing substituents; and n represents an integer of from 1 to 3.

It is preferable that $Ar_F$ has a substituent at an ortho-position thereof; and it is more preferable that $Ar_F$ is a 2,6-disubstituted phenyl group. n is preferably 3.

In the formula (A20), each of $R_{1a}$ to $R_{1c}$ independently represents a hydrogen atom or a hydrocarbon substituent; n represents 1 or 2; and X-Y represents at least one monoanionic bidentate ligand selected among the following I-1 to I-14.

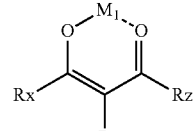

I-1

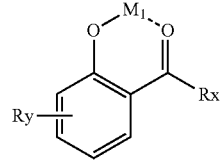

I-2

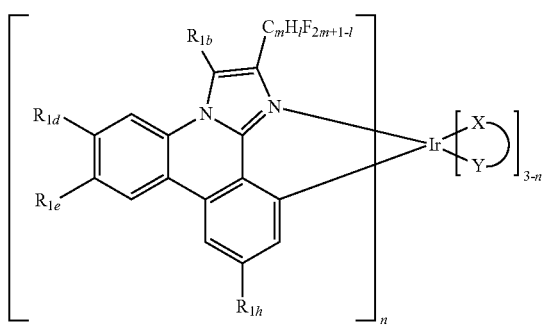

(A13)

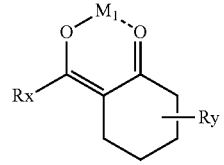

I-3

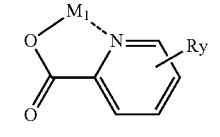

I-4

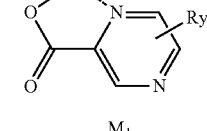

I-5

In the formula (A13), definitions and preferred ranges of $R_{1a}$, $R_{1d}$, $R_{1e}$, $R_{1h}$ and X-Y are the same as those in the formula (A10-2); m represents an integer of from 0 to 10; l represents an integer of from 0 to 2 m; and n represents an integer of from 1 to 3.

In the formula (A13), m is preferably an integer of not more than 3. It is preferable that the group represented by —$C_mH_lF_{2m-l+1}$ has two or more fluorine atoms. n is preferably 3.

In the case where the phosphorescent metal complex represented by the formula (A10) has a fluorine atom only in an ancillary ligand thereof, it is preferably a phosphorescent metal complex represented by the following formula (A20).

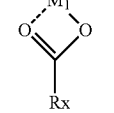

I-6

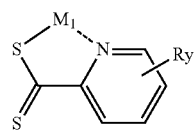

I-7

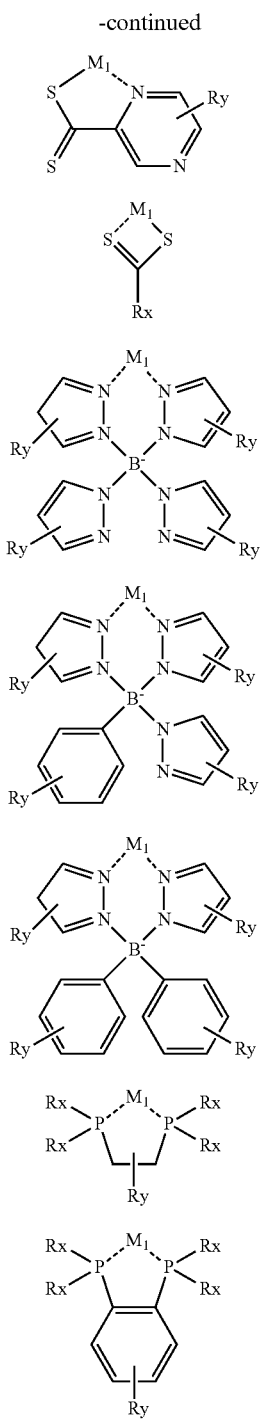

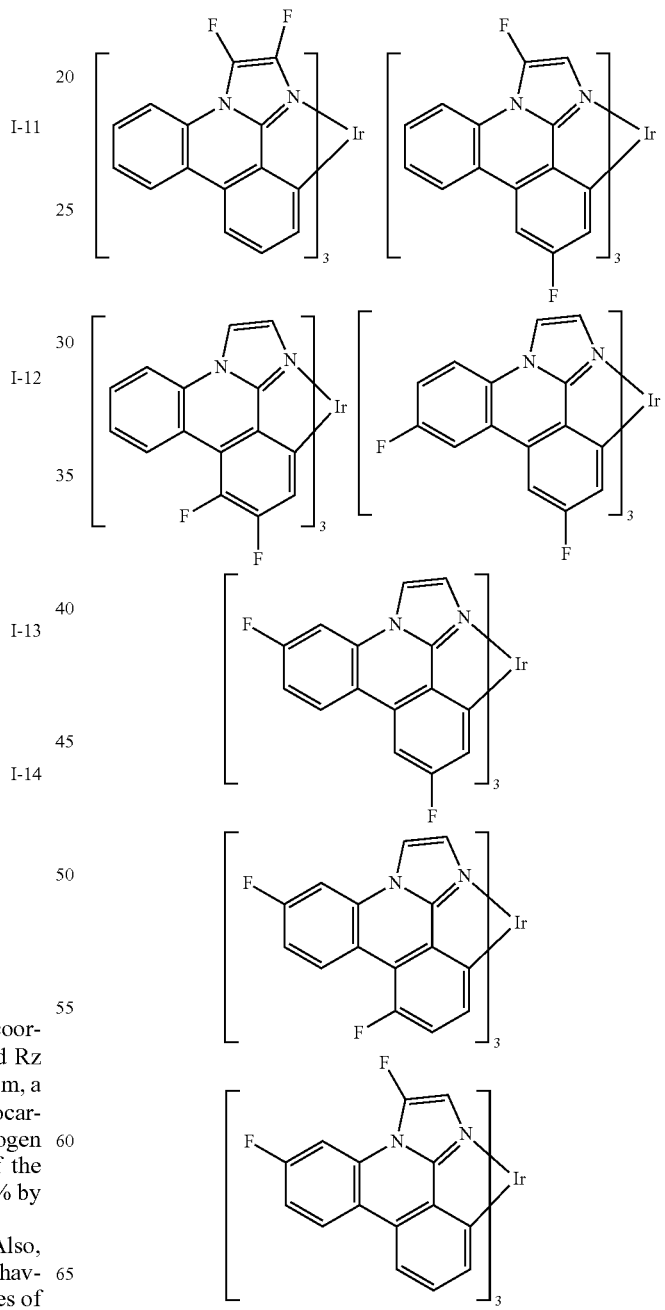

In the foregoing formulae, $M_1$ represents an Ir atom coordinating to the formula (A20); and each of Rx, Ry and Rz independently represents a hydrogen atom, a fluorine atom, a hydrocarbon substituent or a fluorine-substituted hydrocarbon substituent consisting only of a carbon atom, a hydrogen atom and a fluorine atom, provided that a content of the fluorine atom in the phosphorescent metal complex is 7% by mass or more.

It is preferable that X-Y is represented by I-1 or I-4. Also, the hydrocarbon substituent is preferably an alkyl group having from 1 to 20 carbon atoms or an aryl group. Examples of the fluorine-substituted hydrocarbon substituent include groups obtained by substituting at least one hydrogen atom of each of the foregoing hydrocarbon substituents with a fluorine atom. Preferred examples of Rx, Ry and Rz include a hydrogen atom, a fluorine atom, an alkyl group having not more than 6 carbon atoms, a phenyl group or a group obtained by substituting the alkyl group or phenyl with one or more fluorine atoms.

In the invention, specific examples of the phosphorescent metal complex containing a monoanionic bidentate ligand represented by the formula (A1-1) or (A3-1) and a metal having an atomic weight of 40 or more and having a content of a fluorine atom of 7% by mass or more are enumerated below, but it should not be construed that the invention is limited thereto.

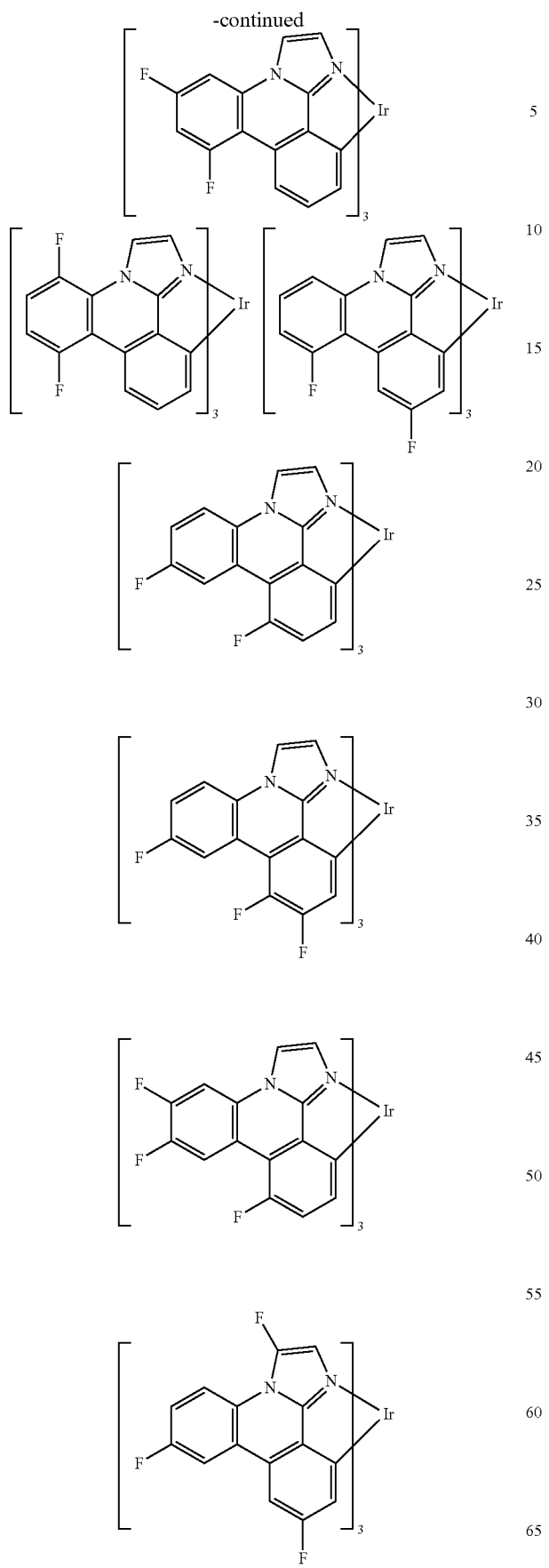
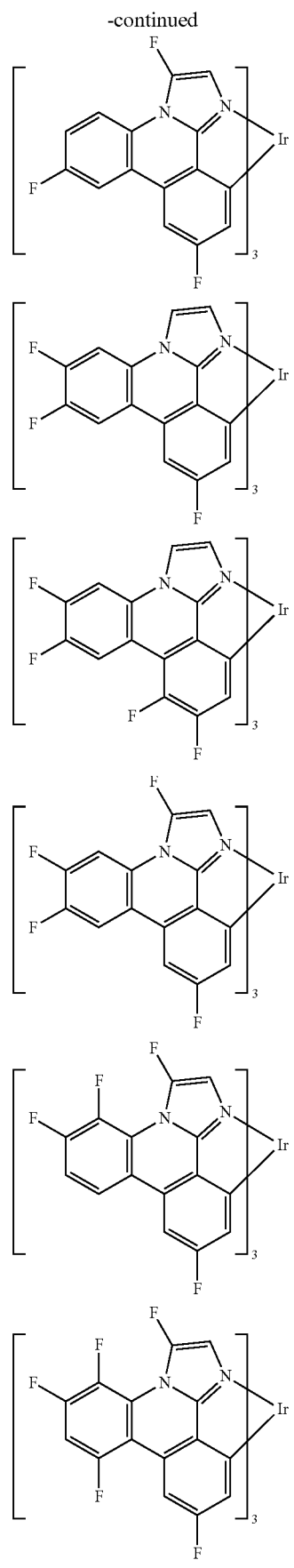

-continued
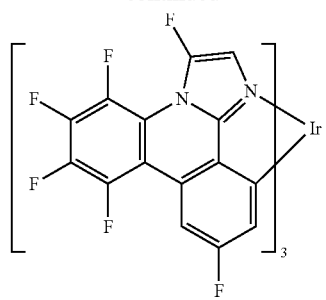
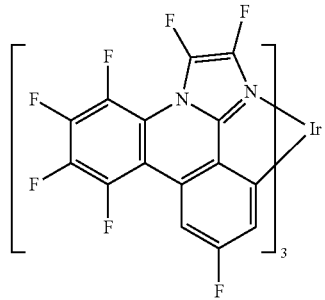
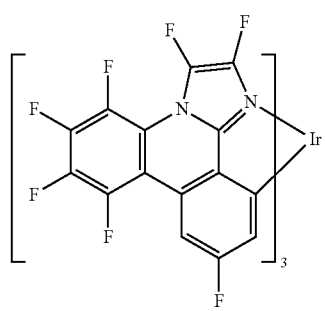
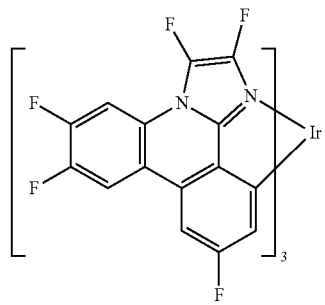
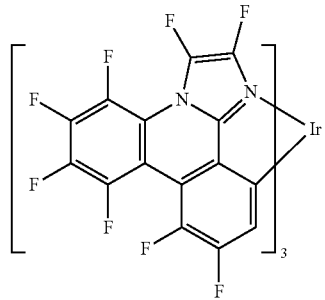
-continued
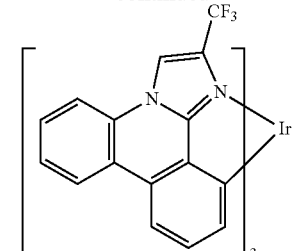
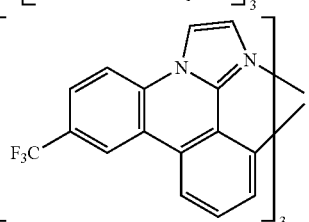
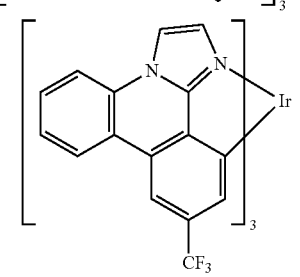
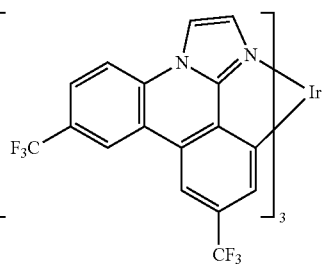
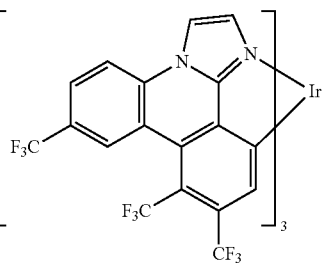
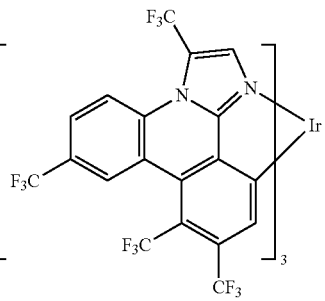

31
-continued
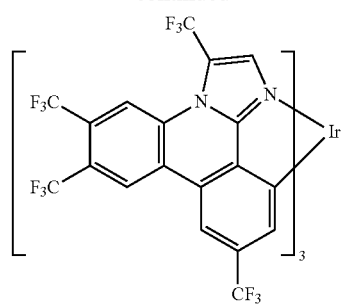
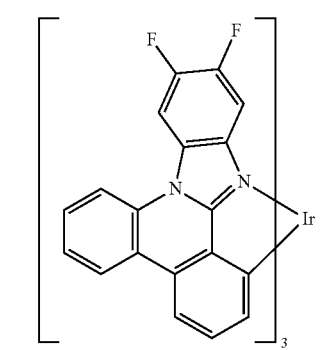
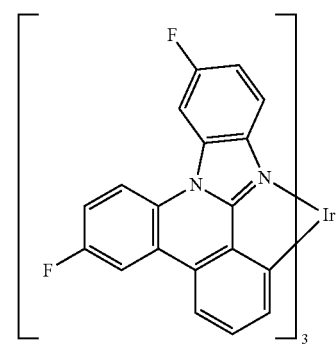
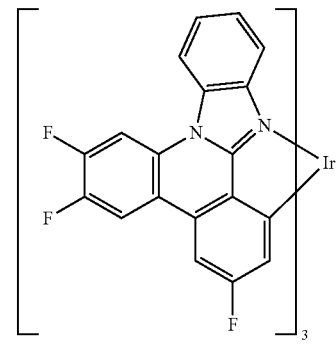
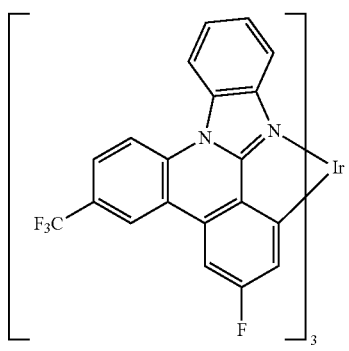
32
-continued
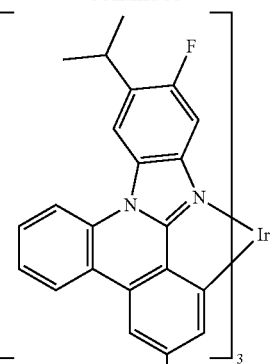
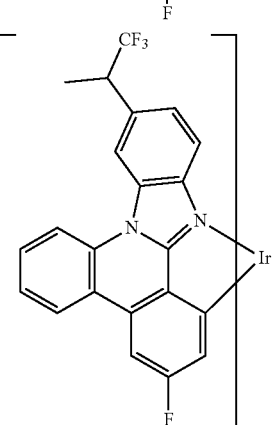
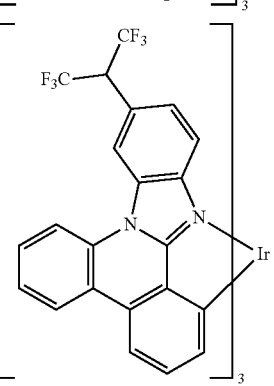
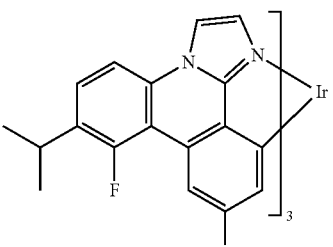
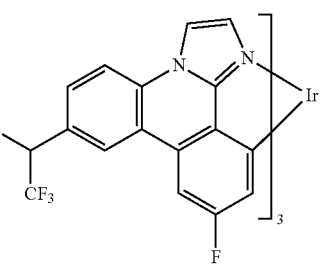

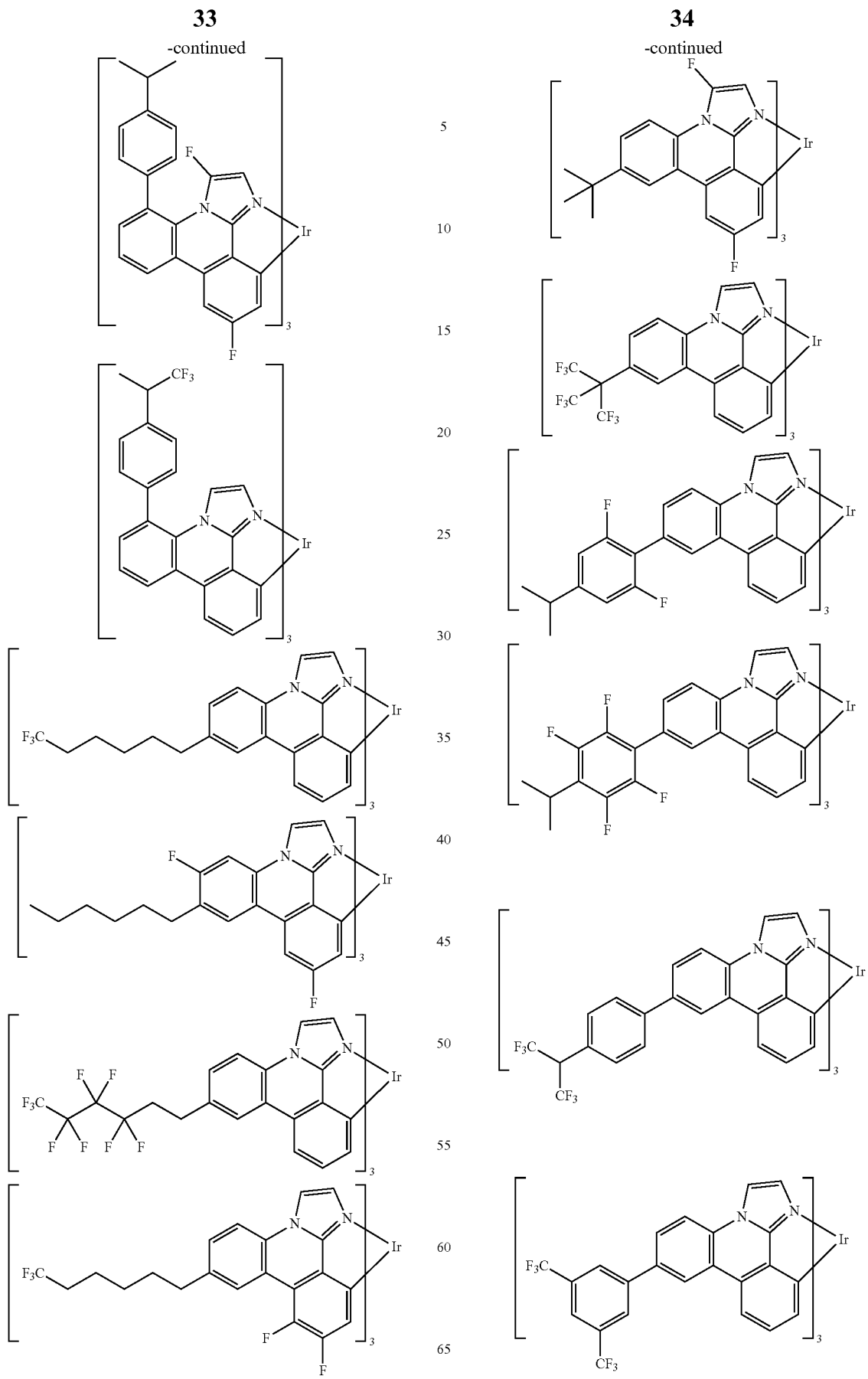

35
-continued
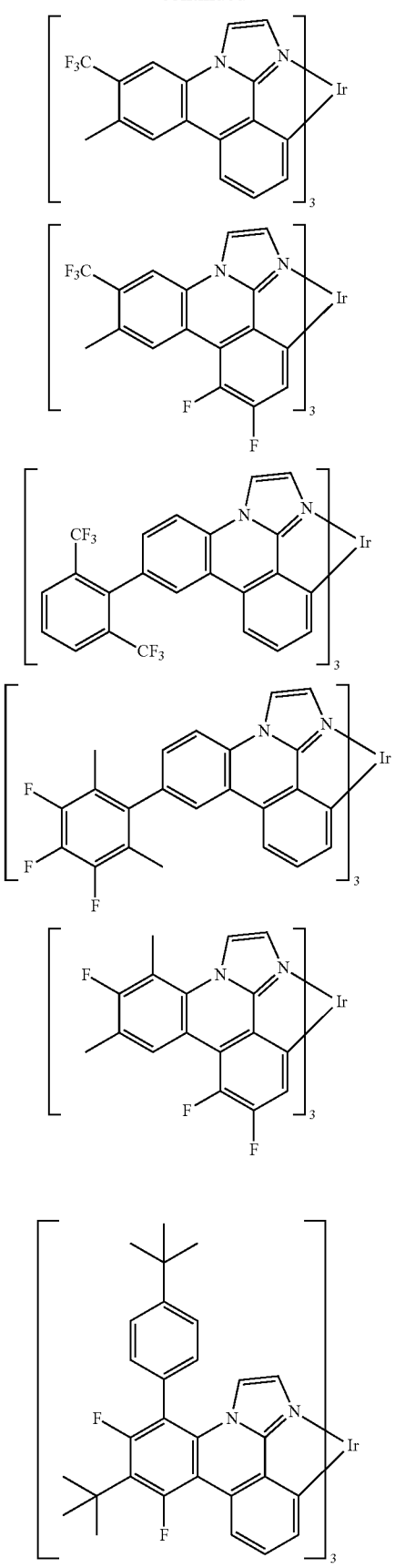
36
-continued
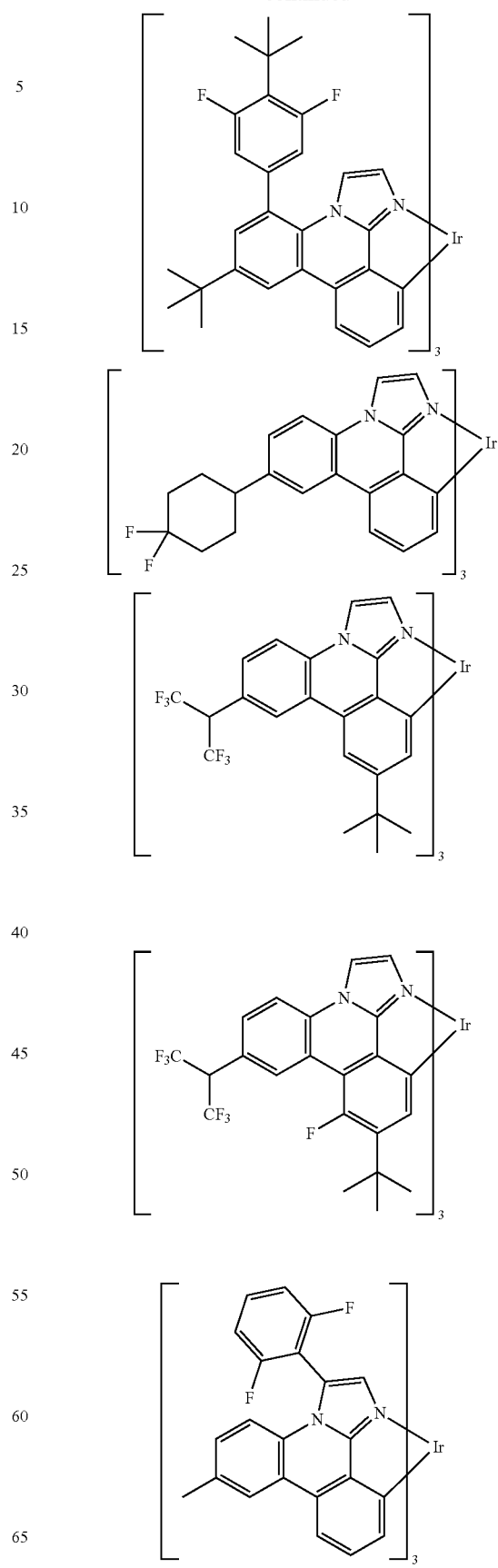

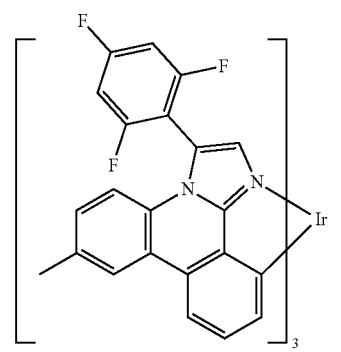
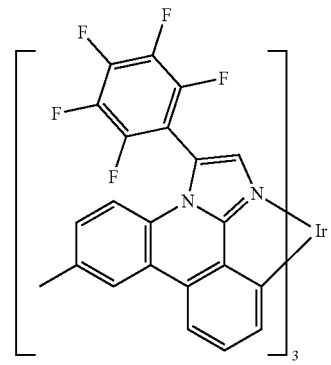
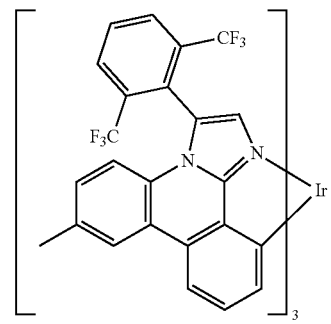
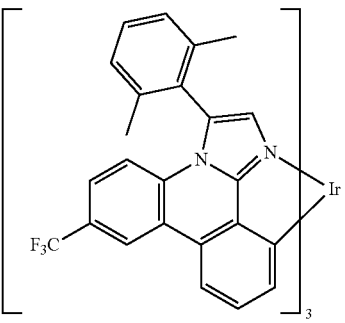
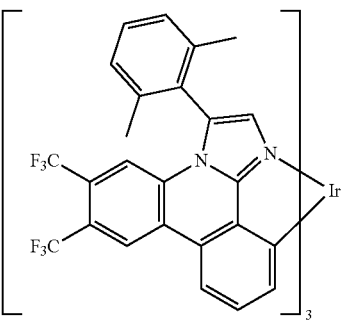
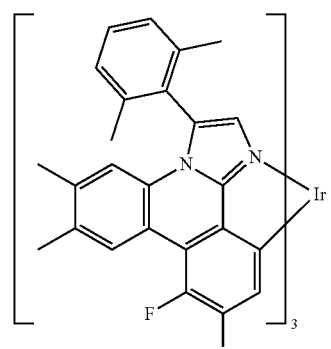
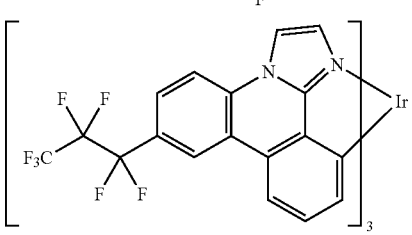
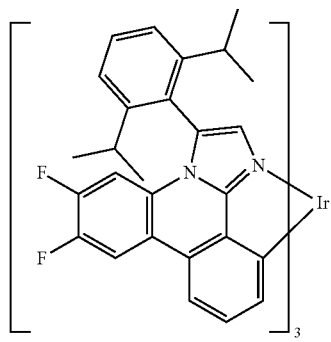
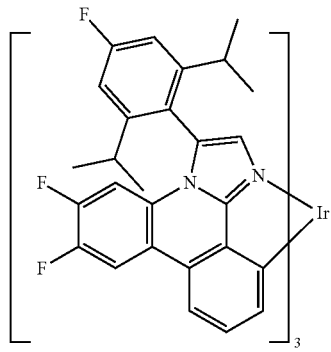
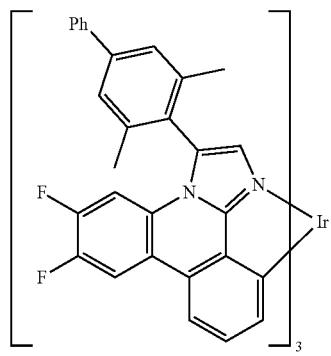

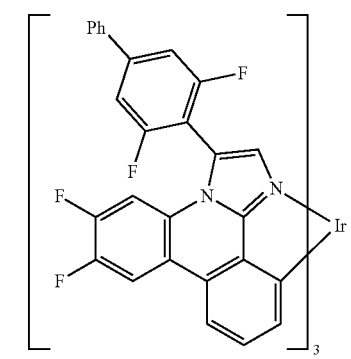
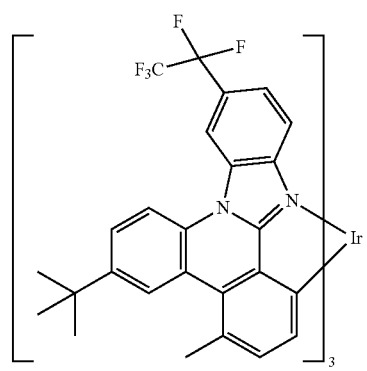
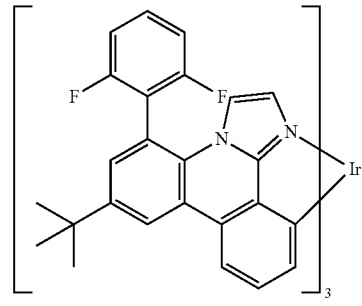
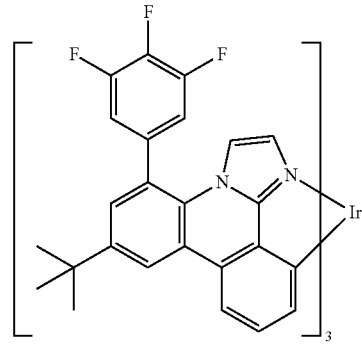
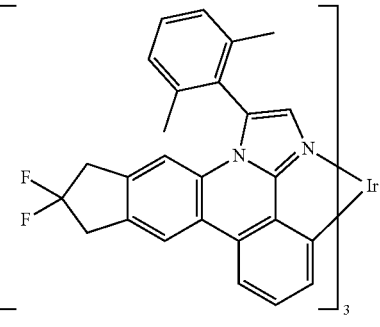
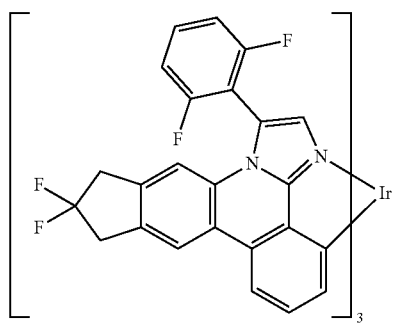
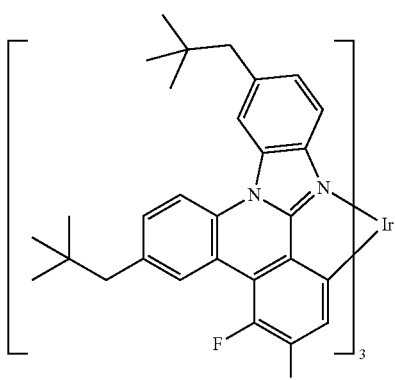
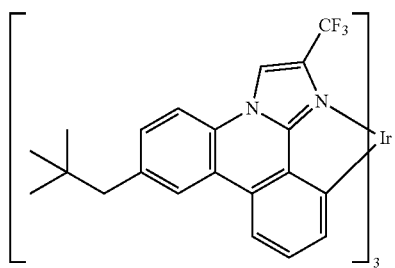
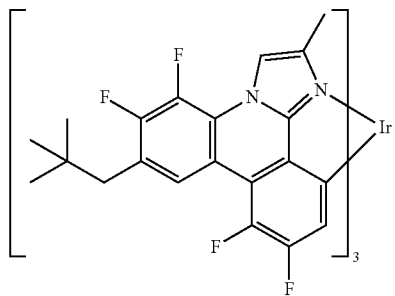
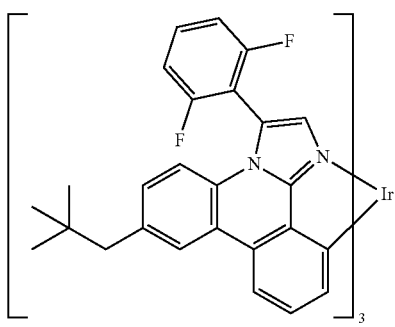

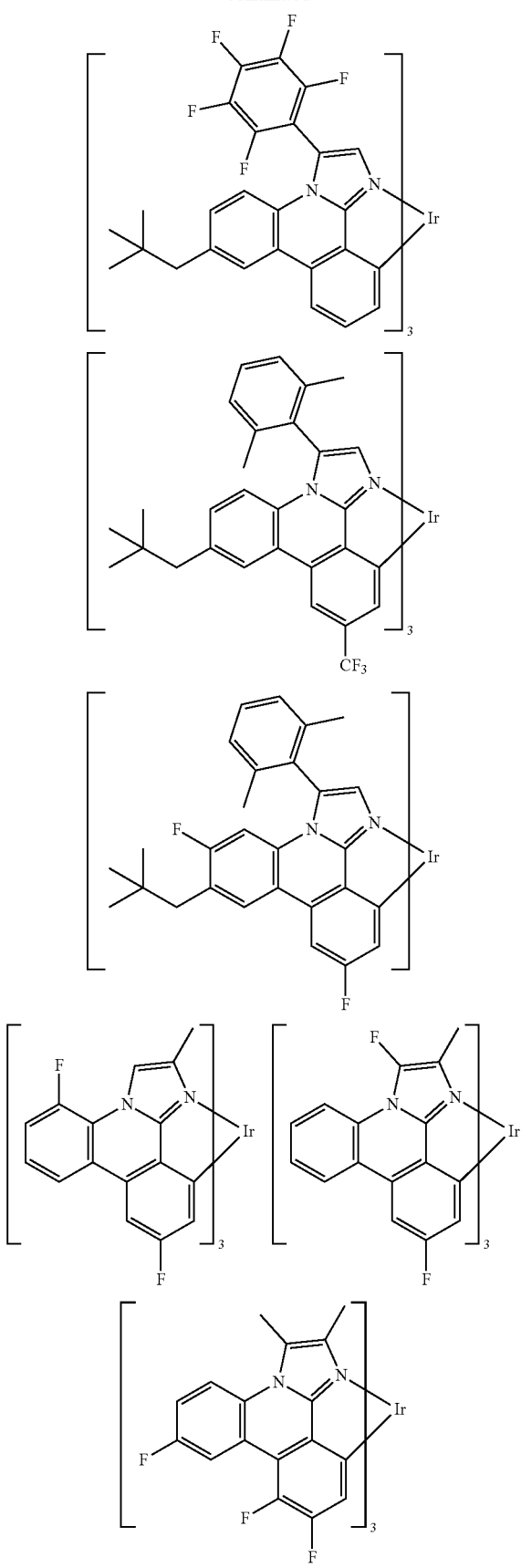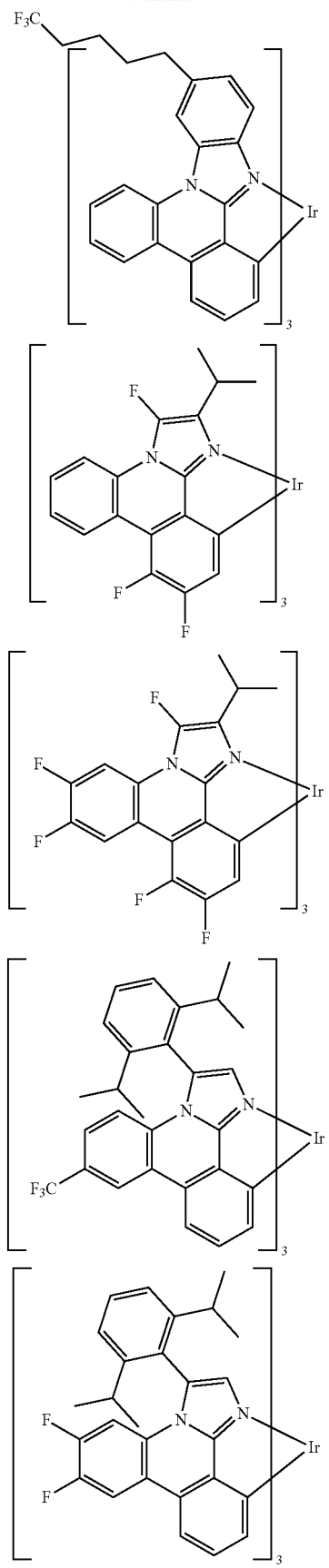

-continued
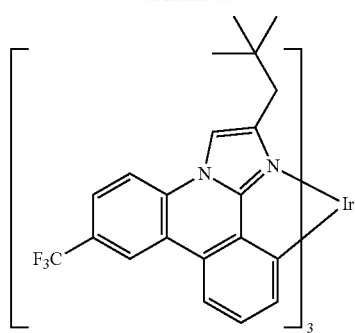
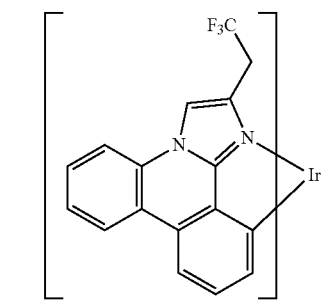
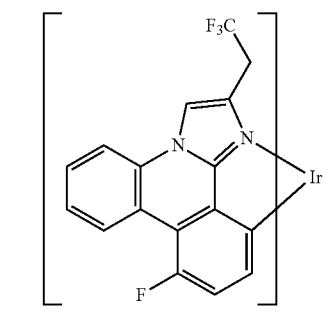
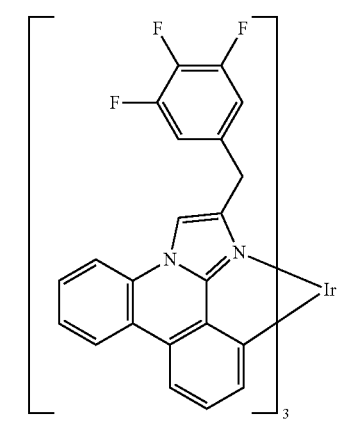
-continued
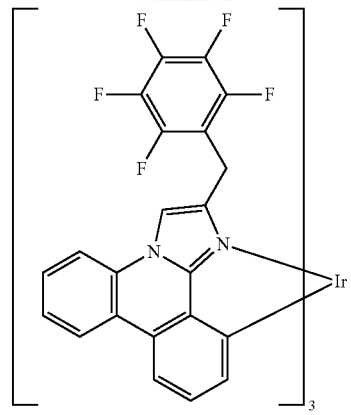
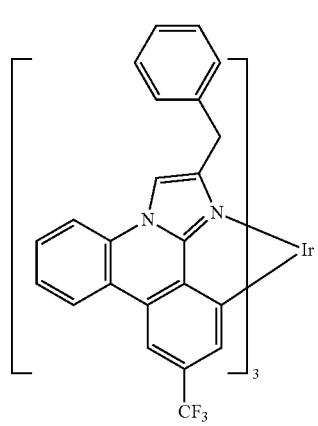
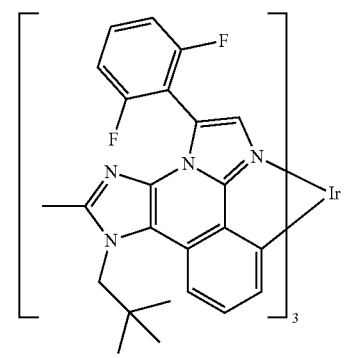
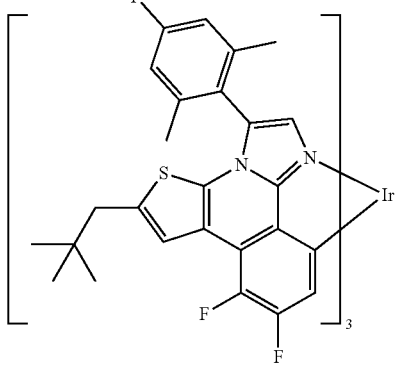

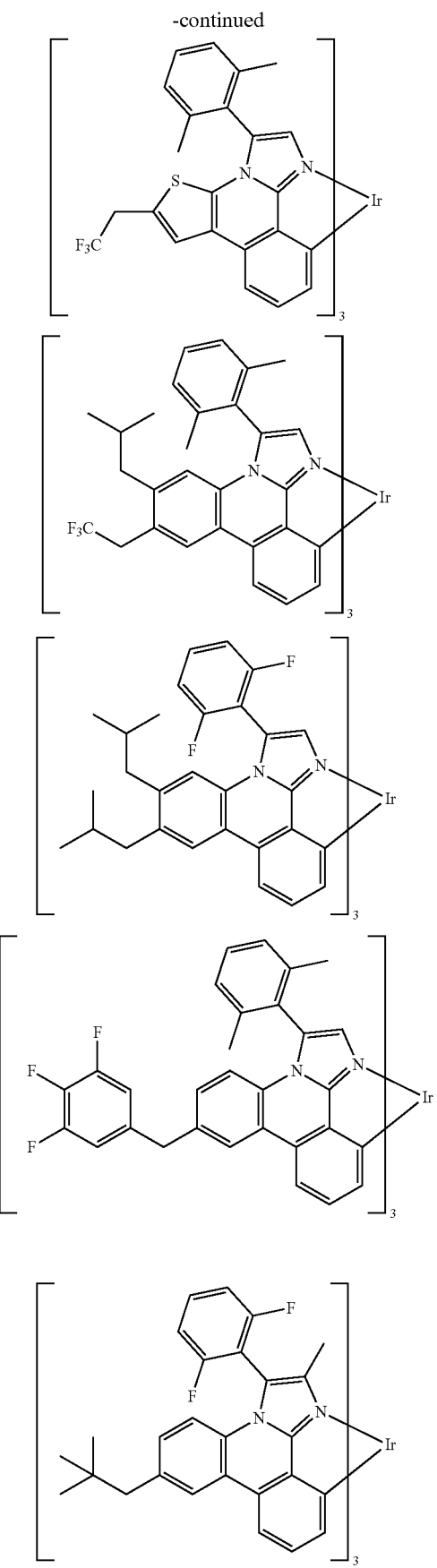
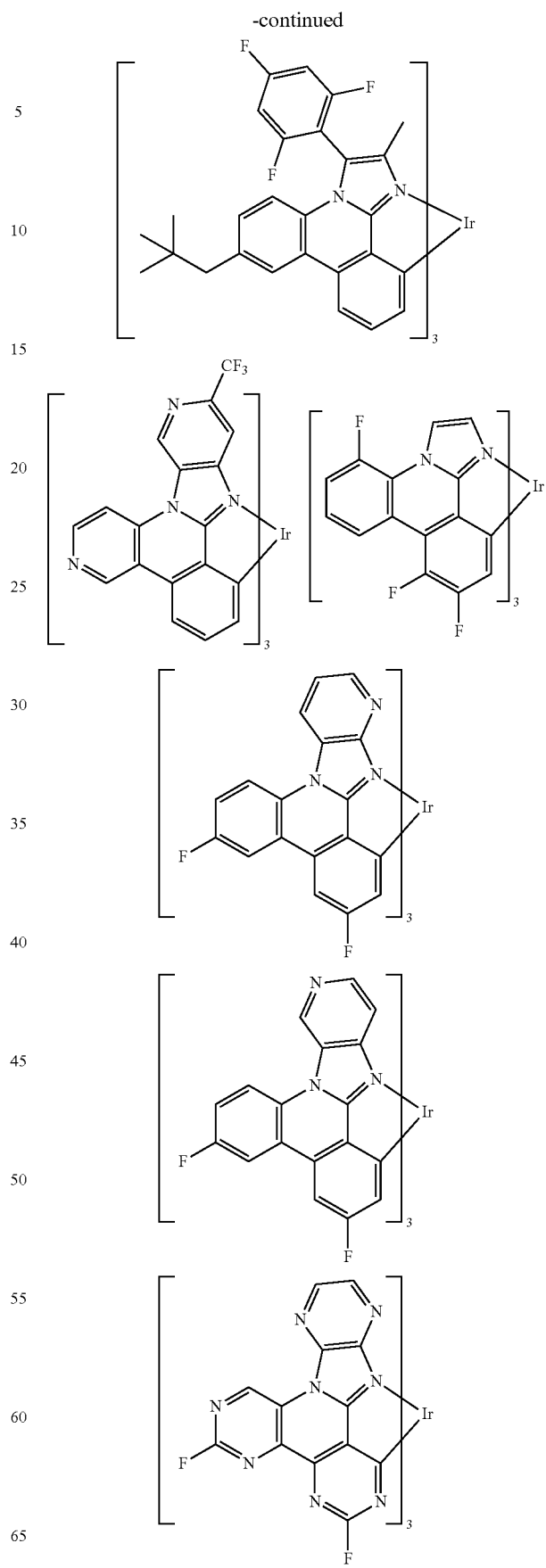

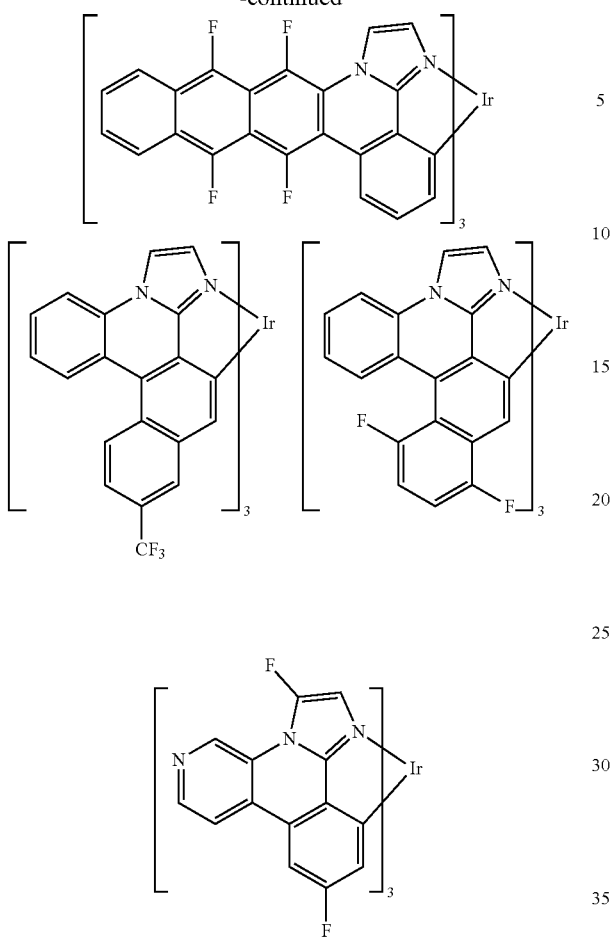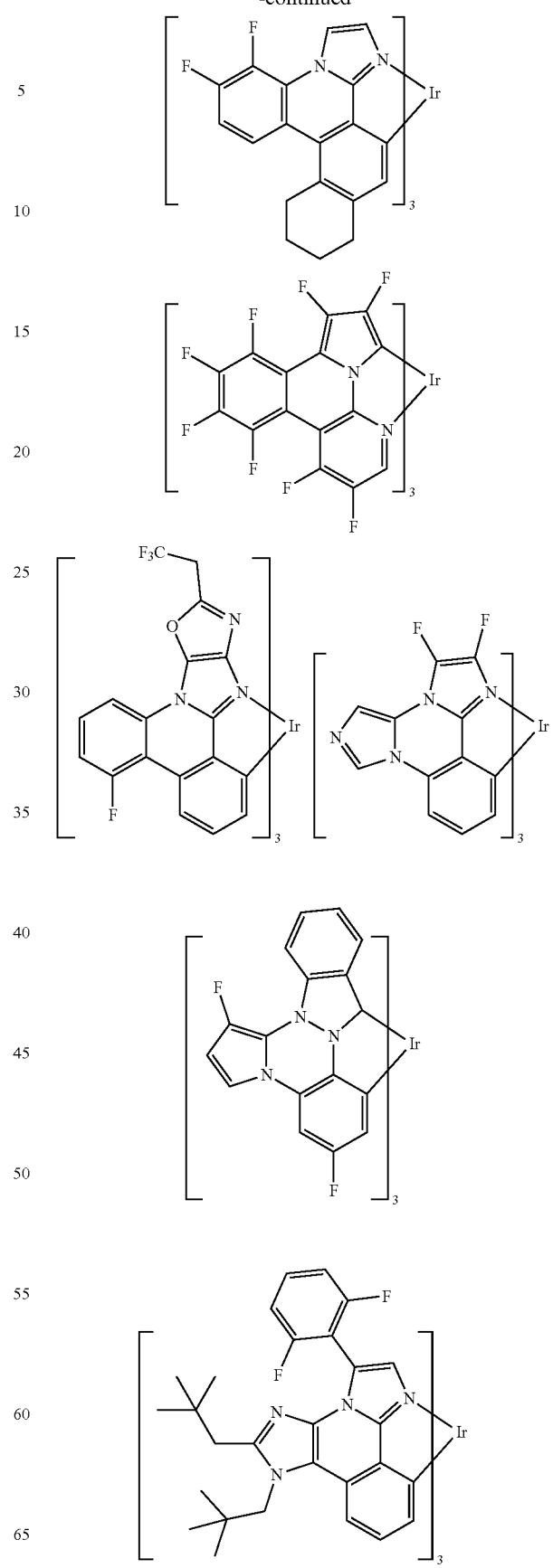

49
-continued
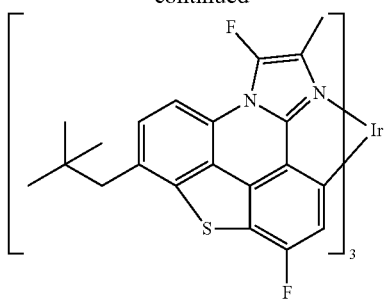
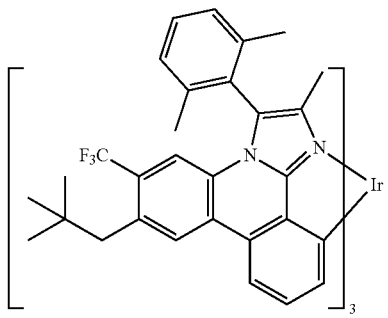
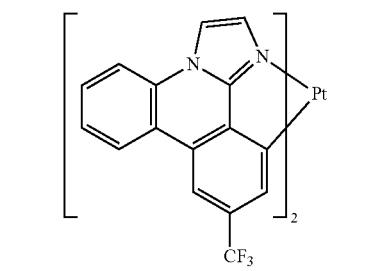
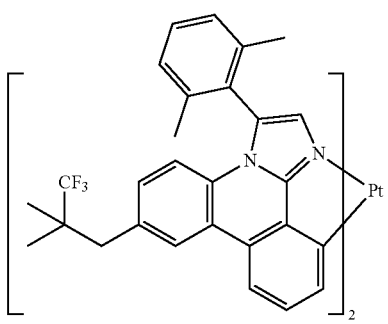
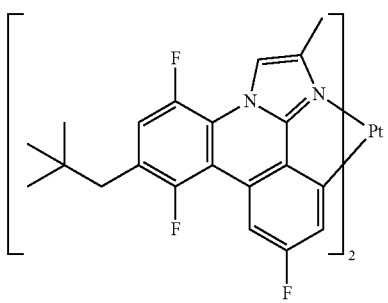
50
-continued
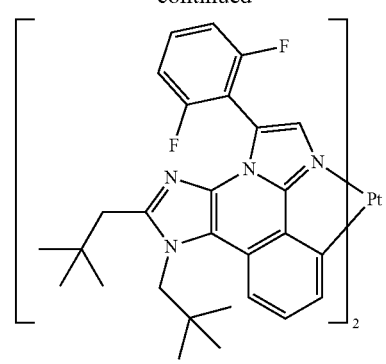
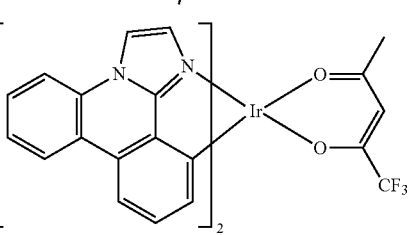
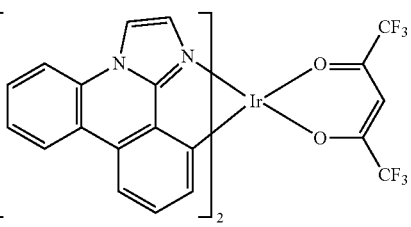
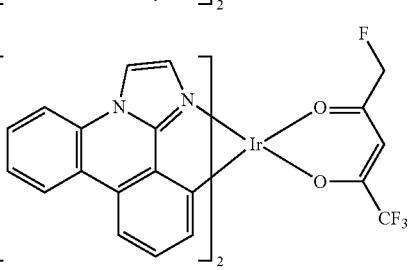
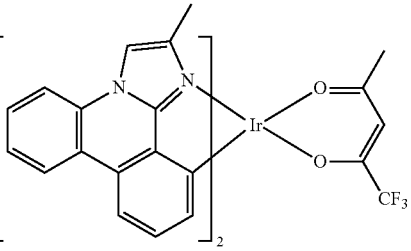
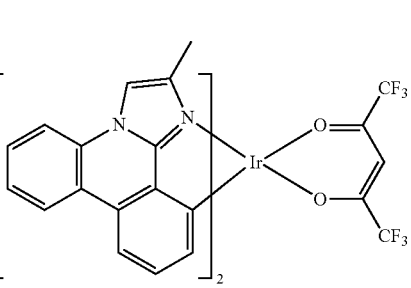

51
-continued
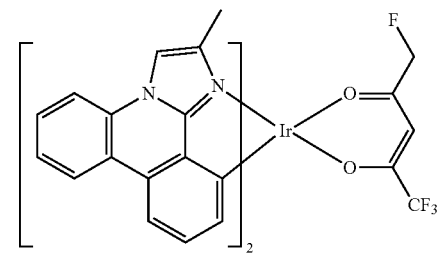
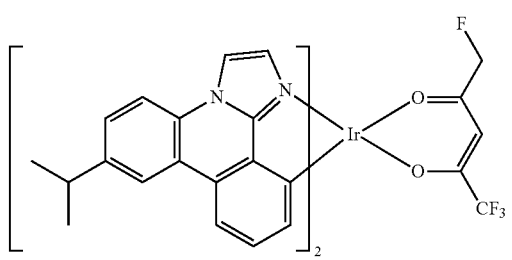
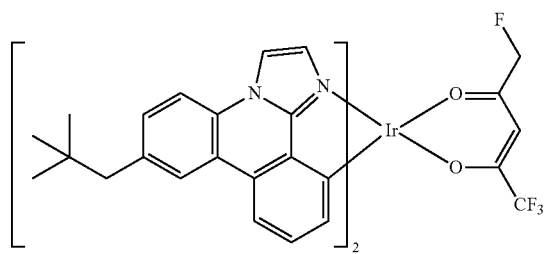
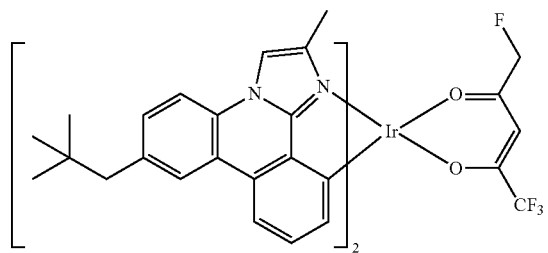
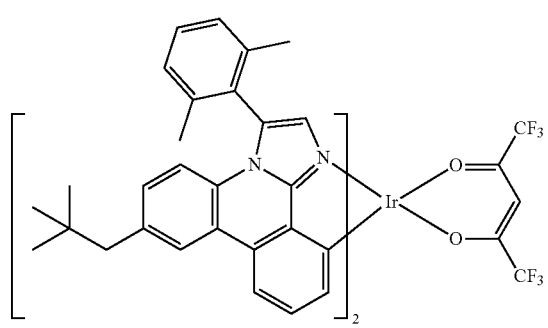
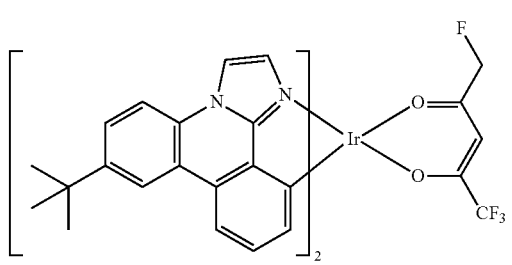
52
-continued
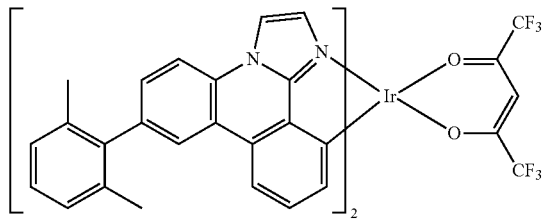
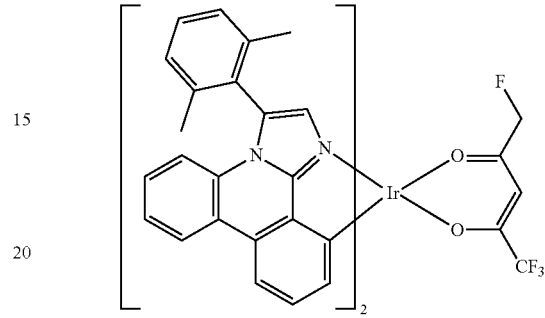
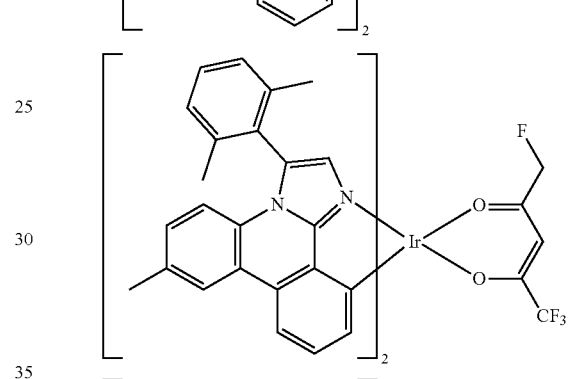
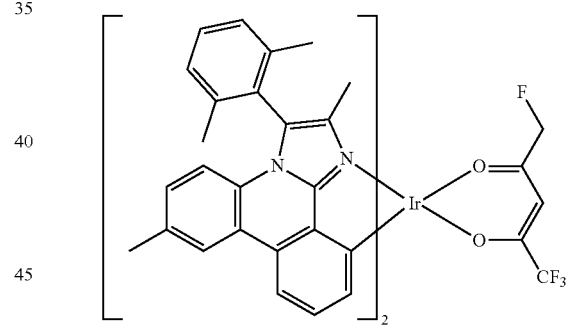
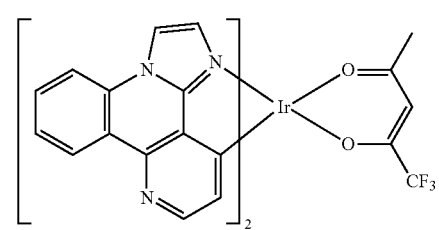
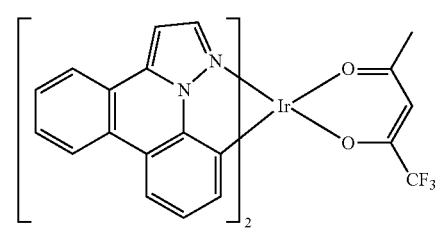

-continued
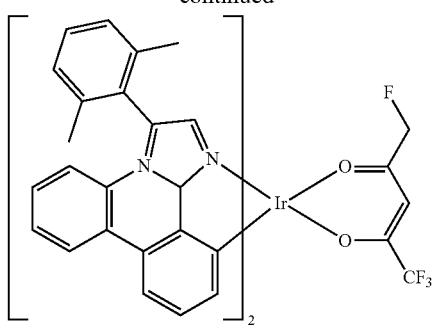
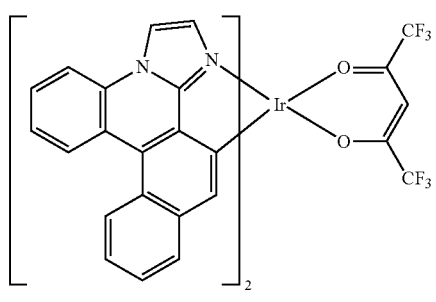
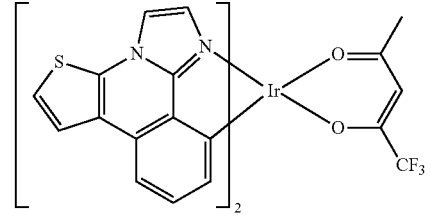
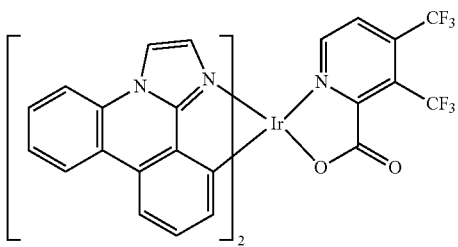
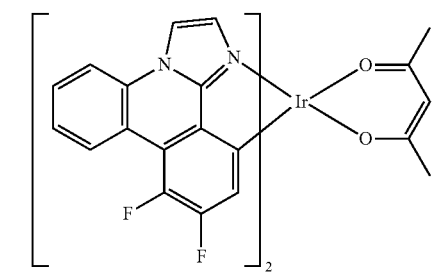
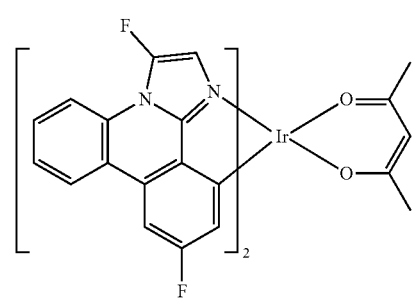
-continued
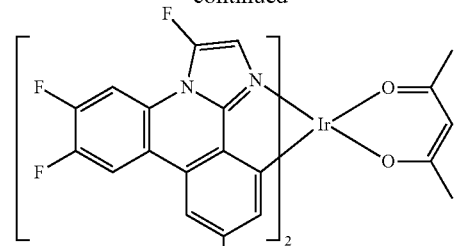
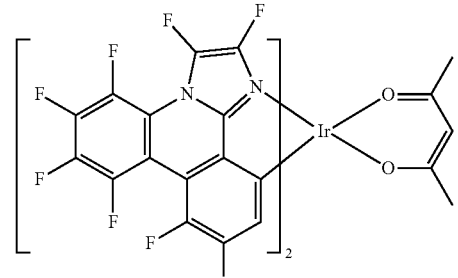
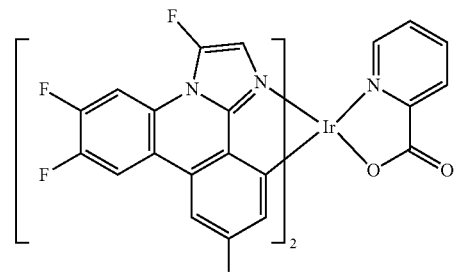
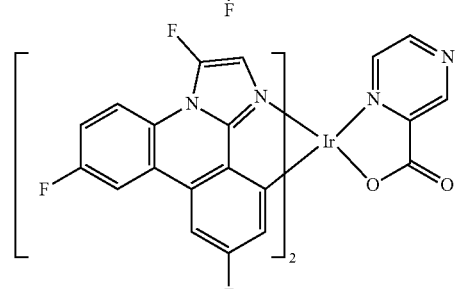
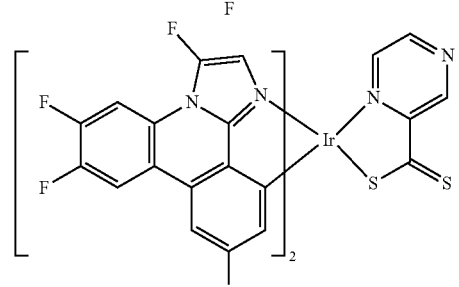
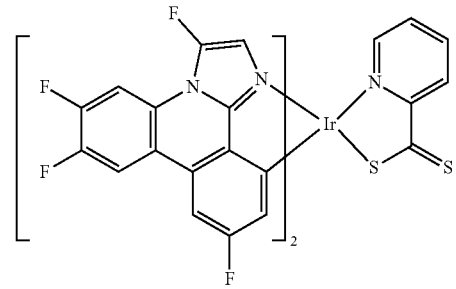

-continued

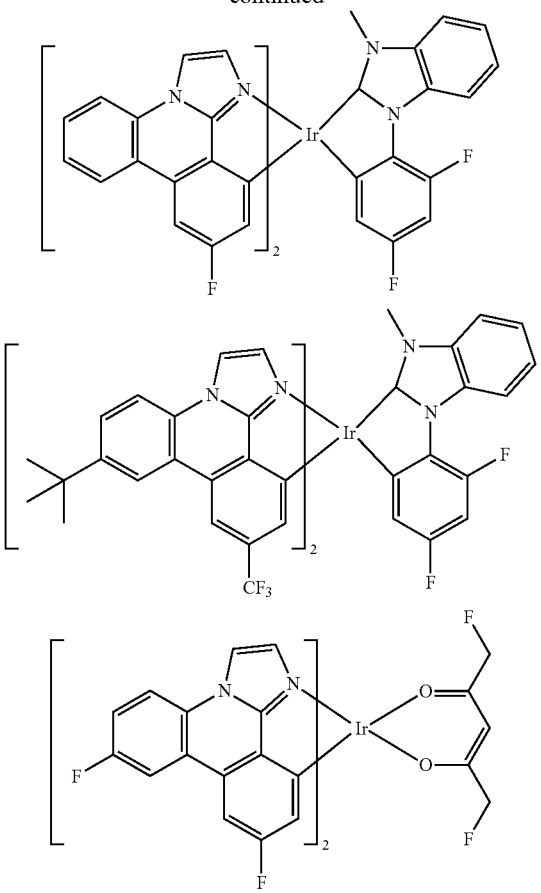

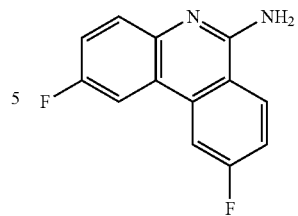

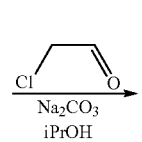

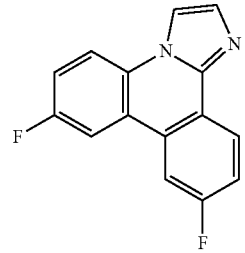

The phosphorescent metal complex containing a monoanionic bidentate ligand represented by the formula (A1-1) or (A3-1) and a metal having an atomic weight of 40 or more can be synthesized by reference to the methods disclosed in, for example, US2007/0190359 and US2008/0297033, and the like.

For example, the phosphorescent metal complex can be obtained by a reaction of a ligand or a dissociated material thereof and a metal compound in the absence or presence of a solvent (for example, alkane based solvents, benzene based solvents, halogen based solvents, alcohol based solvents, ether based solvents, ester based solvents, ketone based solvents, nitrile based solvents, amide based solvents, sulfone based solvents, sulfoxide based solvents, water, etc.) and in the absence or presence of a base (various inorganic or organic bases, for example, sodium methoxide, t-butoxypotassium, triethylamine, potassium carbonate, etc.) at a temperature of not higher than room temperature or by heating (besides usual heating, a heating technique with a microwave is also effective). Also, the ligand represented by the formula (A1-1) or (A3-1) can be synthesized by replacing raw materials disclosed in the foregoing patent documents by various fluorinated materials. Examples of the fluorinated material which is useful for the synthesis of the ligand include fluorinated aniline, fluorinated aryl boric acids and fluorinated aryl boric acid esters. For example, the ligand can be similarly synthesized using the following intermediate by reference to US-A-2008/297033, page 56, paragraph 133.

Also, it is preferable that the complex is used for a device upon sublimation purification.

[Organic Electroluminescence Device]

The organic electroluminescence device of the invention is described in detail.

The organic electroluminescence device of the invention is an organic electroluminescence device comprising a substrate having thereon a pair of electrodes and at least one layer of organic layers containing a light emitting layer between the electrodes, wherein at least one layer of the organic layers contains a phosphorescent metal complex containing a monoanionic bidentate ligand represented by the foregoing formula (A1-1) or formula (A3-1) and a non-radiative metal having an atomic weight of 40 or more and having a content of the fluorine atom of 7% by mass or more.

The organic electroluminescence device of the invention preferably contains the foregoing specified phosphorescent metal complex in the light emitting layer.

In the nature of the luminescence device, it is preferable that at least one electrode of an anode and a cathode is transparent or translucent.

FIG. 1 shows an example of a constitution of the organic electroluminescence device according to the invention. In an organic electroluminescence device 10 according to the invention as shown in FIG. 1, a light emitting layer 6 is interposed between an anode 3 and a cathode 9 on a supporting substrate 2. Specifically, a hole injection layer 4, a hole transport layer 5, the light emitting layer 6, a hole blocking layer 7 and an electron transport layer 8 are laminated in this order between the anode 3 and the cathode 9.

<Constitution of Organic Layer>

The layer constitution of the organic layer is not particularly limited and can be properly selected depending upon an application and a purpose of the organic electroluminescence device. However, it is preferable that the organic layer is formed on the foregoing transparent electrode or the foregoing back electrode. In that case, the organic layer is formed entirely or partially on the foregoing transparent electrode or the foregoing back electrode.

The organic layer is not particularly limited with respect to its shape, size and thickness and so on and may be properly selected depending upon its purpose.

Specific examples of the layer constitution are enumerated below, but it should not be construed that the invention is limited thereto.

Anode/hole transport layer/light emitting layer/electron transport layer/cathode Anode/hole transport layer/light emitting layer/blocking layer/electron transport layer/cathode Anode/hole transport layer/light emitting layer/blocking layer/electron transport layer/electron injection layer/cathode Anode/hole injection layer/hole transport layer/light emitting layer/blocking layer/electron transport layer/cathode Anode/hole injection layer/hole transport layer/light emitting layer/blocking layer/electron transport layer/electron injection layer/cathode The device constitution, substrate, cathode and anode of the organic electroluminescence device are described in detail in, for example, JP-A-2008-270736, and the matters disclosed in this patent document can be applied to the invention.

<Substrate>

It is preferable that the substrate which is used in the invention is a substrate which does not scatter or decay light emitted from the organic layer. In the case of an organic material, it is preferable that the organic material is excellent in heat resistance, dimensional stability, solvent resistance, electric insulating properties and processability.

<Anode>

In general, the anode may have a function as an electrode for feeding a hole into the organic layer. The anode is not particularly limited with respect to its shape, structure and size and so on and can be properly selected among known electrode materials depending upon an application and a purpose of the luminescence device. As described previously, the anode is usually provided as a transparent anode.

<Cathode>

In general, the cathode may have a function as an electrode for injecting an electron into the organic layer. The cathode is not particularly limited with respect to its shape, structure and size and so on and can be properly selected among known electrode materials depending upon an application and a purpose of the luminescence device.

With respect to the substrate, the anode and the cathode, the matters disclosed in JP-A-2008-270736, paragraphs [0070] to [0089] can be applied to the invention.

<Organic Layer>

The organic layer in the invention is described.

—Formation of Organic Layer—

In the organic electroluminescence device of the invention, each of the organic layers can be suitably formed by any of a dry film deposition method such as a vapor deposition method and a sputtering method, a transfer method or a printing method or the like.

(Light Emitting Layer)

<Light Emitting Material>

It is preferable that the light emitting material in the invention is the foregoing specified phosphorescent metal complex.

The light emitting material in the light emitting layer is generally contained in an amount of from 0.1% by mass to 50% by mass relative to the mass of all of the compounds capable of forming the light emitting layer in the light emitting layer. From the viewpoints of durability and external quantum efficiency, a content of the light emitting material is preferably from 1% by mass to 50% by mass, and more preferably from 2% by mass to 40% by mass.

From the viewpoints of durability and external quantum efficiency, a content of the specified phosphorescent metal complex in the light emitting layer is preferably from 1% by mass to 30% by mass, and more preferably from 5% by mass to 20% by mass in the light emitting layer.

Though a thickness of the light emitting layer is not particularly limited, in general, it is preferably from 2 nm to 500 nm. From the viewpoint of external quantum efficiency, the thickness of the light emitting layer is more preferably from 3 nm to 200 nm, and further preferably from 5 nm to 100 nm.

The light emitting layer in the device of the invention may be constituted of only a light emitting material, or may be constituted of a mixed layer of a host material and a light emitting material. The light emitting material may be a fluorescent material or a phosphorescent material, and a dopant may be made of a single kind or two or more kinds thereof. It is preferable that the host material is a charge transport material. The host material may be made of a single kind or two or more kinds thereof. For example, there is exemplified a constitution of a mixture of an electron transporting host material and a hole transporting host material. Furthermore, a material which does not have charge transporting properties and which does not undergo light emission may be contained in the light emitting layer.

Also, the light emitting layer may be constituted of a single layer or multiple layers of two or more layers. Also, the respective light emitting layers may undergo light emission in a different luminescent color from each other.

<Host Material>

The following compounds may be contained as the host material which is used in the invention. That is, there can be exemplified pyrrole, indole, carbazoles (for example, CBP (4,4'-di(9-carbazoyl)biphenyl)), azaindole, azacarbazole, triazole, oxazole, oxadiazole, pyrazole, imidazole, thiophene, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin based compounds, polysilane based compounds, poly(N-vinylcarbazole), aniline based copolymers, thiophene oligomers, conductive high-molecular weight oligomers such as polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyrane dioxide, carbodiimide, fluorenylidenemethane, distyrylpyrazine, fluorine-substituted aromatic compounds, heterocyclic tetracarboxylic acid anhydrides such as naphthaleneperillene, phthalocyanine, metal complexes of an 8-quinolinol derivative, metal phthalocyanines, various metal complexes represented by metal complexes containing benzoxazole or benzothiazole as a ligand and derivatives thereof (may have a substituent or a condensed ring).

In the light emitting layer in the invention, from the standpoints of color purity, luminous efficiency and driving durability, it is preferable that the lowest excited triplet energy ($T_1$ energy) of the host material is higher than the $T_1$ energy of the phosphorescent material.

Also, though a content of the host compound in the invention is not particularly limited, from the viewpoints of luminous efficiency and driving voltage, it is preferably 15% by mass or more and not more than 95% by mass relative to the mass of all of the compounds capable of forming the light emitting layer.

It is preferable that the light emitting layer contains the phosphorescent metal complex containing a monoanionic bidentate ligand represented by the formula (A1-1) or formula (A3-1) and a non-radiative metal having an atomic weight of 40 or more and further the host material. Though the host material may be a hole transporting host material or may be an electron transporting host material, the hole transporting host material can be used.

In the invention, it is preferable that at least one of compounds represented by the formula (4-1) or (4-2) is contained as the host material.

A content of the compound represented by the formula (4-1) or (4-2) in the light emitting layer is preferably from 30 to 100% by mass, more preferably from 40 to 100% by mass, and especially preferably from 50 to 100% by mass. Also, in the case where the compound represented by the formula (4-1) or (4-2) is used in plural organic layers, it is preferable that the compound represented by the formula (4-1) or (4-2) is contained in an amount falling within the foregoing range in each of the layers.

Only one kind of the compound represented by the formula (4-1) or (4-2) may be contained in any one organic layer; and a combination of plural kinds of the compound represented by the formula (4-1) or (4-2) in an arbitrary proportion may be contained.

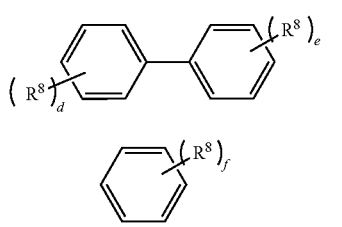

(4-1)

(4-2)

In the formulae (4-1) and (4-2), each of d and e represents an integer of from 0 to 3, and at least one of them is 1 or more; f represents an integer of from 1 to 4; $R^8$ represents a substituent; when each of d, e and f is 2 or more, each $R^8$ may be the same as or different from every other $R^8$; and at least one of $R^8$s represents a carbazole group represented by the following formula (5).

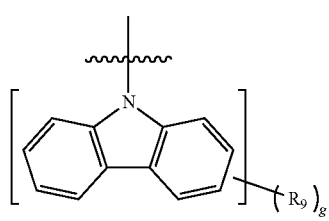

(5)

In the formula (5), each of $R_9$s independently represents a substituent; and g represents an integer of from 0 to 8.

Each of $R^8$s independently represents a substituent, and specifically, it is a halogen atom, an alkoxy group, a cyano group, a nitro group, an alkyl group, an aryl group, a heterocyclic group or the substituent represented by the formula (5). In the case where $R^8$ does not represent the formula (5), $R^8$ is preferably an alkyl group having not more than 10 carbon atoms or a substituted or unsubstituted aryl group having not more than 10 carbon atoms, and more preferably an alkyl group having not more than 6 carbon atoms.

Each of $R_9$s independently represents a substituent, and specifically, it is a halogen atom, an alkoxy group, a cyano group, a nitro group, an alkyl group, an aryl group or a heterocyclic group, preferably an alkyl group having not more than 10 carbon atoms or a substituted or unsubstituted aryl group having not more than 10 carbon atoms, and more preferably an alkyl group having not more than 6 carbon atoms.

g represents an integer of from 0 to 8; and from the viewpoint that the carbazole structure bearing charge transport is not excessively blocked, g is preferably from 0 to 4. Also, from the viewpoint of easy synthesis, in the case where the carbazole has a substituent, it is preferable to have a substituent such that it is symmetrical about the nitrogen atom.

In the formula (4-1), from the viewpoint of keeping charge transport capability, the sum of d and e is preferably 2 or more. Also, it is preferable that $R^8$ is substituted at a meta-position against the other benzene ring. This is because in the ortho-substitution, a steric hindrance between the adjacent substituents to each other is large, and therefore, the bond is easily cleaved, and the durability becomes low. Also, in the para-substitution, the molecular shape becomes close to a rigid rod-like form, and crystallization is easy to take place, and therefore, device deterioration is easy to take place under a high-temperature condition. Specifically, it is preferable that the compound represented by the formula (4-1) is a compound represented by the following structure.

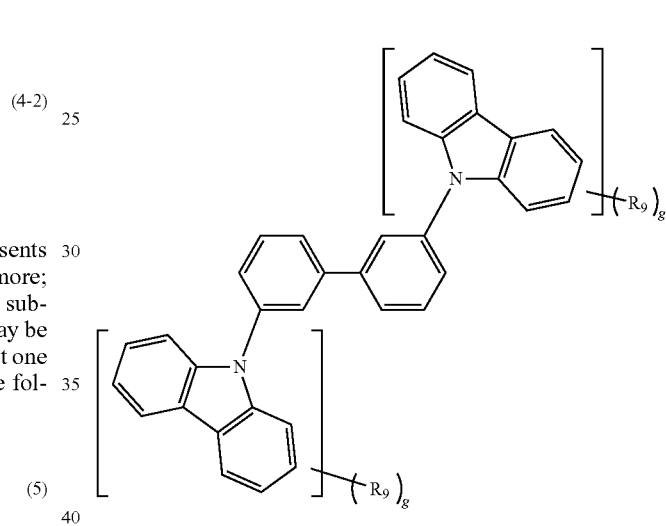

In the formula (4-2), from the viewpoint of keeping charge transport capability, f is preferably 2 or more. In the case where f is 2 or 3, from the same viewpoint, it is preferable that $R^8$s are substituted at the meta-position. Specifically, it is preferable that the compound represented by the formula (4-2) is a compound represented by the following structure.

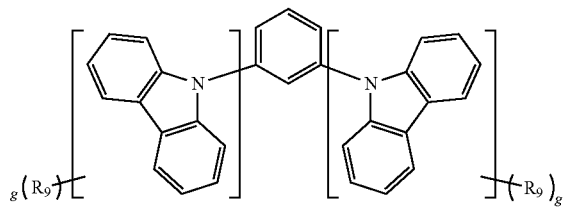

In the case where each of the formulae (4-1) and (4-2) has a hydrogen atom, there is included an isotope of hydrogen (for example, a deuterium atom, etc.). In that case, all of the hydrogen atoms in the compound may be replaced by an isotope of hydrogen. Also, the compound represented by each of the formulae (4-1) and (4-2) may be a mixture including a compound in which a part of the hydrogen atoms is an isotope of hydrogen. The compound represented by each of the formulae (4-1) and (4-2) is preferably a compound in which $R_9$ in the formula (5) is substituted with deuterium, and the following structures are especially preferable.

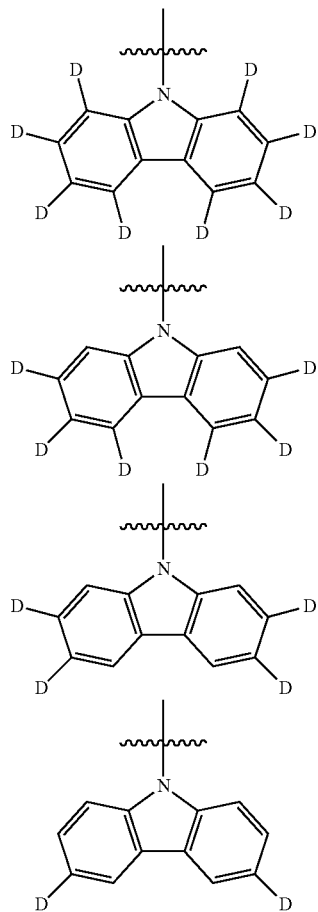

Furthermore, it is expressed that atoms constituting each substituent include isotopes thereof.

It is possible to synthesize the compound represented by each of the formulae (4-1) and (4-2) by a combination of various known synthesis methods.

Most generally, with respect to the carbazole compound, there is exemplified a synthesis by an Aza-Cope rearrangement reaction of a condensate of an aryl hydrazine and a cyclohexane derivative and subsequent dehydroaromatization (*Reactions and Syntheses: In the Organic Chemistry*, page 339, written by L. F. Tieze and Th. Eicher, translated by Takano and Ogasawara and published by Nankodo). Also, with respect to a coupling reaction of the obtained carbazole compound and a halogenated aryl compound using a palladium catalyst, there are exemplified the methods described in *Tetrahedron Letters*, Vol. 39, page 617 (1998), ibid, Vol. 39, page 2367 (1998) and ibid., Vol. 40, page 6393 (1999) and so on. The reaction temperature and the reaction time are not particularly limited, and conditions described in the foregoing documents can be applied. Also, with respect to some compounds including mCP, etc., commercially available compounds can be suitably used.

With respect to the compound represented by each of the formulae (4-1) and (4-2) according to the invention, though it is preferable to form a thin layer by a vacuum vapor deposition process, a wet process such as solution coating can also be suitably adopted. From the viewpoints of vapor deposition aptitude and solubility, a molecular weight of the compound represented by each of the formulae (4-1) and (4-2) is preferably not more than 2,000, more preferably not more than 1,200, and especially preferably not more than 800. Also, from the viewpoint of vapor deposition aptitude, when the molecular weight is too low, a vapor pressure is small, change from a gas phase to a solid phase does not take place, and it is difficult to form an organic layer. Therefore, the molecular weight of the compound represented by each of the formulae (4-1) and (4-2) is preferably 250 or more, and especially preferably 300 or more.

The compound represented by each of the formulae (4-1) and (4-2) is a compound having any one of the following structures or a compound obtained by substituting one or more hydrogen atoms thereof with a deuterium atom.

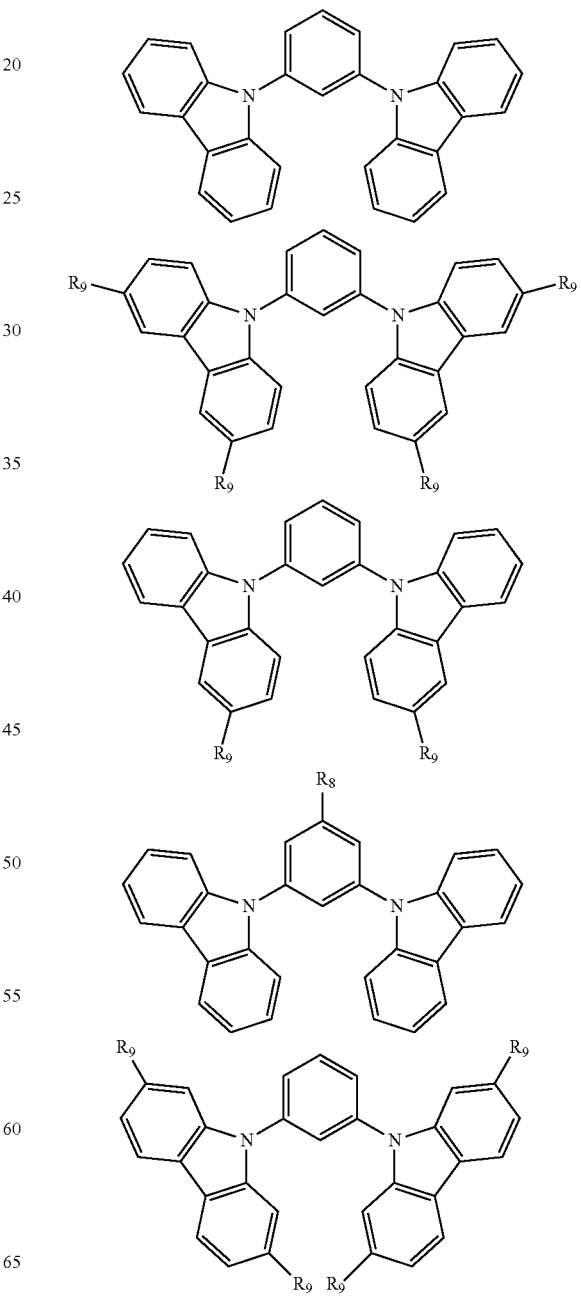

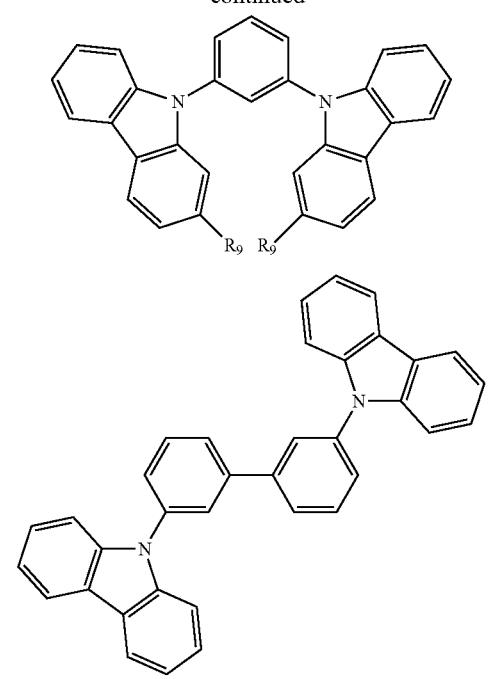
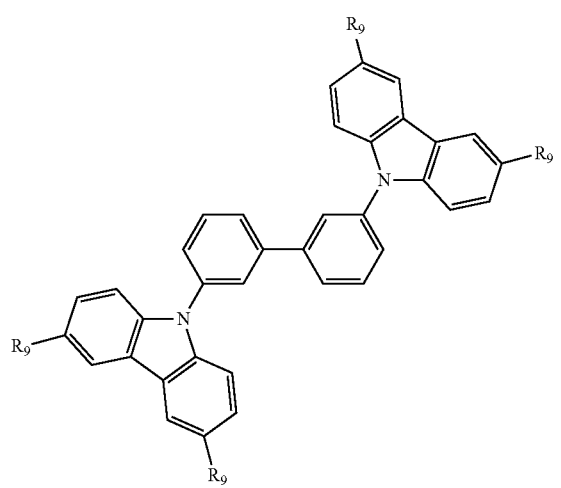
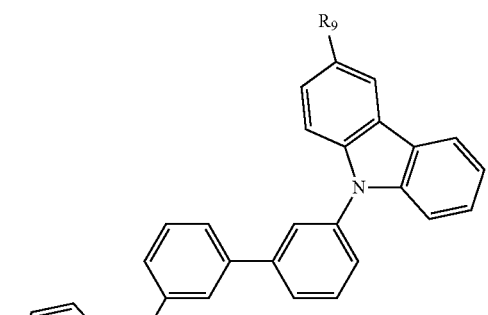
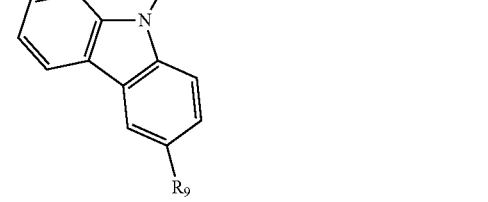
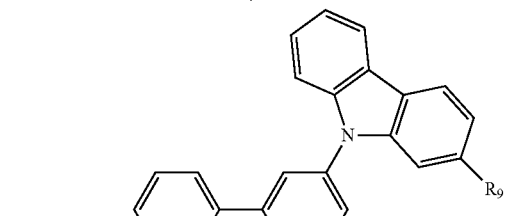
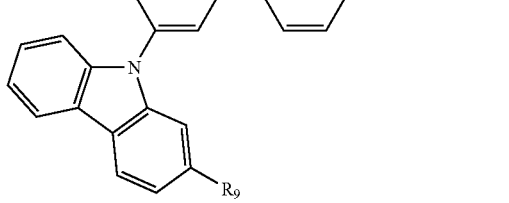
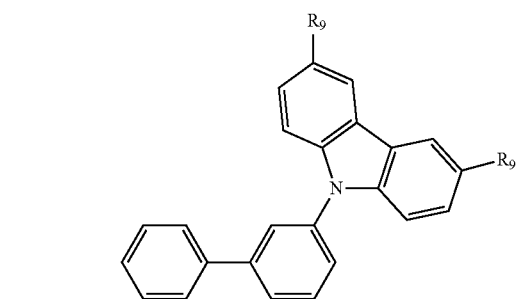
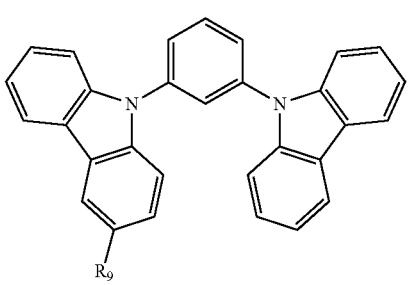

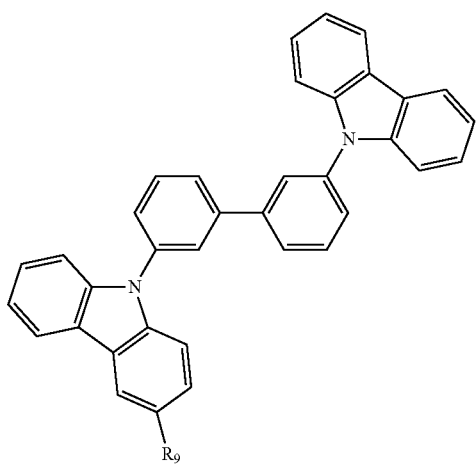
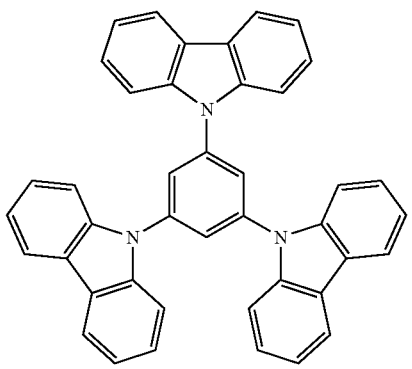
Specific examples of the compound represented by each of the formulae (4-1) and (4-2) in the invention are enumerated below, but it should not be construed that the invention is limited thereto.
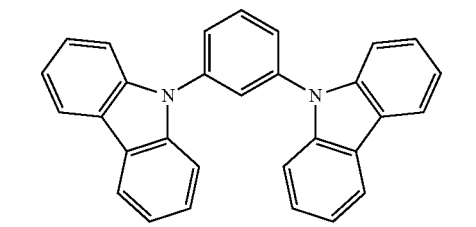
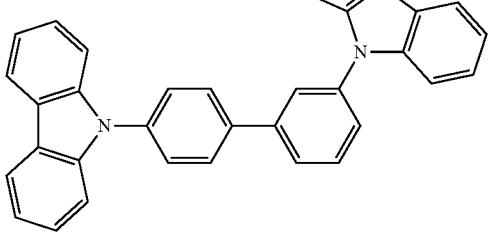
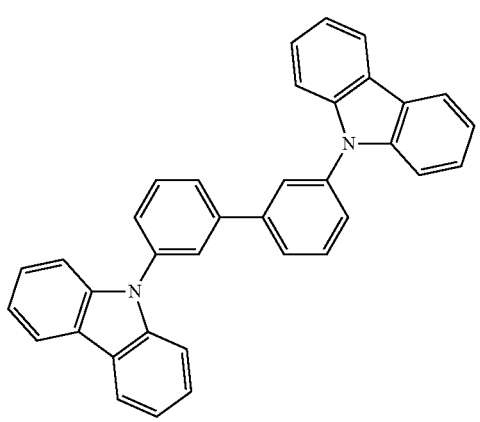
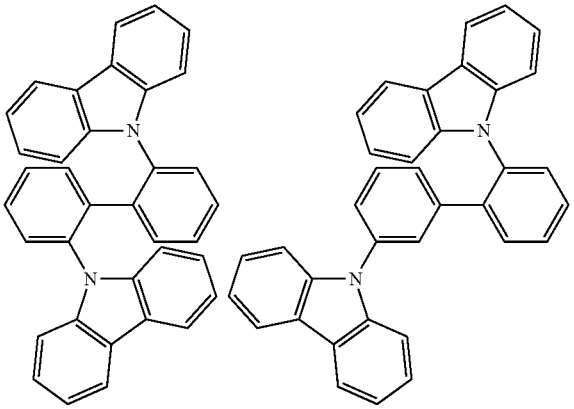
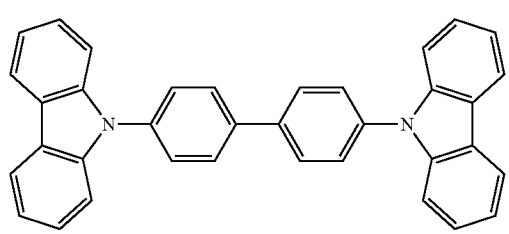
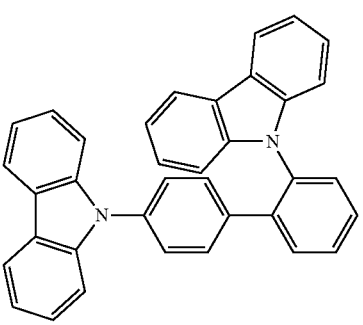

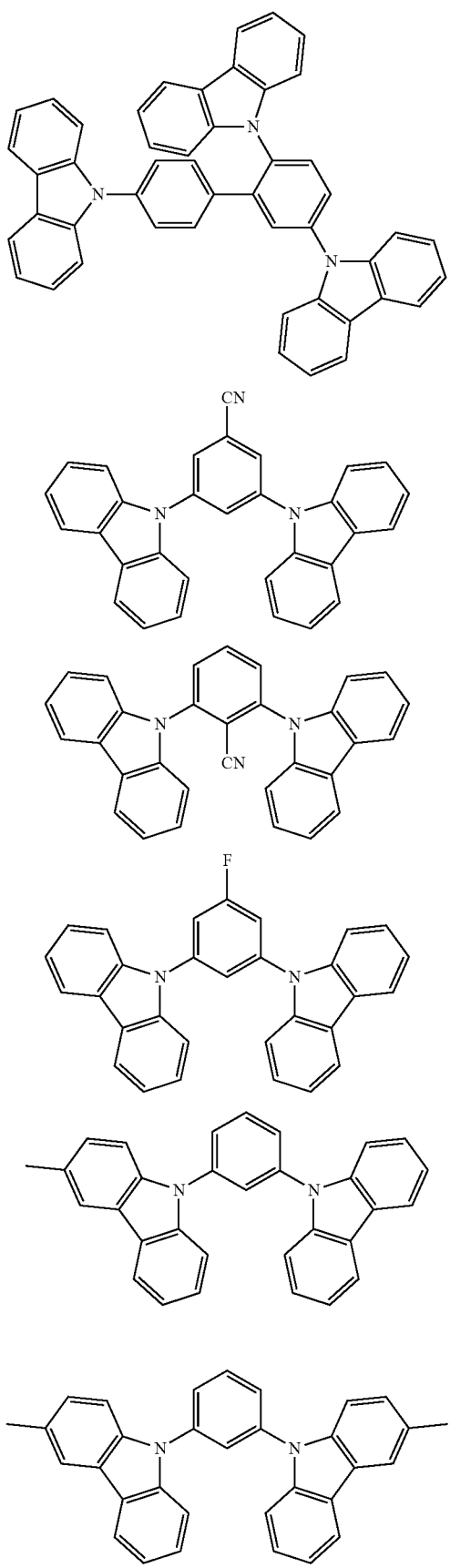
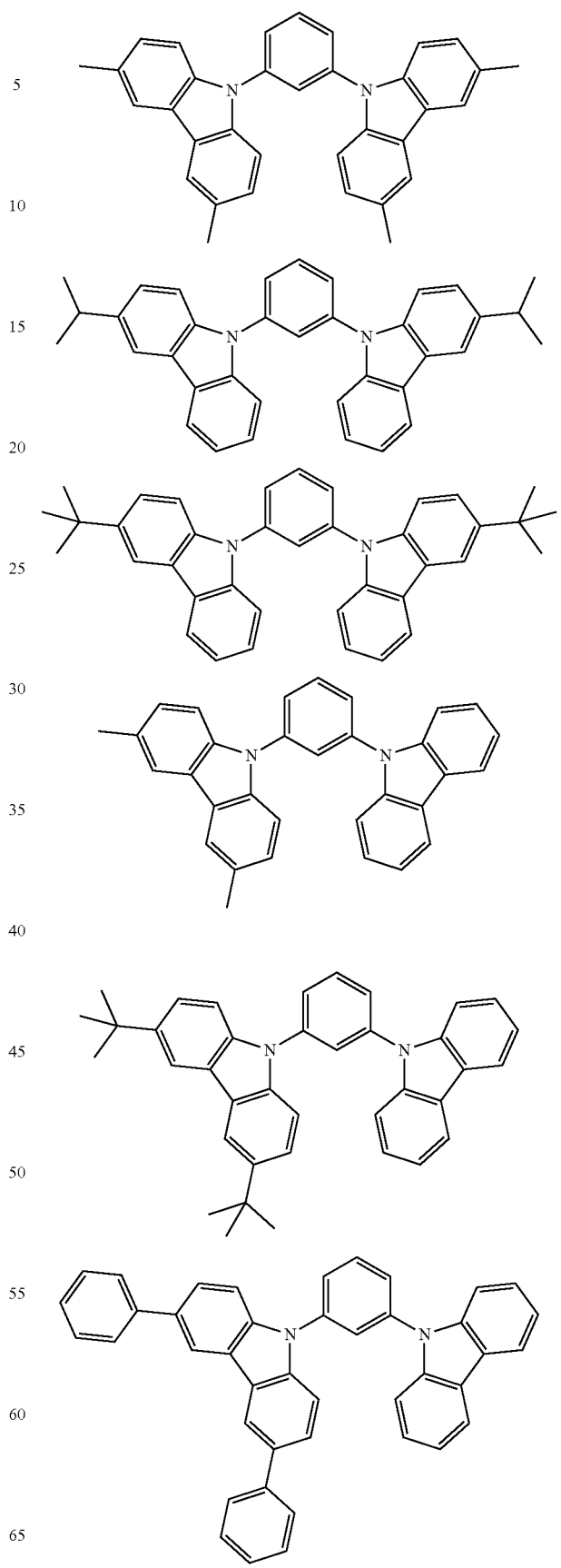

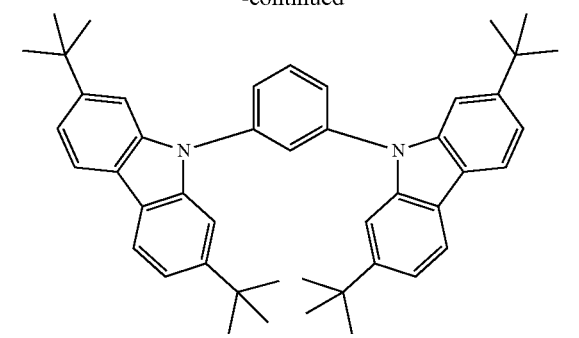
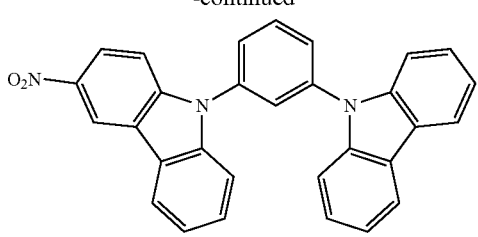
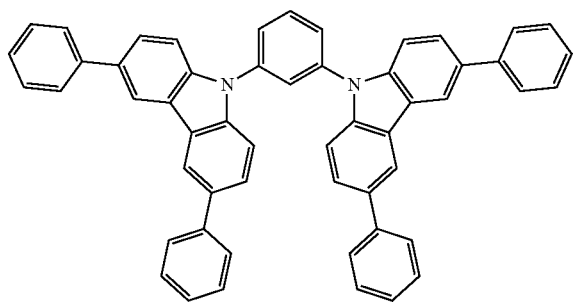
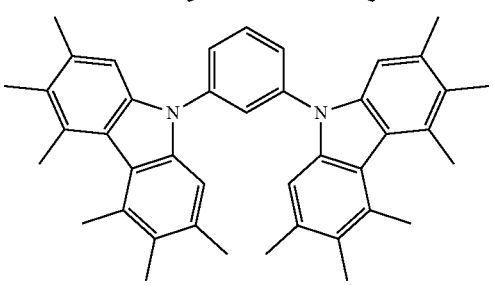
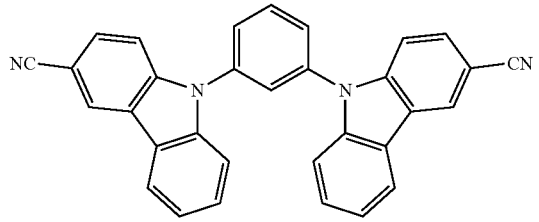
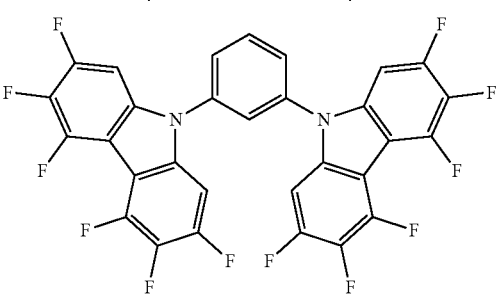
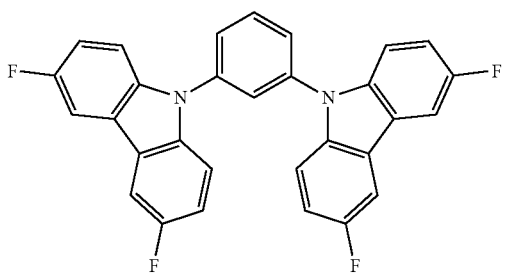
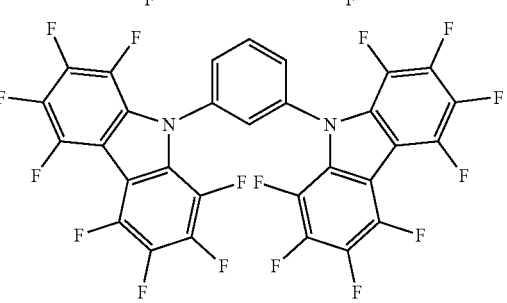
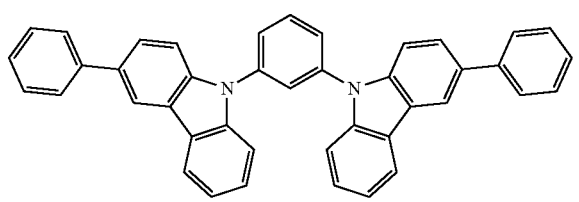
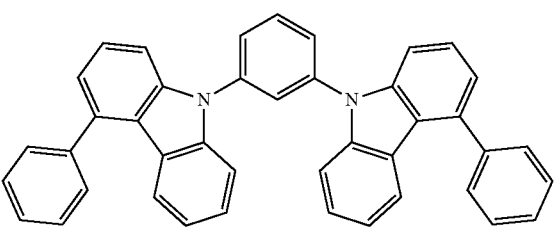
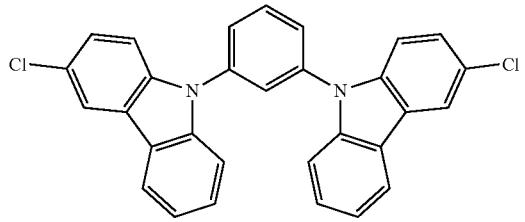
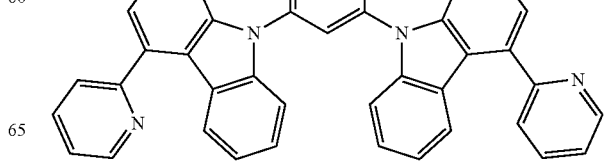

71
-continued
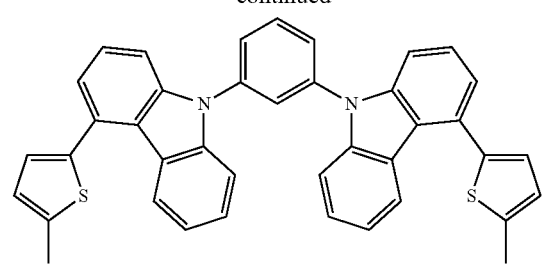
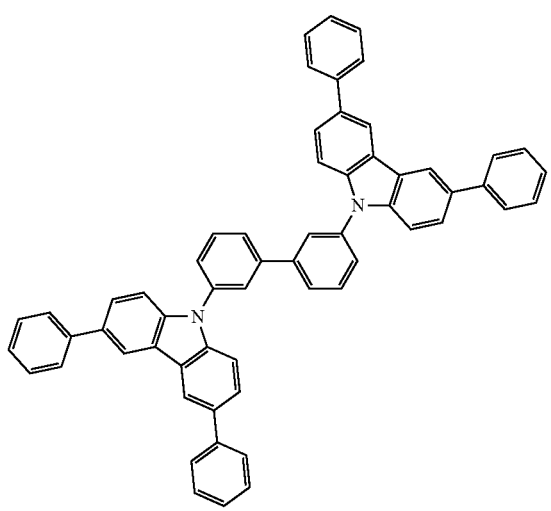
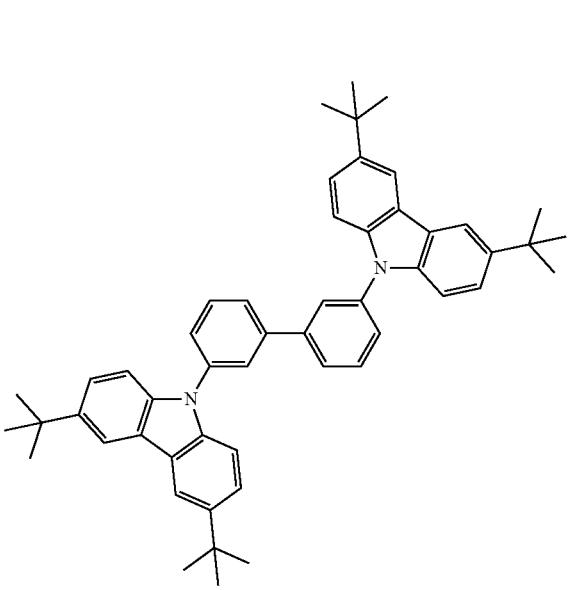
72
-continued
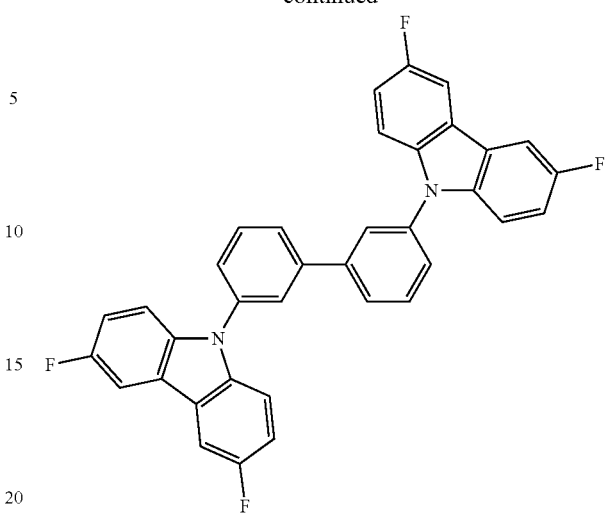
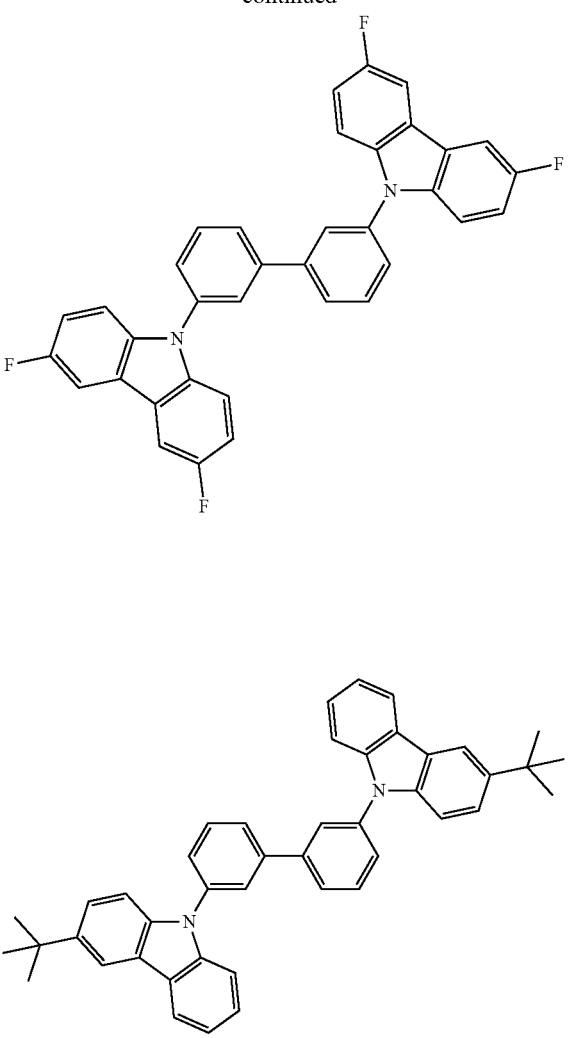
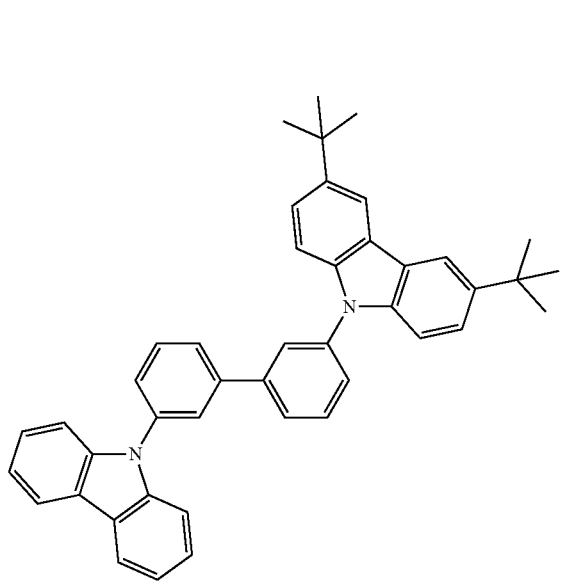

73
-continued
74
-continued
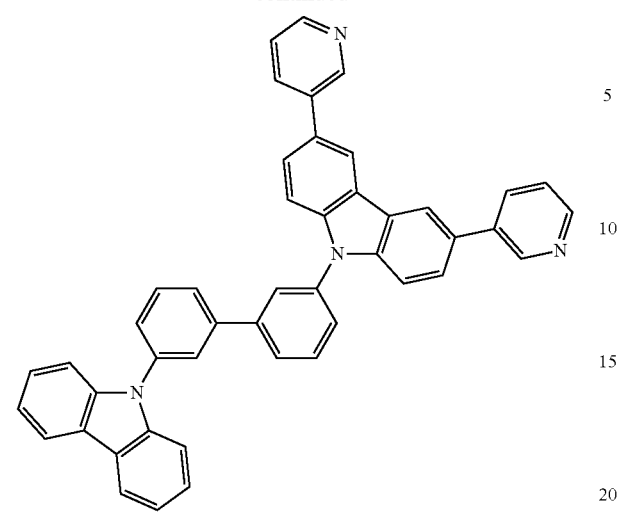
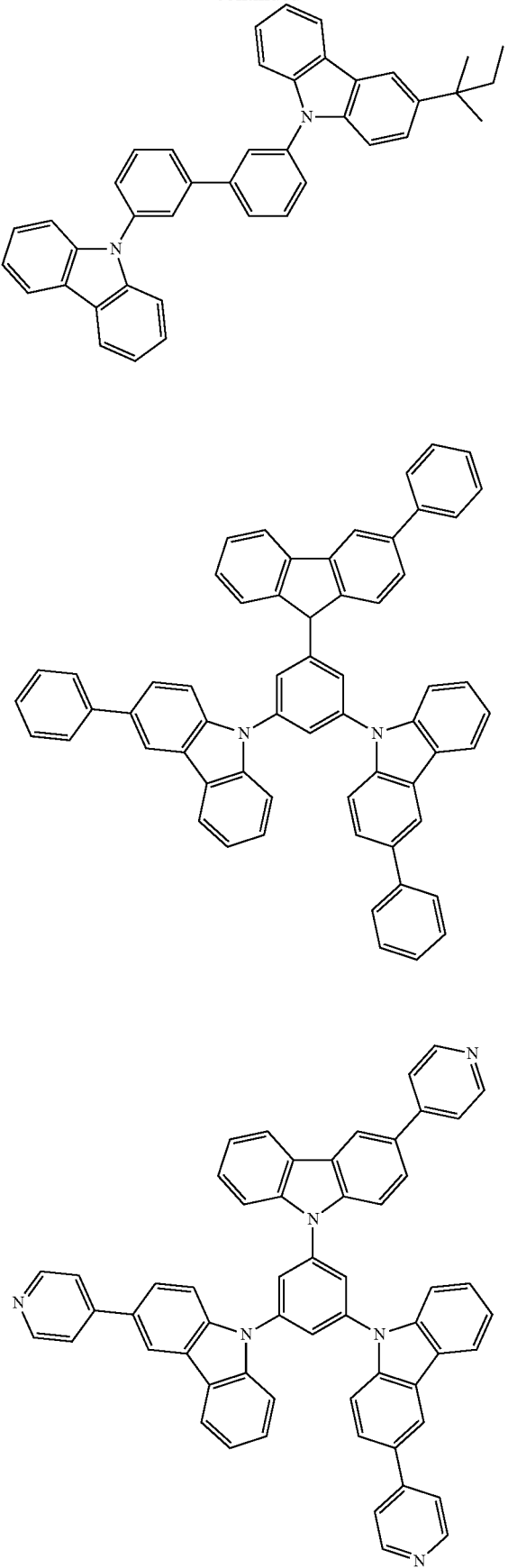

75
-continued
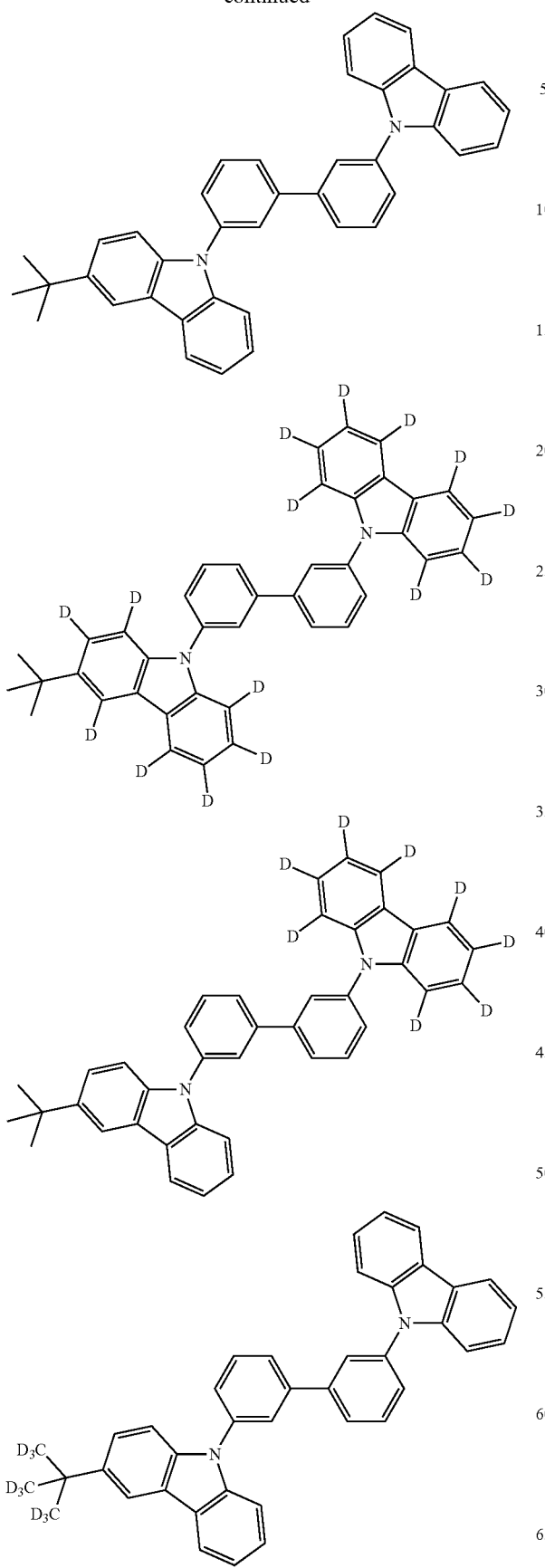
76
-continued
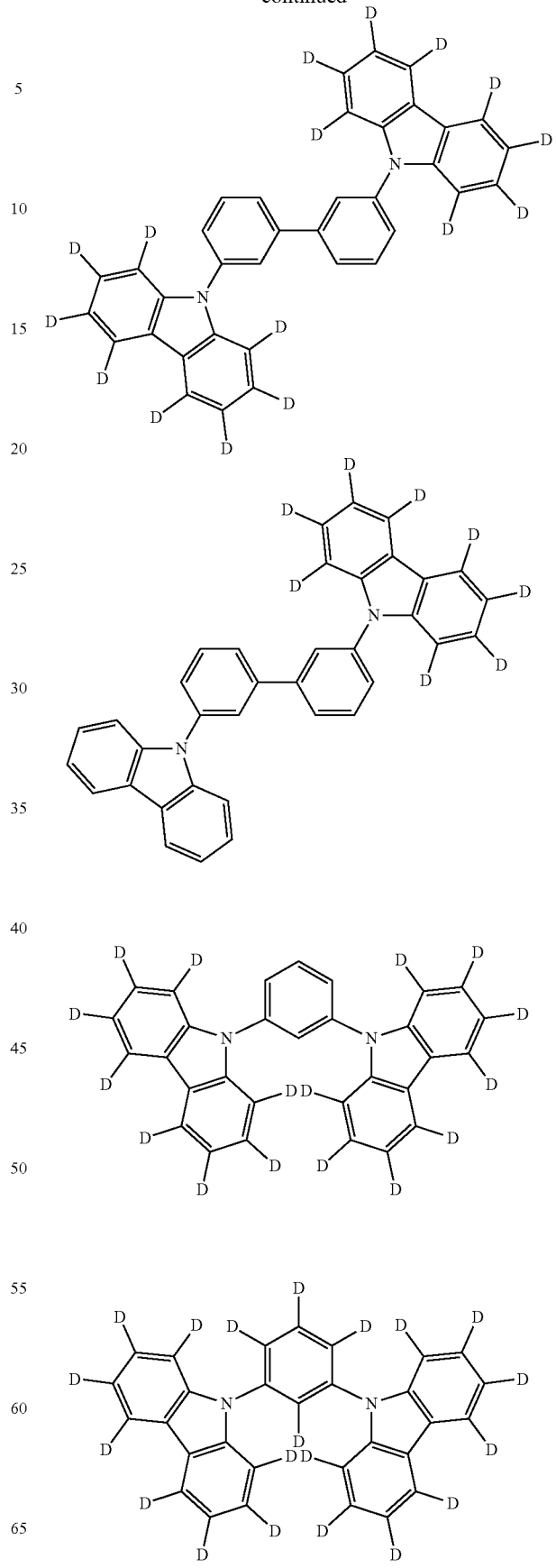

-continued

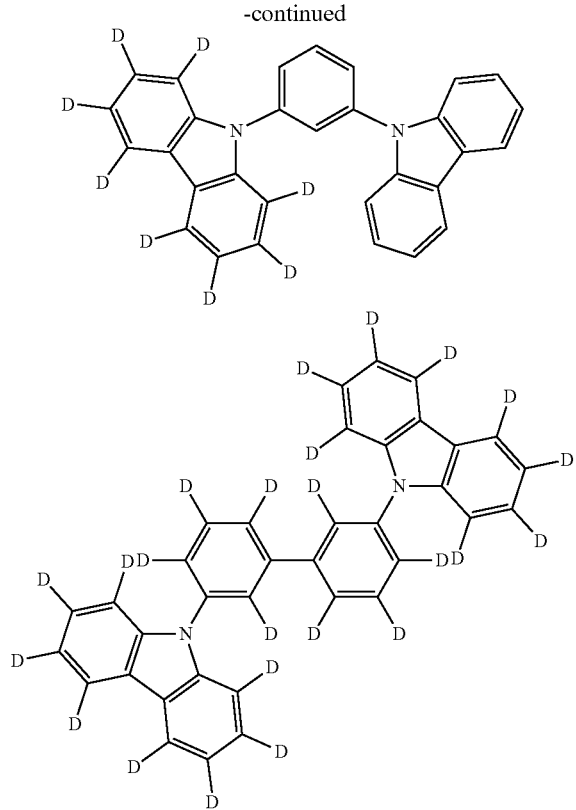

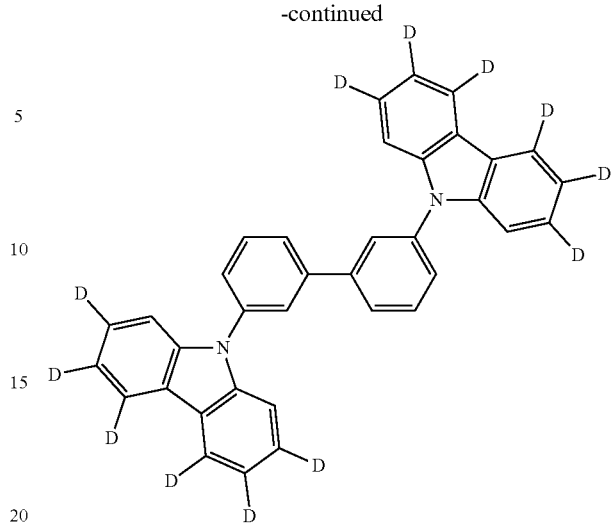

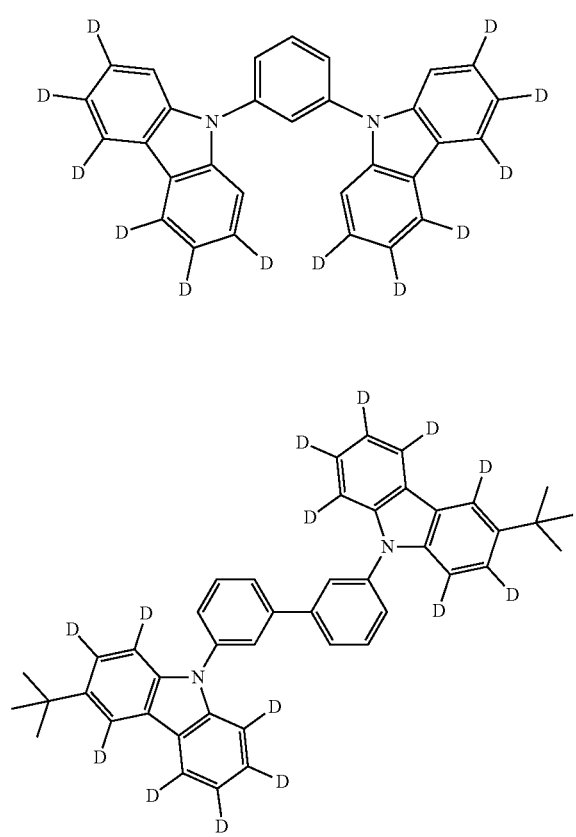

(Fluorescent Material)

Examples of the fluorescent material which can be used in the invention include compounds, for example, benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralizine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidine compounds, various complexes represented by complexes of 8-quinolinol derivatives and complexes of pyrromethene derivatives, polymer compounds such as polythiophene, polyphenylene and polyphenylene vinylene, organic silane derivatives, etc.

(Phosphorescent Material)

Examples of the phosphorescent material which can be used in the invention include phosphorescent compounds disclosed in patent documents, for example, U.S. Pat. No. 6,303,238B1, U.S. Pat. No. 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, JP-A-2007-96259, etc. Above all, more preferred examples of the light emitting dopant include Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes. In particular, Ir complexes, Pt complexes and Re complexes are preferable; and Ir complexes, Pt complexes and Re complexes each containing at least one coordination mode of a metal-carbon bond, a metal-nitrogen bond, a metal-oxygen bond and a metal-sulfur bond are more preferable. Furthermore, from the viewpoints of luminous efficiency, driving durability, chromaticity, etc., Ir complexes, Pt complexes and Re complexes each containing a tridentate or multidentate ligand are especially preferable.

A content of the phosphorescent material is preferably in the range of 0.1% by mass or more and not more than 50% by mass, more preferably in the range of 0.2% by mass or more and not more than 50% by mass, further preferably in the range of 0.3% by mass or more and not more than 40% by mass, and most preferably in the range of 20% by mass and not more than 30% by mass relative to the total mass of the light emitting layer.

A content of the phosphorescent material (the specified phosphorescent metal complex and/or the phosphorescent material to be jointly used) which can be used in the invention is preferably in the range of 0.1% by mass or more and not more than 50% by mass, more preferably in the range of 1% by mass or more and not more than 40% by mass, and most preferably in the range of 5% by mass and not more than 30% by mass relative to the total mass of the light emitting layer. In particular, when the content of the phosphorescent material is in the range of 5% by mass and not more than 30% by mass relative to the total mass of the light emitting layer, the chromaticity of light emission of the organic electroluminescence device is small with respect to the dependency on the addition concentration of the phosphorescent material.

In the organic electroluminescence device of the invention, it is the most preferable that at least one kind of the foregoing specified phosphorescent metal complex is contained in an amount of from 5 to 30% by mass relative to the total mass of the light emitting layer.

In the organic electroluminescence device, it is preferable that any one layer of the organic layers contains a hydrocarbon compound, and it is more preferable that the light emitting layer contains a hydrocarbon compound.

Also, the hydrocarbon compound is preferably a compound represented by the following formula (VI).

By appropriately using the compound represented by the formula (VI) together with the light emitting material, an intermolecular interaction of the material is appropriately controlled, and an energy gap interaction between adjacent molecules to each other is made uniform. Thus, it becomes possible to further lower the driving voltage.

Also, the compound represented by the formula (VI) which is used in the organic electroluminescence device is excellent in chemical stability, small in denaturation such as decomposition of the material during the device driving and capable of preventing a lowering of the efficiency of the organic electroluminescence device or a lowering of the device life to be caused due to a decomposition product of the material.

The compound represented by the formula (VI) is described.

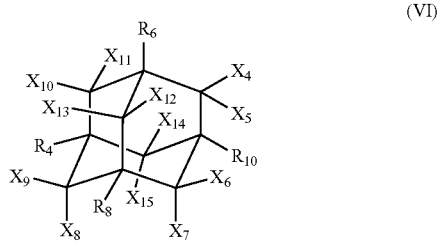

(VI)

In the formula (VI), each of $R_4$, $R_6$, $R_8$, $R_{10}$ and $X_4$ to $X_{15}$ independently represents a hydrogen atom, an alkyl group or an aryl group.

The alkyl group represented by each of $R_4$, $R_6$, $R_8$, $R_{10}$ and $X_4$ to $X_{15}$ in the formula (VI) may be substituted with an adamantane structure or an aryl structure. The alkyl group has preferably from 1 to 70 carbon atoms, more preferably from 1 to 50 carbon atoms, further preferably from 1 to 30 carbon atoms, even further preferably from 1 to 10 carbon atoms, and especially preferably from 1 to 6 carbon atoms. Of those, a linear alkyl group having from 2 to 6 carbon atoms is the most preferable.

Examples of the alkyl group represented by each of $R_4$, $R_6$, $R_8$, $R_{10}$ and $X_4$ to $X_{15}$ in the formula (VI) include an n-$C_{50}H_{101}$ group, an n-$C_{30}H_{61}$ group, a 3-(3,5,7-triphenyladamantan-1-yl)propyl group (carbon atom number: 31), a trityl group (carbon atom number: 19), a 3-(adamantan-1-yl)propyl group (carbon atom number: 13), a 9-decalyl group (carbon atom number: 10), a benzyl group (carbon atom number: 7), a cyclohexyl group (carbon atom number: 6), an n-hexyl group (carbon atom number: 6), an n-pentyl group (carbon atom number: 5), an n-butyl group (carbon atom number: 4), an n-propyl group (carbon atom number: 3), a cyclopropyl group (carbon atom number: 3), an ethyl group (carbon atom number: 2) and a methyl group (carbon atom number: 1).

The aryl group represented by each of $R_4$, $R_6$, $R_8$, $R_{10}$ and $X_4$ to $X_{15}$ in the formula (VI) may be substituted with an adamantane structure or an alkyl structure. The aryl group has preferably from 6 to 30 carbon atoms, more preferably from 6 to 20 carbon atoms, further preferably from 6 to 15 carbon atoms, especially preferably from 6 to 10 carbon atoms, and most preferably 6 carbon atoms.

Examples of the aryl group represented by each of $R_4$, $R_6$, $R_8$, $R_{10}$ and $X_4$ to $X_{15}$ in the formula (VI) include a 1-pyrenyl group (carbon atom number: 16), a 9-anthracenyl group (carbon atom number: 14), a 1-naphthyl group (carbon atom number: 10), a 2-naphthyl group (carbon atom number: 10), a p-t-butylphenyl group (carbon atom number: 10), a 2-m-xylyl group (carbon atom number: 8), a 5-m-xylyl group (carbon atom number: 8), an o-tolyl group (carbon atom number: 7), an m-tolyl group (carbon atom number: 7), a p-tolyl group (carbon atom number: 7) and a phenyl group (carbon atom number: 6).

Though each of $R_4$, $R_6$, $R_8$ and $R_{10}$ in the formula (VI) may be a hydrogen atom, an alkyl group or an aryl group, from the viewpoint that a high glass transition temperature is preferable, it is preferable that at least one of them is an aryl group; it is more preferable that at least two of them are an aryl group; and it is especially preferable that three or four of them are an aryl group.

Though each of $X_4$ to $X_{15}$ in the formula (VI) may be a hydrogen atom, an alkyl group or an aryl group, each of $X_4$ to $X_{15}$ is preferably a hydrogen atom or an aryl group, and especially preferably a hydrogen atom.

Since the organic electroluminescence device is prepared using a vacuum vapor deposition process or a solution coating process, from the viewpoints of vapor deposition aptitude and solubility, a molecular weight of the compound represented by the formula (VI) in the invention is preferably not more than 2,000, more preferably not more than 1,200, and especially preferably not more than 1,000. Also, from the viewpoint of vapor deposition aptitude, when the molecular weight of the compound represented by the formula (VI) is too low, a vapor pressure is small, change from a gas phase to a solid phase does not take place, and it is difficult to form an organic layer. Therefore, the molecular weight of the compound represented by the formula (VI) is preferably 250 or more, more preferably 350 or more, and especially preferably 400 or more.

It is preferable that the compound represented by the formula (VI) is a solid at room temperature (25° C.); it is more preferable that the compound represented by the formula (VI) is a solid in the range of from room temperature (25° C.) to 40° C.; and it is especially preferable that the compound represented by the formula (VI) is a solid in the range of from room temperature (25° C.) to 60° C.

In the case where the compound represented by the formula (VI), which does not form a solid at room temperature (25° C.), is used, it is possible to form a solid phase at ordinary temperature upon being combined with other material.

The compound represented by the formula (VI) is not limited with respect to an application thereof and may be contained in any layer within the organic layer. As to the layer into which the compound represented by the formula (VI) in the invention is introduced, the compound represented by the formula (VI) is preferably contained in any one or a plurality of a light emitting layer, a hole injection layer, a hole transport layer, an electron transport layer, an electron injection layer, an exciton blocking layer and a charge blocking layer as described later; more preferably contained in any one or a plurality of a light emitting layer, a hole injection layer, a hole transport layer, an electron transport layer and an electron injection layer; especially preferably contained in any one or a plurality of a light emitting layer, a hole injection layer and a hole transport layer; and most preferably contained in a light emitting layer.

In the case where the compound represented by the formula (VI) is used in the organic layer, it is necessary that a content of the compound represented by the formula (VI) is controlled to an extent that charge transporting properties are not hindered. The content of the compound represented by the formula (VI) is preferably from 0.1 to 70% by mass, more preferably from 0.1 to 30% by mass, and especially preferably from 0.1 to 25% by mass.

Also, in the case where the compound represented by the formula (VI) is used in plural organic layers, it is preferable that the compound represented by the formula (VI) is contained in an amount falling within the foregoing range in each of the layers.

Only one kind of the compound represented by the formula (VI) may be contained in any one organic layer; and a combination of plural kinds of the compound represented by the formula (VI) in an arbitrary proportion may be contained.

Specific examples of the compound represented by the formula (VI) are enumerated below, but it should not be construed that the invention is limited thereto.

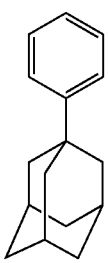

(1-1)

(1-2)

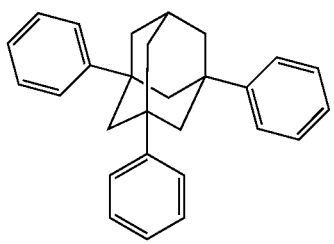

(1-3)

(1-4)

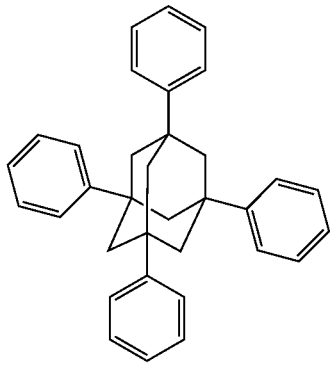

(1-5)

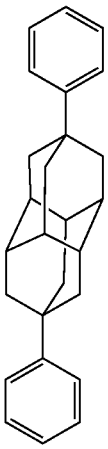

(1-6)

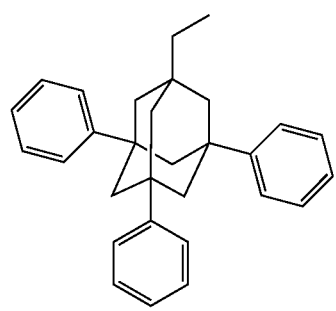
(1-7)
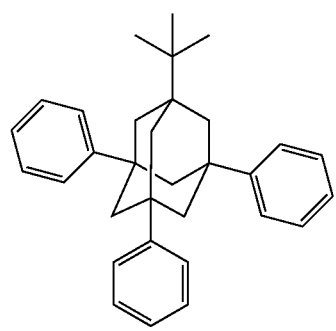
(1-8)
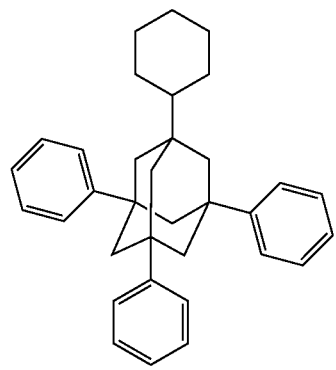
(1-9)
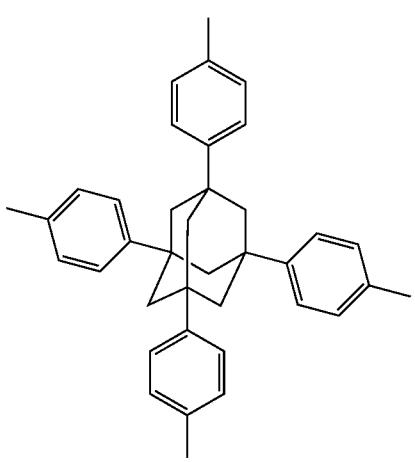
(1-10)
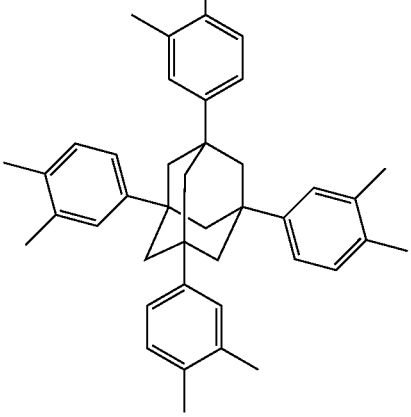
(1-11)
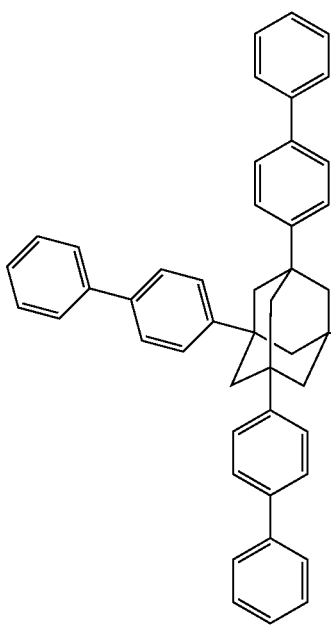
(1-12)
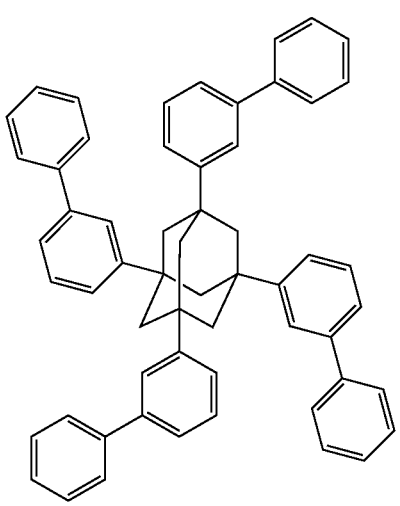
(1-13)

(1-14)
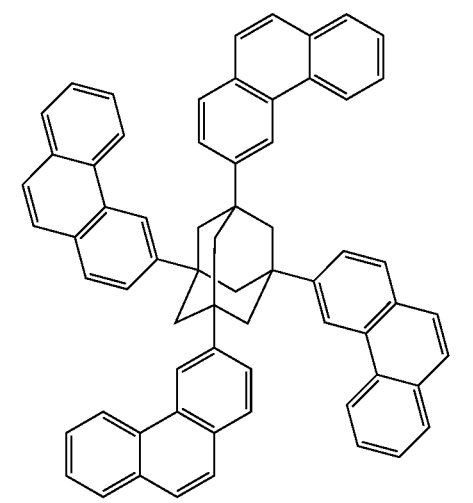
(1-15)
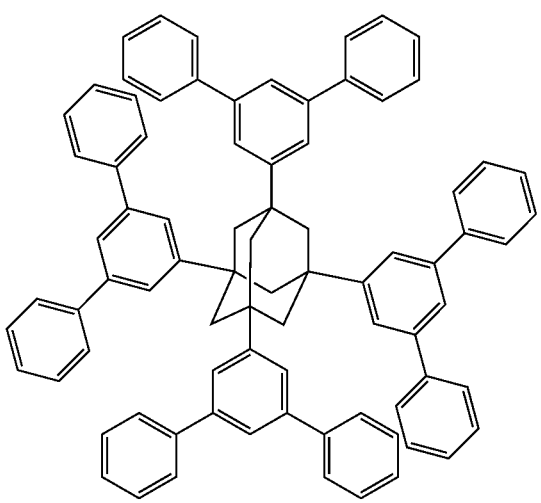
(1-16)
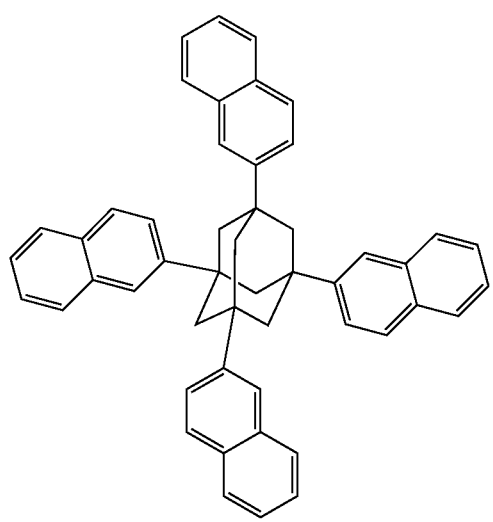
(1-17)
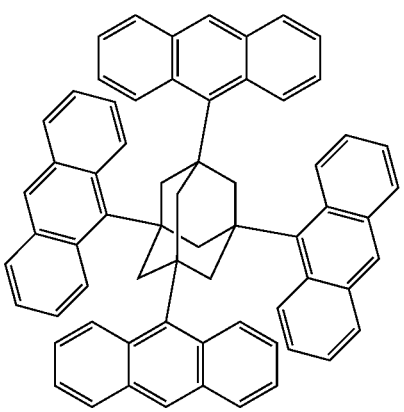
(1-18)
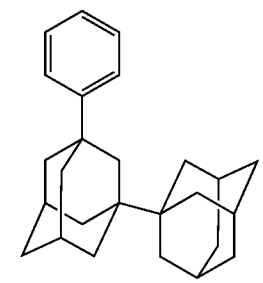
(1-19)
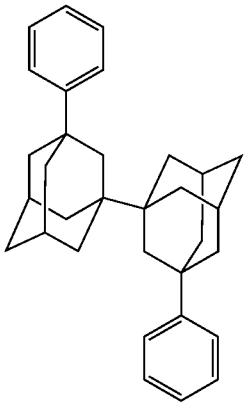
(1-20)
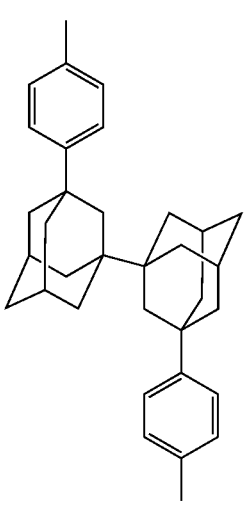

(1-21)
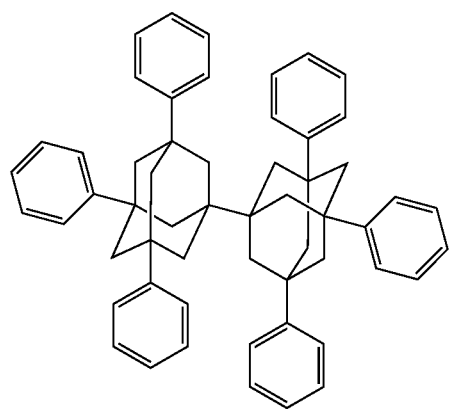
(1-22)
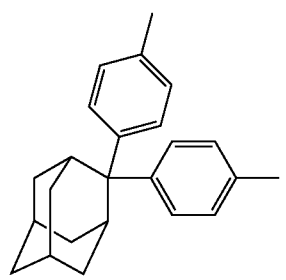
(1-23)
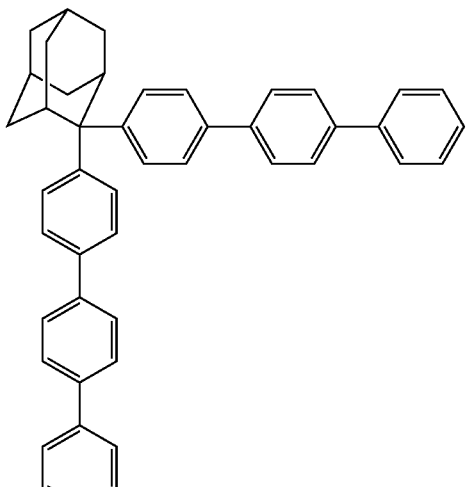
(1-24)
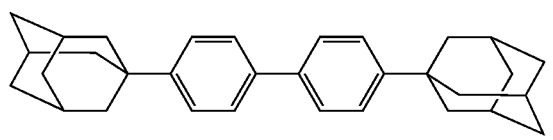
(1-25)
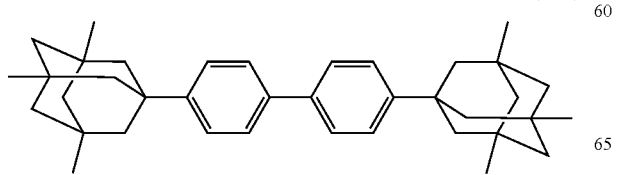
(1-26)
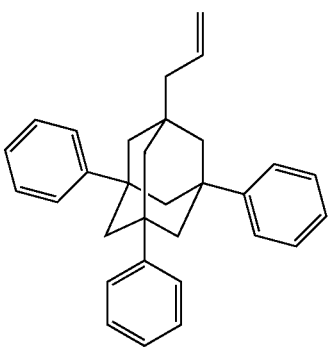
(1-27)
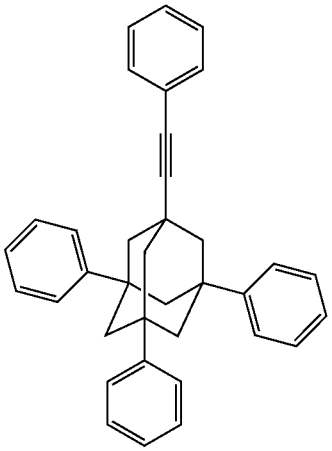
(1-28)
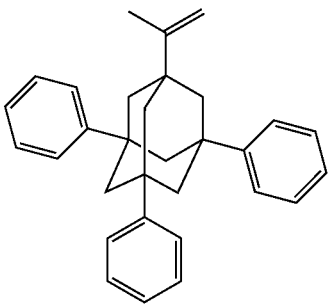
(1-29)
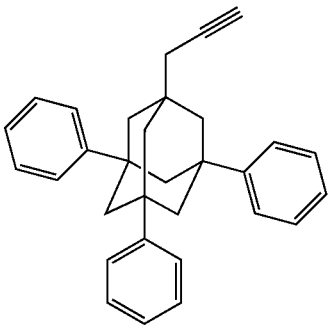

(1-30)
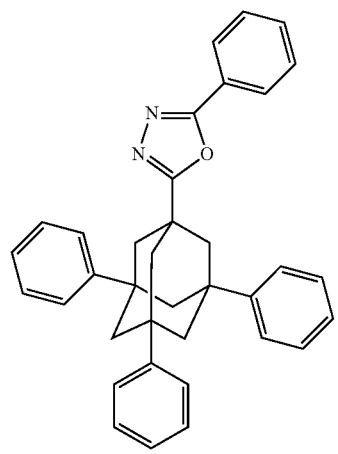
(1-31)
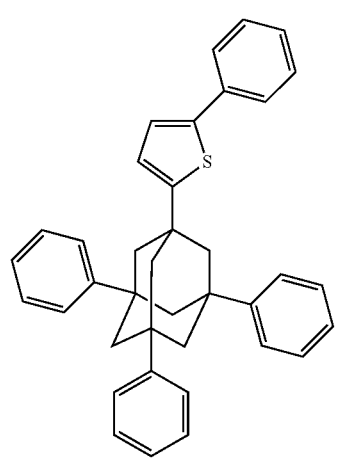
(1-32)
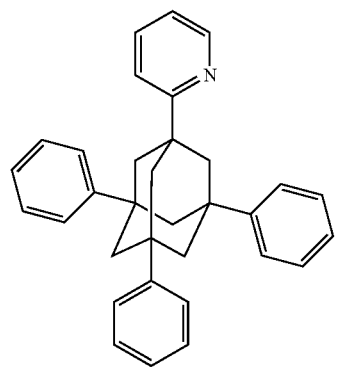
(1-33)
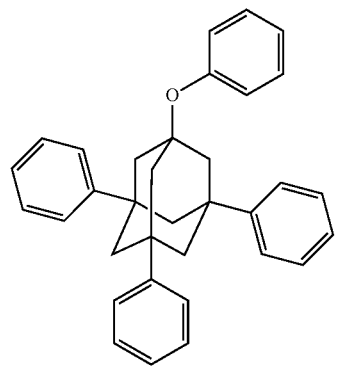
(1-34)
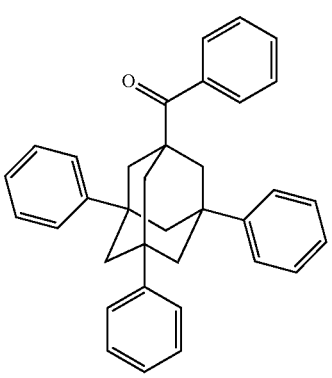
(1-35)
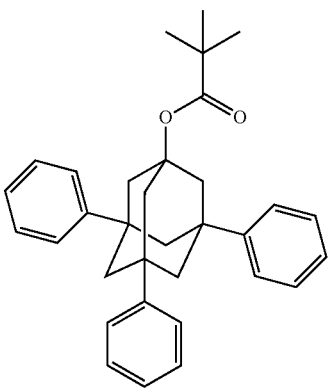
(1-36)
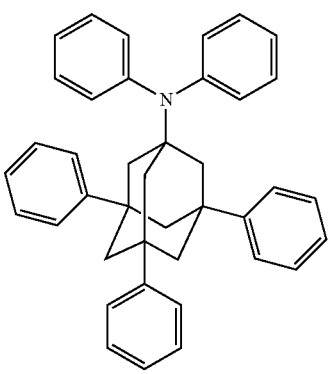
(1-37)
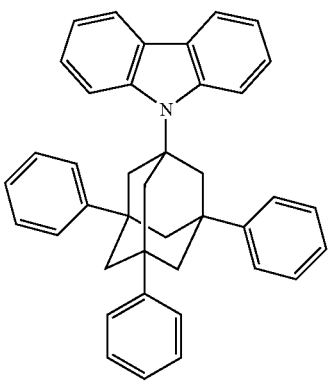

(1-38)
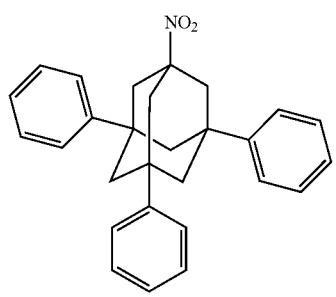
(1-39)
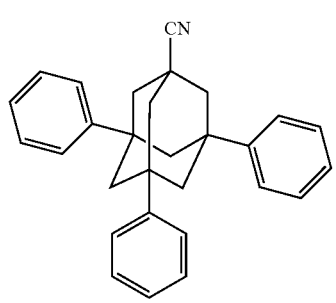
(1-40)
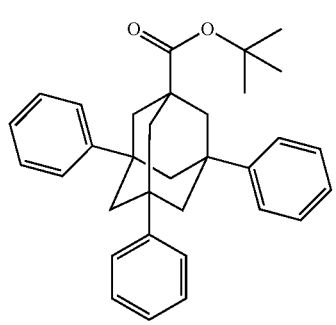
(1-41)
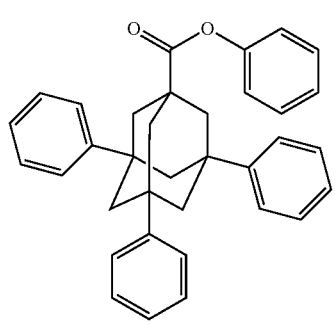
(1-42)
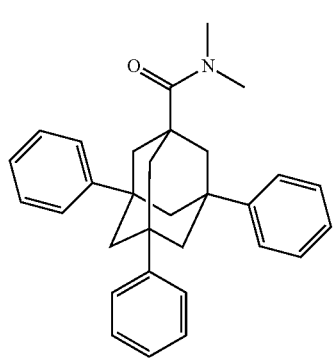
(1-43)
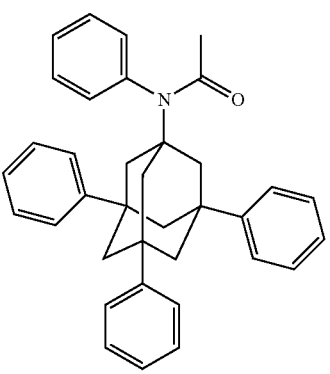
(1-44)
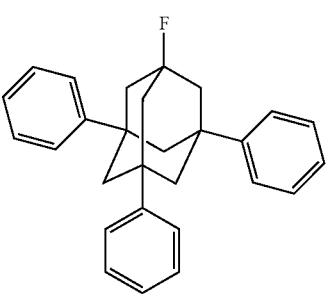
(1-45)
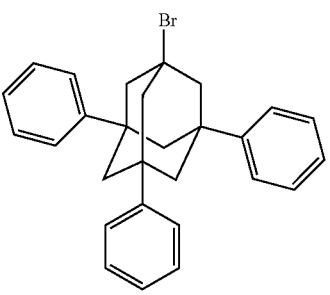
(1-46)
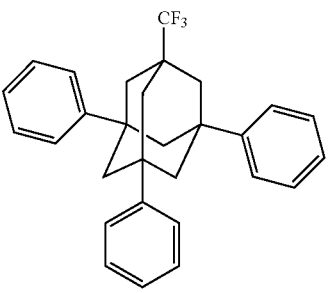
(1-47)
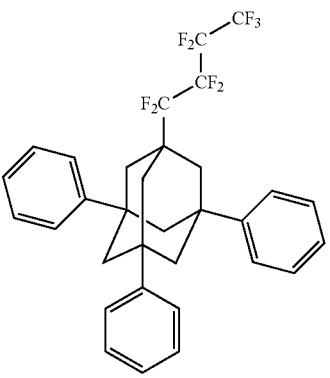

-continued (1-48)

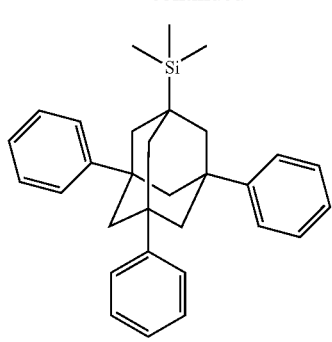

(1-49)

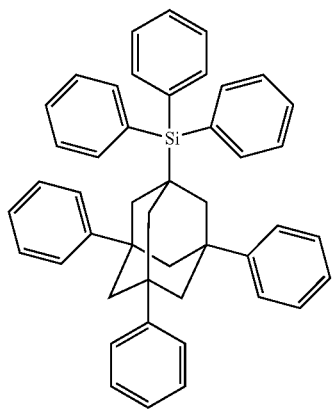

The compound represented by the formula (VI) can be synthesized by properly combining adamantane or a halogenated adamantane with an alkyl halide or an alkyl magnesium halide (Grignard reagent). For example, a halogenated adamantane can be coupled with an alkyl halide using indium (see Document 1). Also, an alkyl halide can be converted into an alkyl copper reagent and then coupled with a Grignard reagent of an aromatic compound (see Document 2). Also, an alkyl halide can be coupled with an appropriate aryl boric acid using a palladium catalyst (see Document 3).

Document 1: *Tetrahedron Lett.*, 39, 9557 to 9558 (1998)
Document 2: *Tetrahedron Lett.*, 39, 2095 to 2096 (1998)
Document 3: *J. Am. Chem. Soc.*, 124, 13662 to 13663 (2002)

The adamantane structure having an aryl group can be synthesized by properly combining adamantane or a halogenated adamantane with a corresponding arene or aryl halide.

In the foregoing manufacturing method, in the case where the defined substituents are changed under a condition of a certain synthesis method or are inadequate for carrying out the instant method, the manufacture can be easily made by means of, for example, protection and deprotection of a functional group (see, for example, *Protective Groups in Organic Synthesis*, written by T. W. Greene, John Wiley & Sons Inc. (1981), etc.), and the like. Also, the order of the reaction steps such as introduction of a substituent can be properly changed, if desired.

Though a thickness of the light emitting layer is not particularly limited, in general, it is preferably from 1 nm to 500 nm, more preferably from 5 nm to 200 nm, and further preferably from 10 nm to 100 nm.

—Hole Injection Layer and Hole Transport Layer—

Each of the hole injection layer and the hole transport layer is a layer having a function of accepting a hole from the anode or the anode side to transport it into the cathode side.

In the invention, it is preferable that a hole injection layer or a hole transport layer containing an electron-accepting dopant is contained as the organic layer.

—Electron Injection Layer and Electron Transport Layer—

Each of the electron injection layer and the electron transport layer is a layer having a function of accepting an electron from the cathode or the cathode side to transport it into the anode side.

With respect to the hole injection layer, the hole transport layer, the electron injection layer and the electron transport layer, the matters disclosed in paragraphs [0165] to of JP-A-2008-270736 can be applied to the invention.

—Hole Blocking Layer—

The hole blocking layer is a layer having a function of preventing permeation of the hole having been transported from the anode side to the light emitting layer into the cathode side from occurring. In the invention, the hole blocking layer can be provided as an organic layer adjacent to the light emitting layer on the cathode side.

Examples of an organic compound constituting the hole blocking layer include aluminum complexes such as aluminum(III) bis(2-methyl-8-quinolinato)4-phenylphenolate (abbreviated as "BAlq"); triazole derivatives; and phenanthroline derivatives such as 2,9-dimethyl-4,7-diphenyl-1,10-phenanthroline (abbreviated as "BCP").

A thickness of the hole blocking layer is preferably from 1 nm to 500 nm, more preferably from 5 nm to 200 nm, and further preferably from 10 nm to 100 nm.

The hole blocking layer may be of a single layer structure composed of one or two or more kinds of the foregoing materials or may be of a multilayer structure composed of a plurality of layers of the same composition as or different composition from each other.

—Electron Blocking Layer—

The electron blocking layer is a layer having a function of preventing permeation of an electron having been transported from the cathode side to the light emitting layer into the anode side from occurring. In the invention, the electron blocking layer can be provided as an organic layer adjacent to the light emitting layer on the anode side.

Examples of an organic compound constituting the electron blocking layer include those exemplified above as the hole transport material.

A thickness of the electron blocking layer is preferably from 1 nm to 500 nm, more preferably from 5 nm to 200 nm, and further more preferably from 10 nm to 100 nm.

The electron blocking layer may be of a single-layered structure composed of one or two or more kinds of the foregoing materials or may be of a multilayered structure composed of a plurality of layers of the same composition as or different composition from each other.

In the organic electroluminescence device of the invention, it is preferable that the electrode includes an anode; that a charge transport layer is formed between the light emitting layer and the anode; and that the charge transport layer contains a carbazole compound.

The carbazole compound is preferably a carbazole compound represented by the following formula (a).

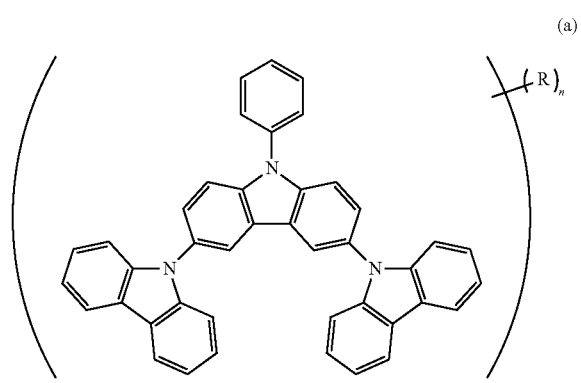

(a)

In the formula (a), R represents a substituent capable of being substituted on a hydrogen atom of the structure; in the case where plural Rs are present, each R may be the same as or different from every other R; and n represents an integer of from 0 to 8.

In the case where the compound represented by the formula (a) is used in the charge transport layer, a content of the compound represented by the formula (a) is preferably from 50 to 100% by mass, more preferably from 80 to 100% by mass, and especially preferably from 95 to 100% by mass.

Also, in the case where the compound represented by the formula (a) is used in plural organic layers, it is preferable that the compound represented by the formula (a) is contained in an amount falling within the foregoing range in each of the layers.

Only one kind of the compound represented by the formula (a) may be contained in any one organic layer; and a combination of plural kinds of the compound represented by the formula (a) in an arbitrary proportion may be contained.

A thickness of the charge transport layer containing the compound represented by the formula (a) is preferably from 1 nm to 500 nm, more preferably from 3 nm to 200 nm, and further preferably from 5 nm to 100 nm. Also, it is preferable that the charge transport layer is provided adjacent to the light emitting layer.

The charge transport layer may be of a single-layered structure composed of one or two or more kinds of the foregoing materials or may be of a multilayered structure composed of a plurality of layers of the same composition as or different composition from each other.

Specific examples of the substituent represented by R include a halogen atom, an alkoxy group, a cyano group, a nitro group, an alkyl group, an aryl group and an aromatic heterocyclic group. Of those, an alkyl group having not more than 10 carbon atoms and a substituted or unsubstituted aryl group having not more than 10 carbon atoms are preferable; and an alkyl group having not more than 6 carbon atoms is more preferable.

n represents an integer of from 0 to 8, preferably from 0 to 4, and more preferably from 0 to 2.

The hydrogen atom constituting the formula (a) also includes an isotope of hydrogen (for example, a deuterium atom, etc.). In that case, all of the hydrogen atoms in the compound may be replaced by an isotope of hydrogen. Also, the compound represented by the formula (a) may be a mixture including a compound in which a part of the hydrogen atoms is an isotope of hydrogen.

It is possible to synthesize the compound represented by the formulae (a) by a combination of various known synthesis methods. Most generally, with respect to the carbazole compound, there is exemplified a synthesis by an Aza-Cope rearrangement reaction of a condensate of an aryl hydrazine and a cyclohexane derivative and subsequent dehydroaromatization (*Reactions and Syntheses: In the Organic Chemistry*, page 339, written by L. F. Tieze and Th. Eicher, translated by Takano and Ogasawara and published by Nankodo). Also, with respect to a coupling reaction of the obtained carbazole compound and a halogenated aryl compound using a palladium catalyst, there are exemplified the methods described in *Tetrahedron Letters*, Vol. 39, page 617 (1998), ibid, Vol. 39, page 2367 (1998) and ibid, Vol. 40, page 6393 (1999) and so on. The reaction temperature and the reaction time are not particularly limited, and conditions described in the foregoing documents can be applied.

With respect to the compound represented by the formula (a) according to the invention, though it is preferable to form a thin layer by a vacuum vapor deposition process, a wet process such as solution coating can also be suitably adopted. From the viewpoints of vapor deposition aptitude and solubility, a molecular weight of the compound represented by the formula (a) is preferably not more than 2,000, more preferably not more than 1,200, and especially preferably not more than 800. Also, from the viewpoint of vapor deposition aptitude, when the molecular weight is too low, a vapor pressure is small, change from a gas phase to a solid phase does not take place, and it is difficult to form an organic layer. Therefore, the molecular weight of the compound represented by the formula (a) is preferably 250 or more, and especially preferably 300 or more.

Specific examples of the compound represented by the formula (a) in the invention are enumerated below, but it should not be construed that the invention is limited thereto.

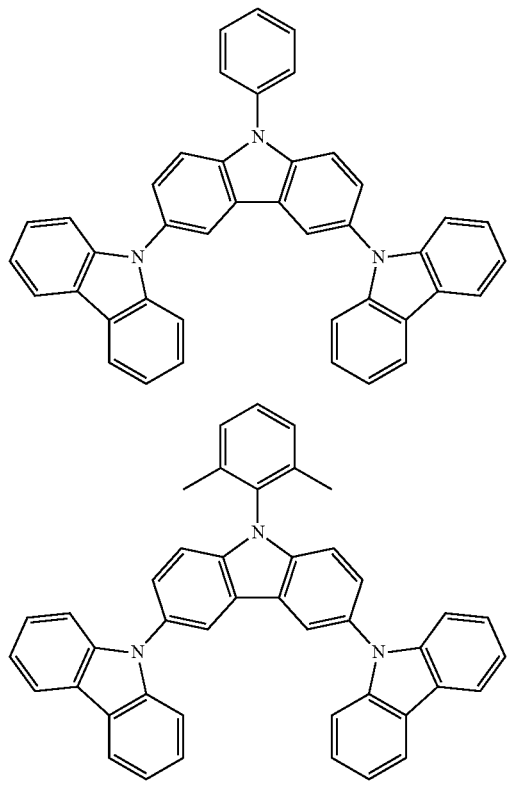

97
-continued
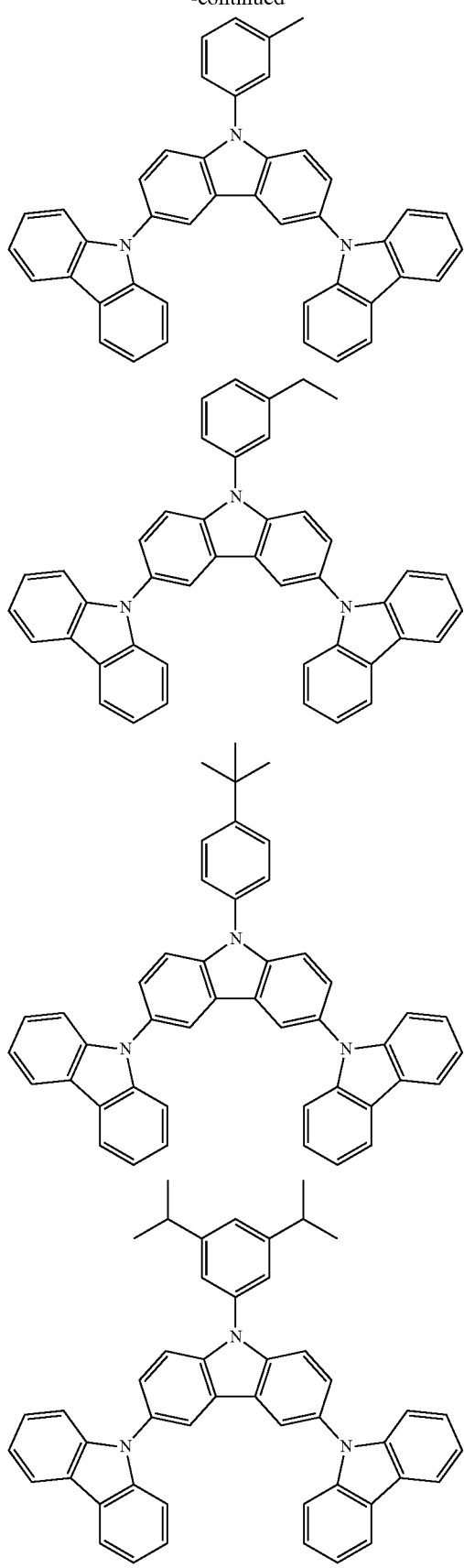
98
-continued
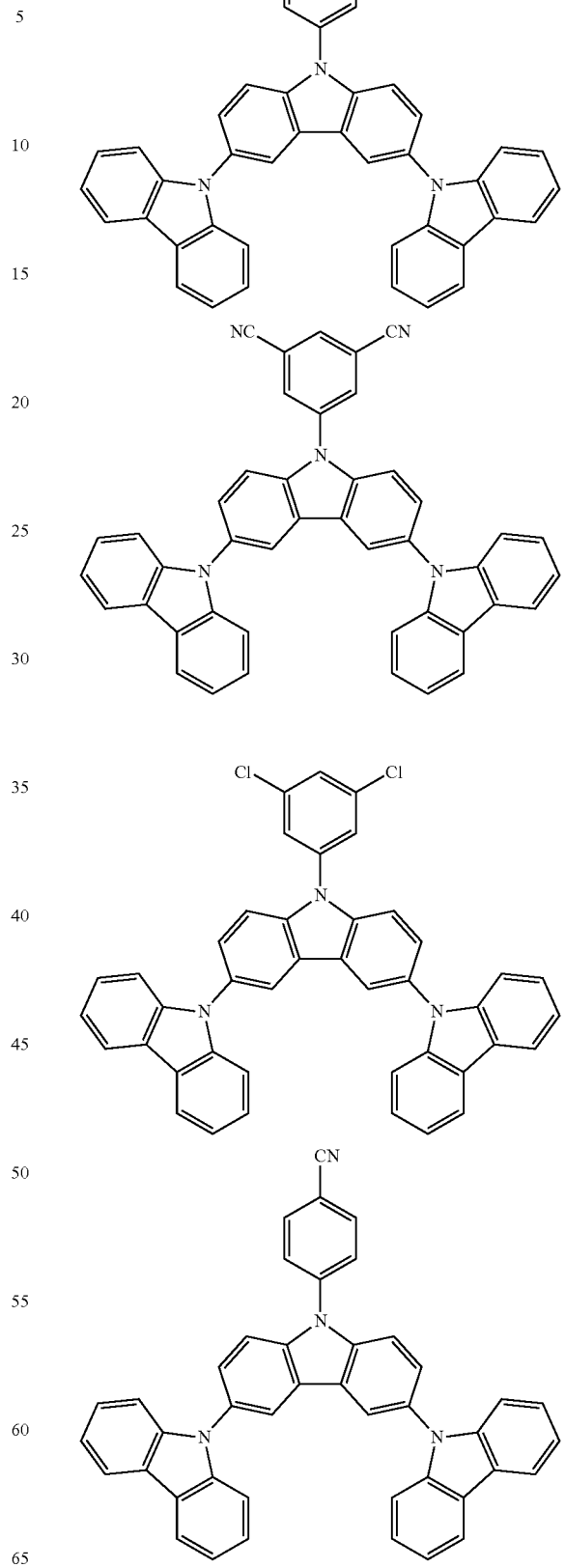

99
-continued
100
-continued
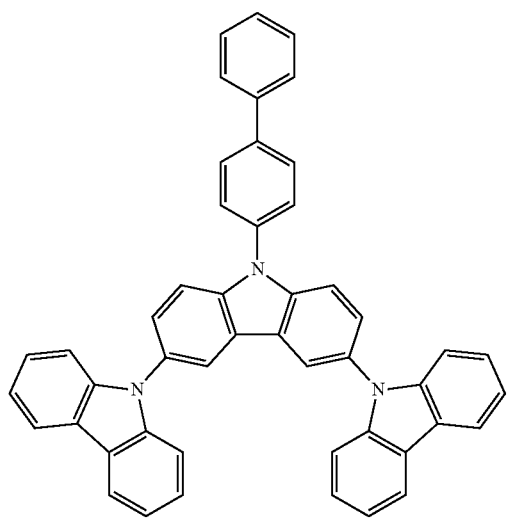
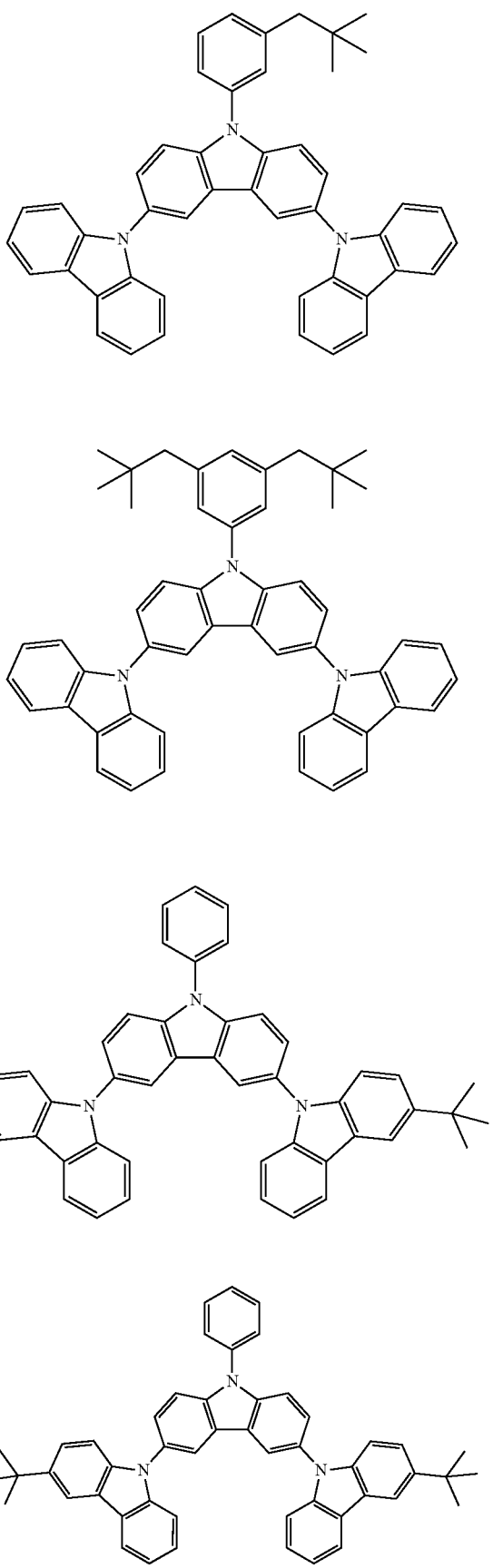

101
-continued
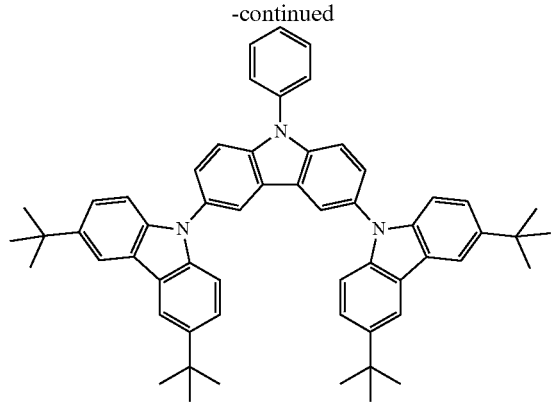
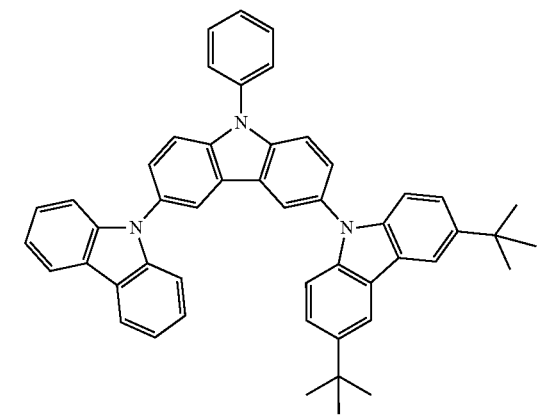
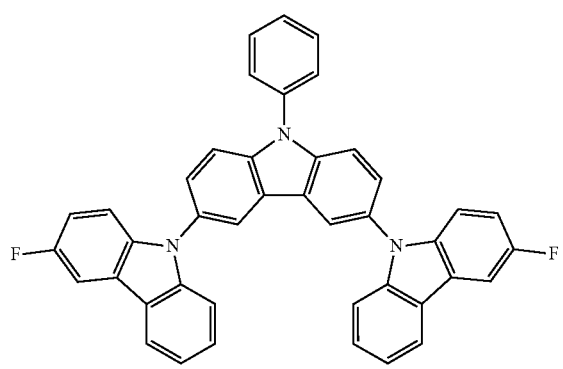
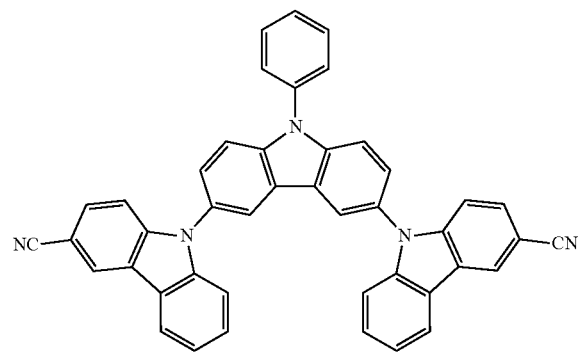
102
-continued
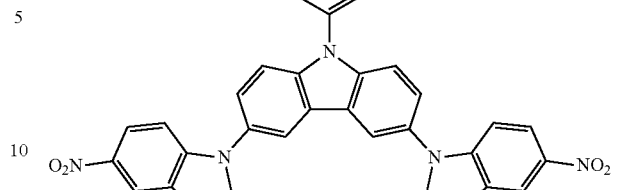
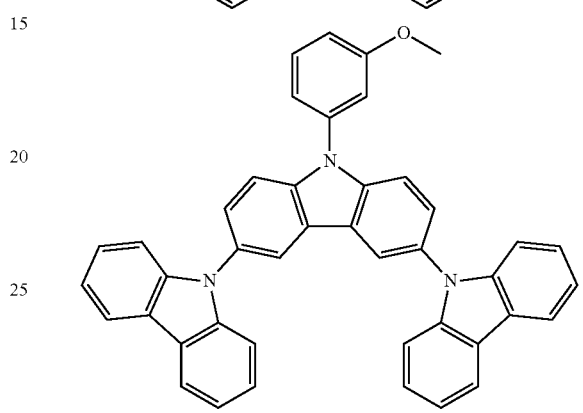
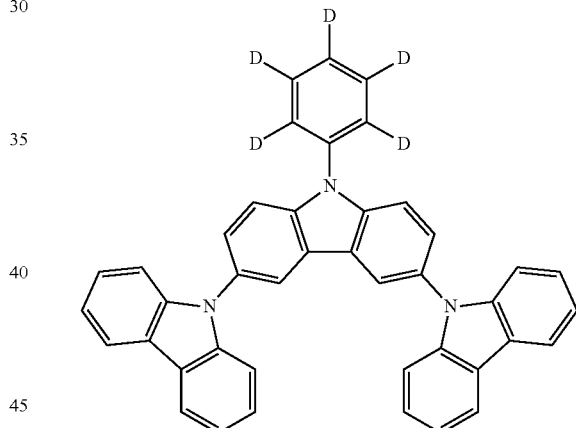
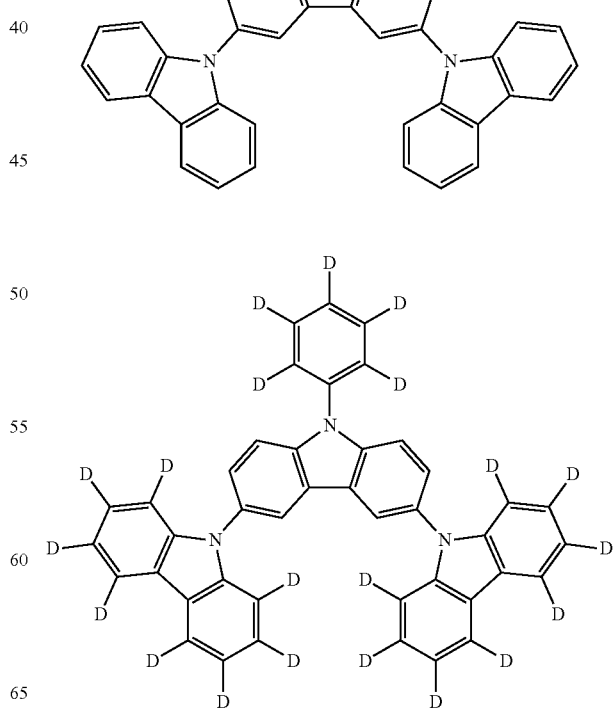

-continued

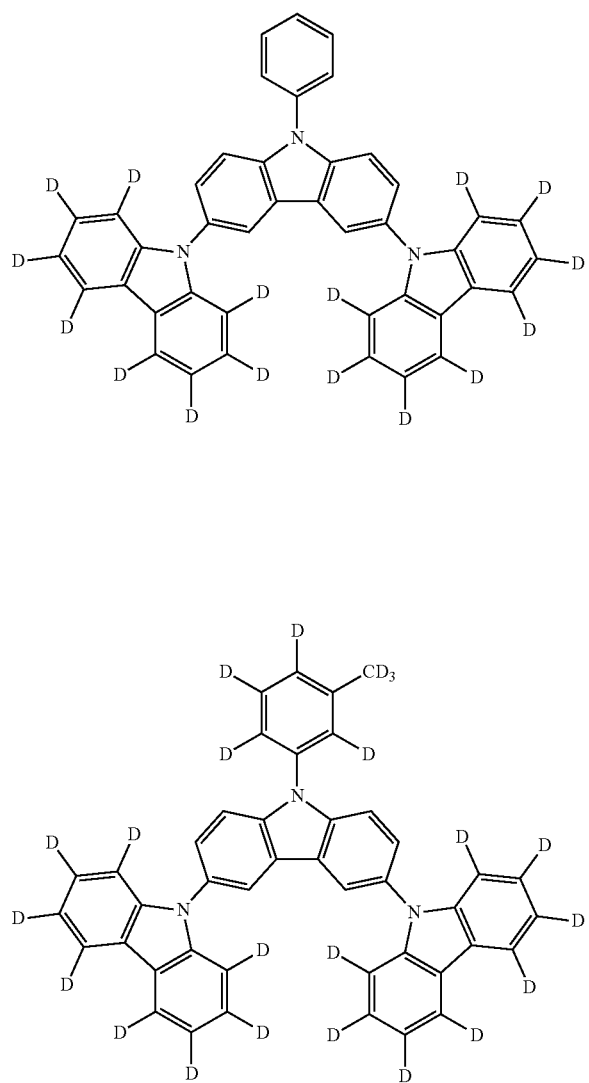

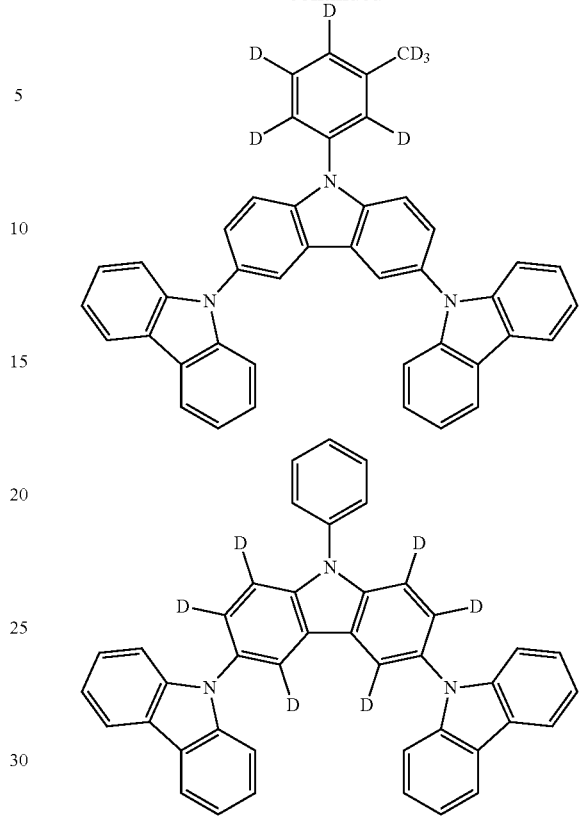

<Protective Layer>
In the invention, the whole of the organic EL device may be protected by a protective layer.

With respect to the protective layer, the matters disclosed in paragraphs [0169] to [0170] of JP-A-2008-270736 can be applied to the invention.

<Sealing Vessel>
In the device of the invention, the whole of the device may be sealed using a sealing vessel.

With respect to the sealing vessel, the matters disclosed in paragraph [0171] of JP-A-2008-270736 can be applied to the invention.

<Driving>
According to the organic electroluminescence device of the invention, light emission can be obtained by impressing a voltage of direct current (optionally including an alternating current component) (usually from 2 volts to 15 volts) or a current of direct current between the anode and the cathode.

As to the driving method of the organic electroluminescence device of the invention, driving methods disclosed in JP-A-2-148687, JP-A-6-301355, JP-A-5-29080, JP-A-7-134558, JP-A-8-234685, JP-A-8-241047, Japanese Patent No. 2784615 and U.S. Pat. Nos. 5,828,429 and 6,023,308 can be applied.

In the luminescence device of the invention, a light extracting efficiency can be enhanced by various known ways and means. For example, it is possible to enhance the light extracting efficiency and to enhance the external quantum efficiency by processing a surface shape of the substrate (for example, forming a fine uneven pattern), controlling a refractive index of each of the substrate, the ITO layer and the organic layer, controlling a thickness of each of the substrate, the ITO layer and the organic layer, or the like.

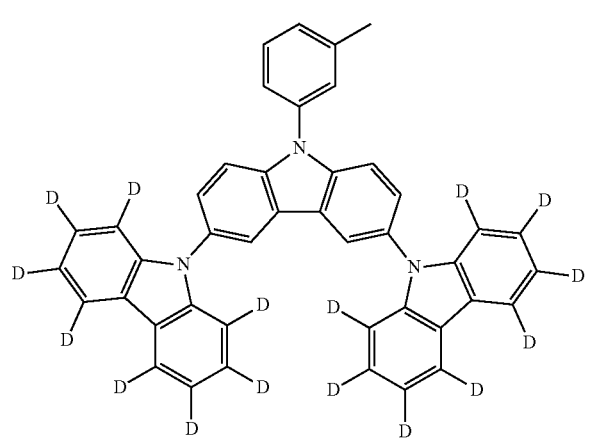

The luminescence device of the invention may be of a so-called top emission mode for extracting light emission from the anode side.

The organic EL device in the invention may have a resonator structure. For example, the organic EL device in the invention includes a transparent substrate having a multilayered film mirror composed of plural laminated films having a different refractive index from each other, a transparent or translucent electrode, a light emitting layer and a metal electrode superimposed thereon. The light emitted in the light emitting layer repeats reflection between the multilayered film mirror and the metal electrode while making them function as a reflector and resonates.

In another preferred embodiment, each of a transparent or translucent electrode and a metal electrode functions as a reflector on a transparent substrate, and the light emitted in the light emitting layer repeats reflection therebetween and resonates.

In order to form a resonator structure, an optical path length which is determined from effective refractive indexes of the two reflectors and a refractive index and a thickness of each layer between the reflectors is regulated so as to have an optimal value for the purpose of obtaining a desired resonance wavelength. A calculation expression of the case of the first embodiment is disclosed in JP-A-9-180883. A calculation expression of the case of the second embodiment is disclosed in JP-A-2004-127795.

The external quantum efficiency of the organic electroluminescence device of the invention is preferably 5% or more, and more preferably 7% or more. With respect to the numerical value of the external quantum efficiency, a maximum value of the external quantum efficiency at the time of driving the device at 20° C., or a value of the external quantum efficiency in the vicinity of from 100 to 300 cd/m$^2$ at the time of driving the device at 20° C., can be employed.

An internal quantum efficiency of the organic electroluminescence device of the invention is preferably 30% or more, more preferably 50% or more, and further preferably 70% or more. The internal quantum efficiency of the device is calculated by dividing the external quantum efficiency by the light extracting efficiency. Though in usual organic EL devices, the light extracting efficiency is about 20%, it is possible to regulate the light extracting efficiency to 20% or more by devising a shape of the substrate, a shape of the electrode, a film thickness of the organic layer, a film thickness of the inorganic layer, a refractive index of the organic layer, a refractive index of the inorganic layer or the like.

A maximum light emission wavelength (maximum intensity wavelength of emission spectrum) of the organic electroluminescence device of the invention is preferably 350 nm or more and not more than 700 nm, more preferably 350 nm or more and not more than 600 nm, further preferably 400 nm or more and not more than 520 nm, and especially preferably 400 nm or more and not more than 465 nm.

<Application of Luminescence Device of the Invention>

The luminescence device of the invention can be suitably utilized for light emitting units, pixels, display devices, displays, backlights, electro-photographs, illumination light sources, recording light sources, exposure light sources, read light sources, markers, signboards, interiors, optical communications and so on. In particular, the luminescence device of the invention is preferably used for devices which are driven in a region with high brightness, such as light emitting units, illumination units and display units.

Next, the light emitting unit of the invention is described by reference to FIG. 2.

The light emitting unit of the invention is one using the foregoing organic electroluminescence device.

Figure 2:
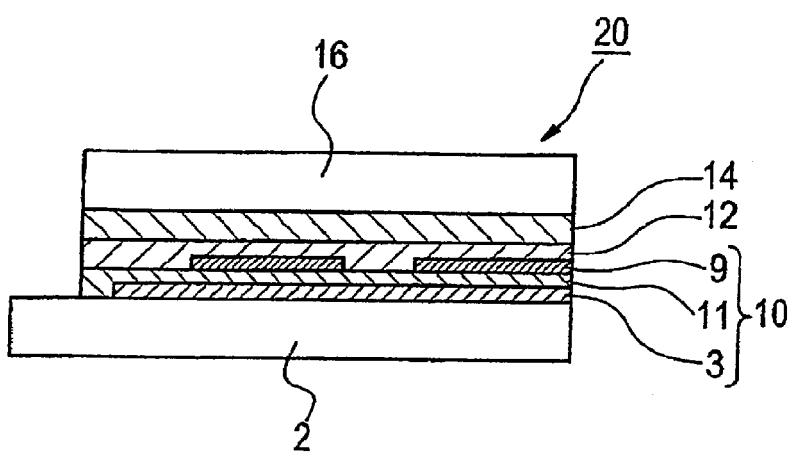
FIG. 2 is a diagrammatic view showing an example (second embodiment) of a light emitting unit according to the invention.

FIG. 2 is a sectional view diagrammatically showing an example of the light emitting unit of the invention.

A light emission unit 20 of FIG. 2 is constituted of a transparent substrate (supporting substrate) 2, an organic electroluminescence device 10, a sealing vessel 16 and so on.

The organic electroluminescence device 10 is constituted in such a manner that an anode (first electrode) 3, an organic layer 11 and a cathode (second electrode) 9 are laminated in this order on the substrate 2. Also, a protective layer 12 is laminated on the cathode 9, and furthermore, the sealing vessel 16 is provided on the protective layer 12 via an adhesive layer 14. In this respect, a part of each of the electrodes 3 and 9, a partition, an insulating layer and the like are omitted.

Here, a photocurable adhesive or a thermosetting adhesive such as an epoxy resin can be used as the adhesive layer 14, and for example, a thermosetting adhesive sheet can also be used.

The application of the light emission unit of the invention is not particularly limited, and examples thereof include, in addition to illumination units, display units of television receiver, personal computer, mobile phone, electronic paper, etc.

(Illumination Unit)

Next, the illumination unit according to an embodiment of the invention is described by reference to FIG. 3.

Figure 3:
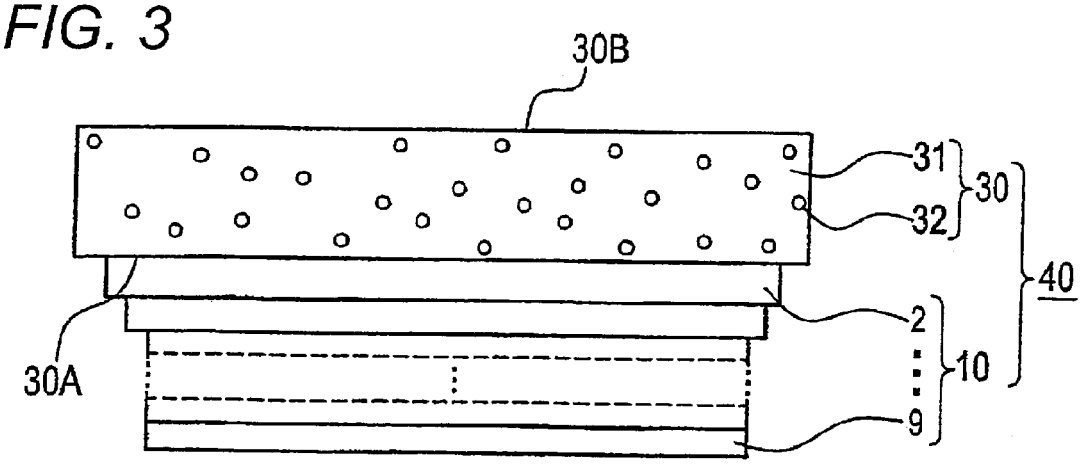
FIG. 3 is a diagrammatic view showing an example (third embodiment) of an illumination unit according to the invention.

FIG. 3 is a sectional view diagrammatically showing an example of the illumination unit according to an embodiment of the invention.

As shown in FIG. 3, an illumination unit 40 according to an embodiment of the invention is provided with the foregoing organic EL device 10 and a light scattering member 30. More specifically, the illumination unit 40 is constituted in such a manner that the substrate 2 of the organic EL device 10 and the light scattering member 30 come into contact with each other.

The light scattering member 30 is not particularly limited so far as it is able to scatter light. In FIG. 3, the light scattering member 30 is a member having a fine particle 32 dispersed in a transparent substrate 31. As the transparent substrate 31, for example, a glass substrate can be suitably exemplified. As the fine particle 32, a transparent resin fine particle can be suitably exemplified. As the glass substrate and the transparent resin fine particle, those which are known can be used. Such an illumination unit 40 is a unit which when light emission from the organic electroluminescence device 10 is made incident into a light incident surface 30A of the light scattering member 30, scatters the incident light by the light scattering member 30 and outputs the scattered light as illumination light from a light outgoing surface 30B.

EXAMPLES

The invention is more specifically described below by reference to the following Examples, but it should not be construed that the scope of the invention is limited to those Examples.

As all of organic materials used in the following Examples and Comparative Examples, those obtained by sublimation purification were used. Structures of compounds used in the Examples and Comparative Examples are shown below.

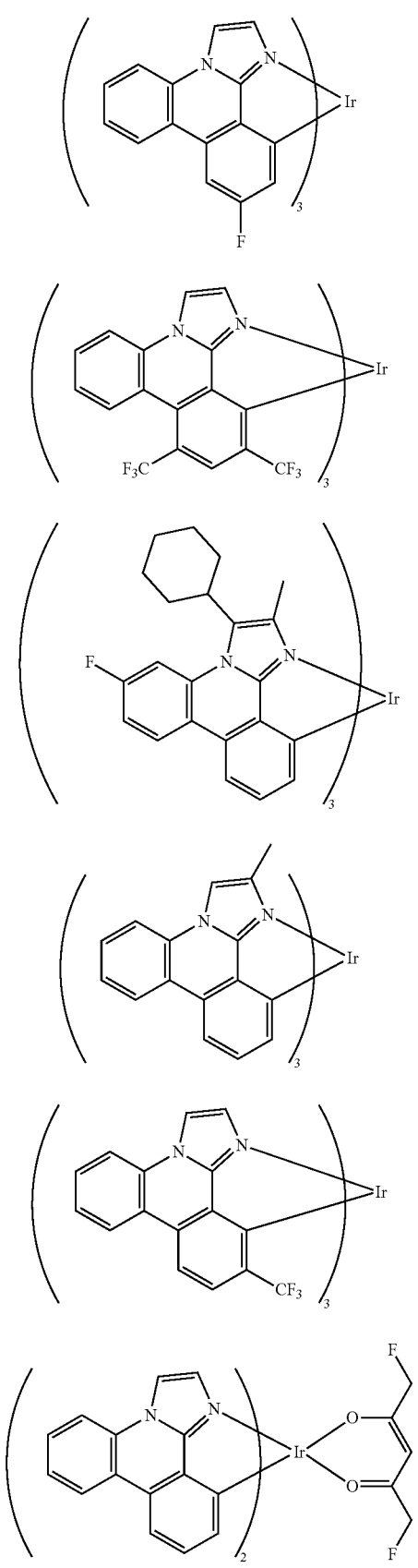
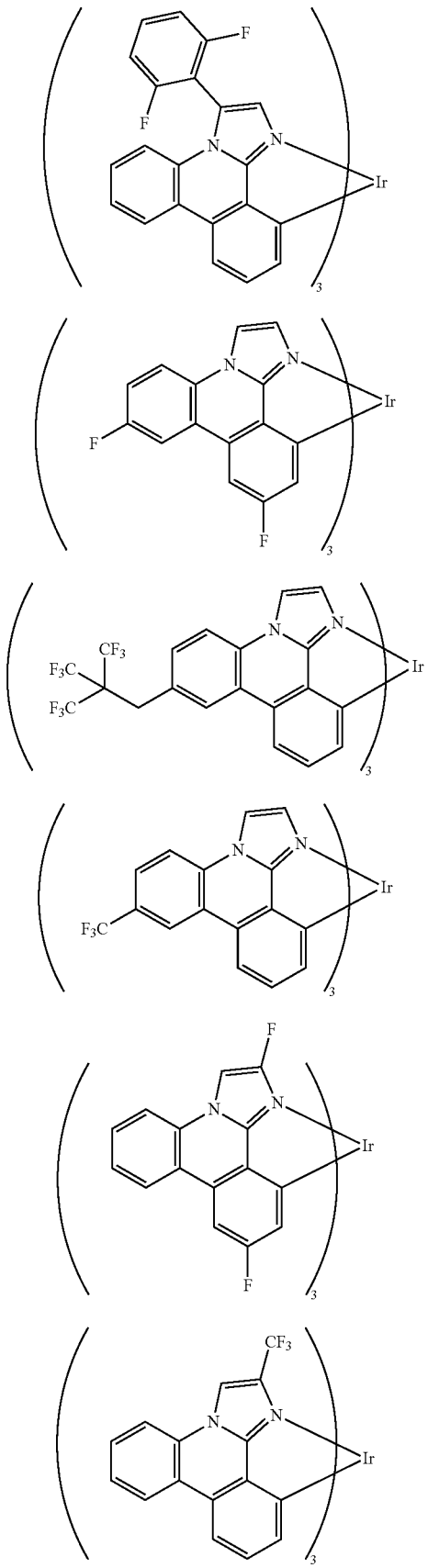

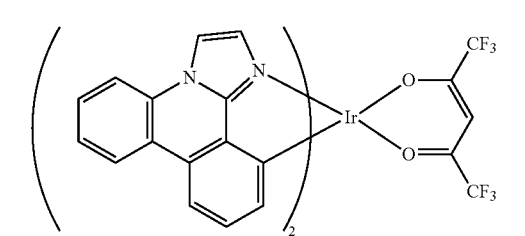
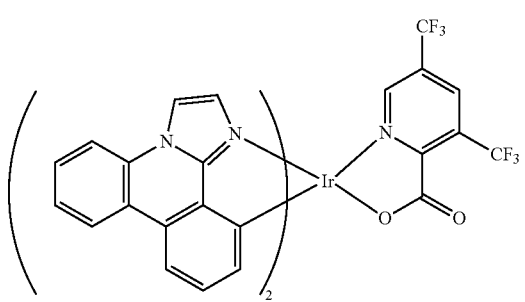
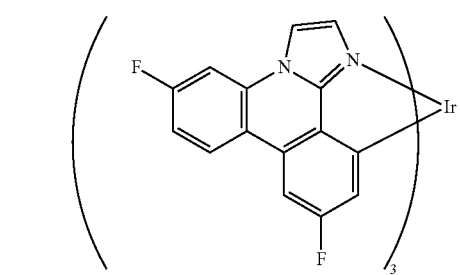
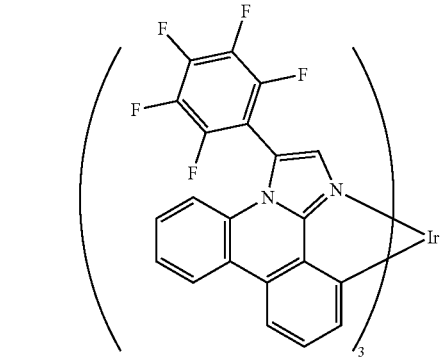
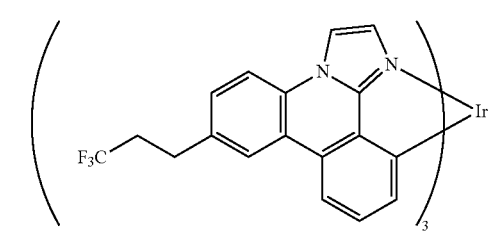
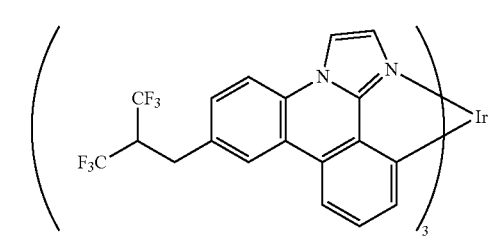
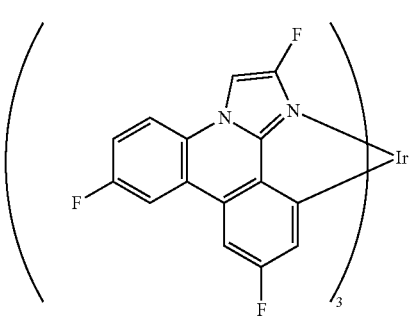
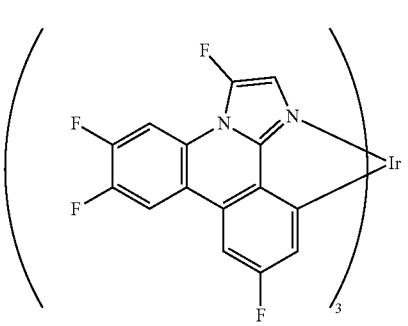
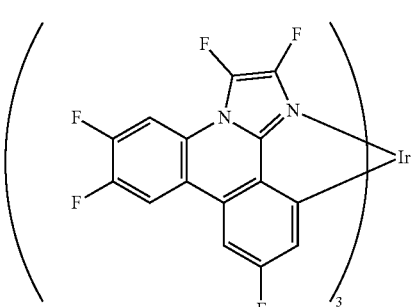
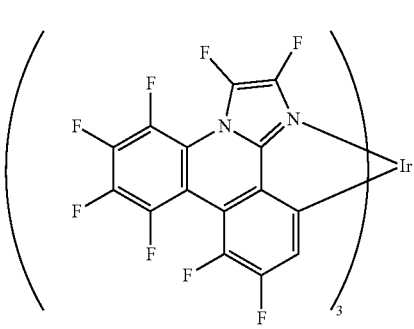

18
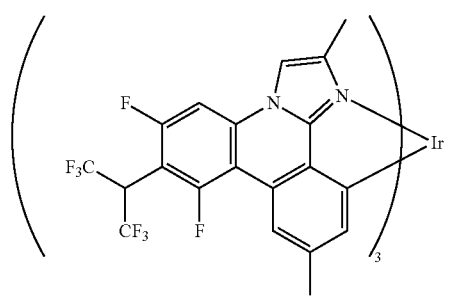
19
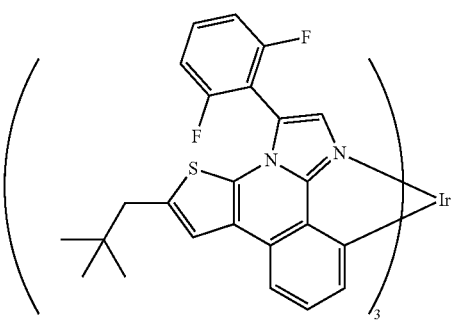
20
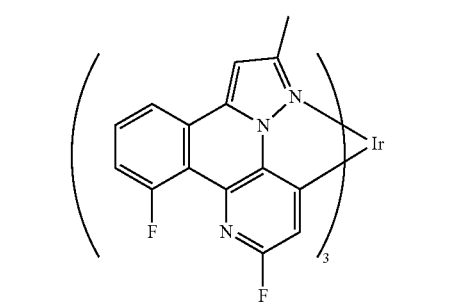
21
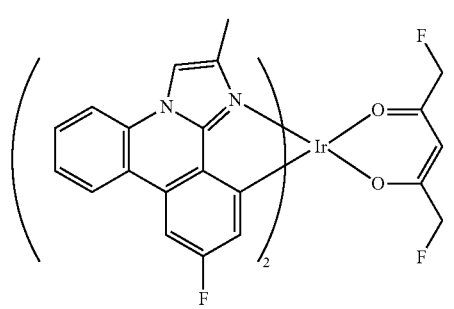
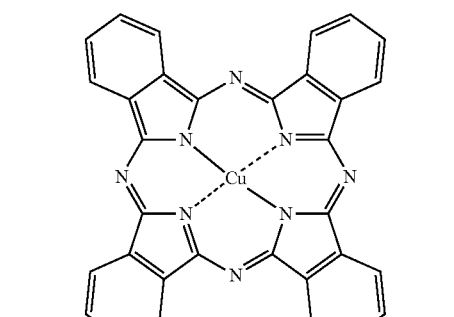
CuPc
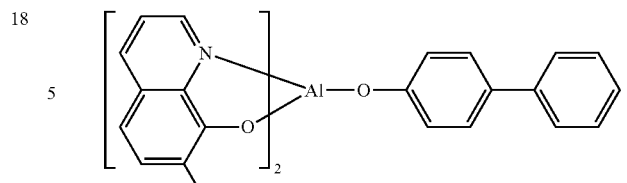
BAlq
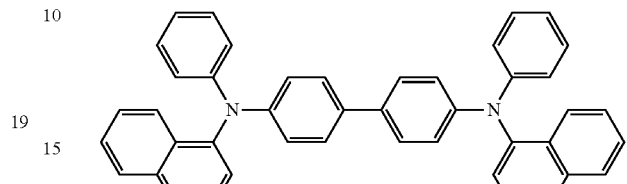
NPD
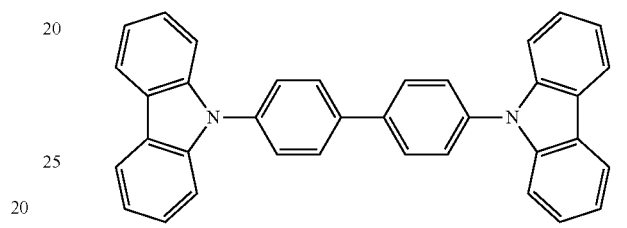
CBP
H-1
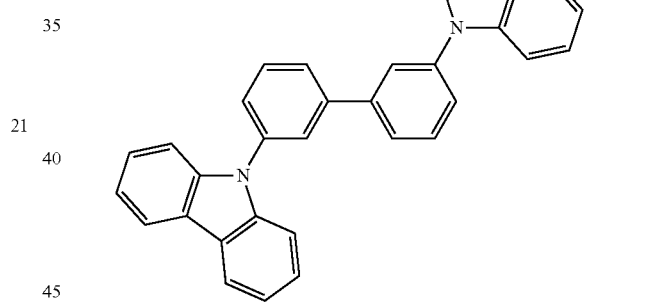
H-2
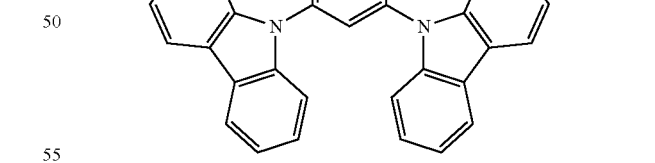
H-3
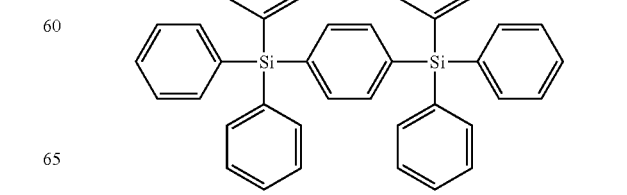

-continued

H-4
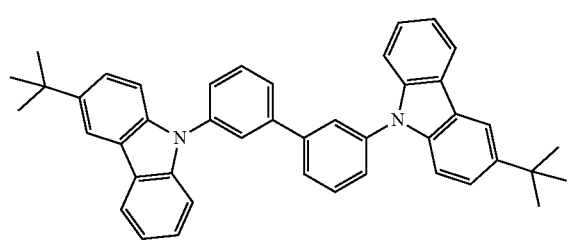

H-5
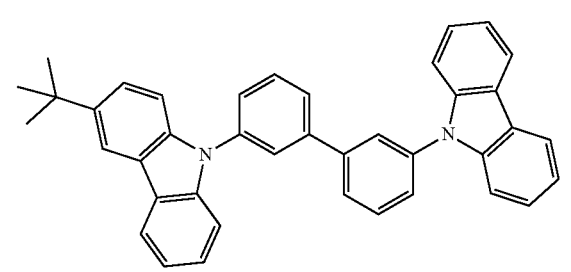

H-6
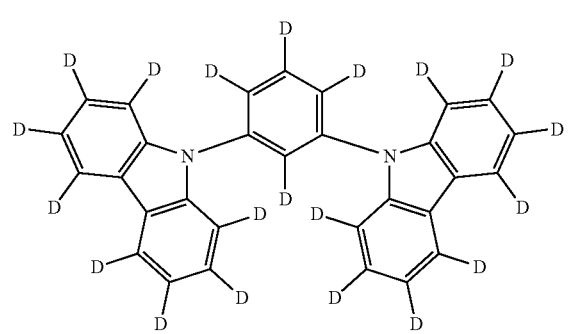

-continued

HT-2
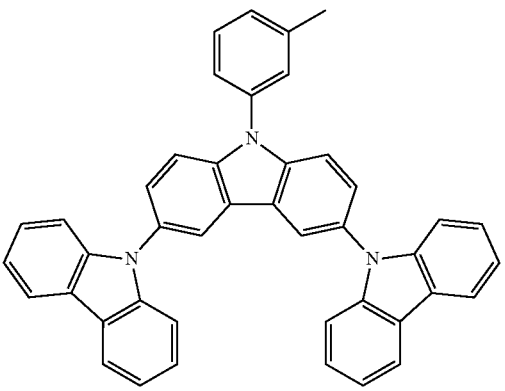 [SMILES: [2H]c1c(-n2c3ccccc3c3ccccc32)c([2H])c2c3c([2H])c(-n4c5ccccc5c5ccccc54)c([2H])c([2H])c3n(-c3ccccc3)c2c1[2H]]

HT-3
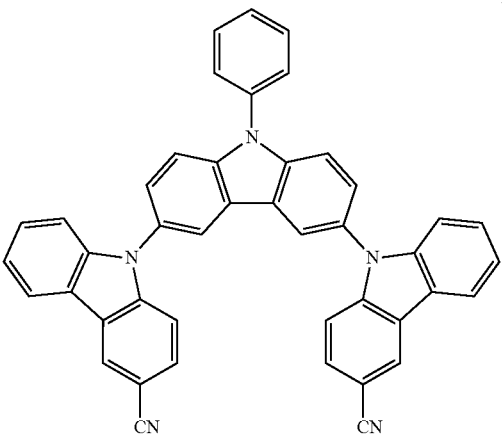

HT-4
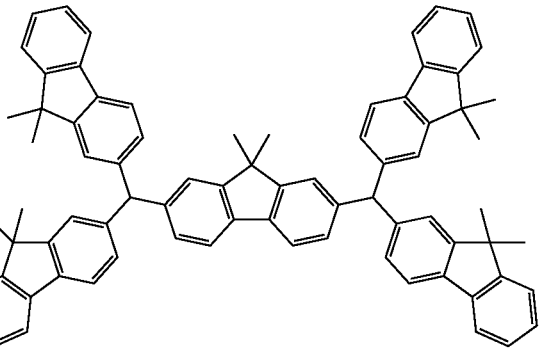

H-7
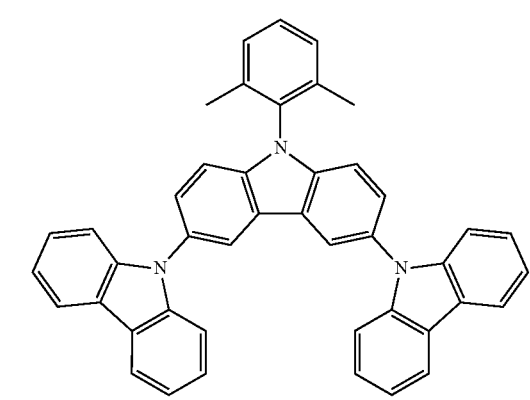

HT-1

All of ligands and complexes used in the Examples and Comparative Examples were synthesized by reference to the method disclosed in US-A-2008/297033, page 55, paragraph 129, et seq. A ligand of Compound 20 was synthesized using the synthesis method disclosed in JP-A-2009-102533, page 189, paragraphs 288 to 302. Also, Compound 8 was synthesized in the method disclosed in WO 02/15645, page 33, except for changing the picolinic acid to a corresponding picolinic acid analogue. Each of Compounds 7 and 22 was synthesized in the method disclosed in WO 2008/140114, page 169, except for changing the acetylacetone to a corresponding diketone.

A molecular weight and a fluorine atom content (% by mass) of each of iridium complexes used in the Examples and Comparative Examples are shown in the following Table 1.

TABLE 1

| Compound | Molecular weight | rate F |
|---|---|---|
| 1 | 1180.18 | 9.7% |
| 2 | 951.88 | 12.0% |
| 3 | 1540.09 | 33.3% |
| 4 | 1047.94 | 16.3% |
| 5 | 951.88 | 12.0% |
| 6 | 1047.94 | 16.3% |
| 7 | 833.75 | 13.7% |
| 8 | 884.8 | 12.9% |
| 9 | 951.88 | 12.0% |
| 10 | 1342.09 | 21.2% |
| 11 | 1132.09 | 15.1% |
| 12 | 1336.09 | 25.6% |
| 13 | 1005.85 | 17.0% |
| 14 | 1059.82 | 21.5% |
| 15 | 1114.03 | 25.6% |
| 16 | 1275.73 | 35.7% |
| 17 | 1546.09 | 29.5% |
| 18 | 1486.12 | 30.7% |
| 19 | 1408.66 | 8.1% |
| 20 | 996.94 | 11.4% |
| 21 | 690.74 | 11.5% |
| ref-1 | 897.91 | 6.3% |
| ref-2 | 1251.94 | 27.3% |
| ref-3 | 1186.42 | 4.8% |
| ref-4 | 886.03 | 0.0% |
| ref-5 | 1047.94 | 16.3% |
| ref-6 | 761.79 | 5.0% |

Example 1

An indium tin oxide (ITO) film-provided glass substrate having a thickness of 100 μm and a size of 2.5 cm in square (manufactured by Geomatec Co., Ltd., surface resistance: 10Ω/□) was put in a washing vessel, ultrasonically washed in 2-propanol and then subjected to a UV-ozone treatment for 30 minutes. The following organic layers were successively vapor deposited on this transparent anode (ITO film) by means of vacuum vapor deposition.

First layer: CuPc (copper phthalocyanine), film thickness: 120 nm

Second layer: NPD (N,N'-di-α-naphthyl-N,N'-diphenyl)-benzidine), film thickness: 7 nm Third layer: CBP (4,4'-di(9-carbazoyl)biphenyl), film thickness: 3 nm Fourth layer (light emitting layer): Dopant (9% by mass), host material (91% by mass), film thickness: 30 nm Fifth layer: First electron transport material (BAlq), film thickness: 30 nm 1 nm-thick lithium fluoride and 100 nm-thick metallic aluminum were vapor deposited in this order thereon, thereby forming a cathode.

The obtained laminate was placed in a nitrogen gas-purged glove box without being exposed to the air and sealed using a stainless steel-made sealing can and a ultraviolet ray-curable adhesive (XNR5516HV, manufactured by Nagase-CHIBA Ltd.), thereby obtaining Device 1 which is concerned with a working example of the invention.

Devices 2 to 12 which are concerned with a working example of the invention and Comparative Devices 1 to 5 which are concerned with a comparative example were prepared in the same manner as in the foregoing Device 1, except for changing constituent materials of the device as shown in the following Table 2.

(Performance Evaluation of Organic Electroluminescence Device)

The performance of each of the obtained devices was evaluated.

Figure 4:
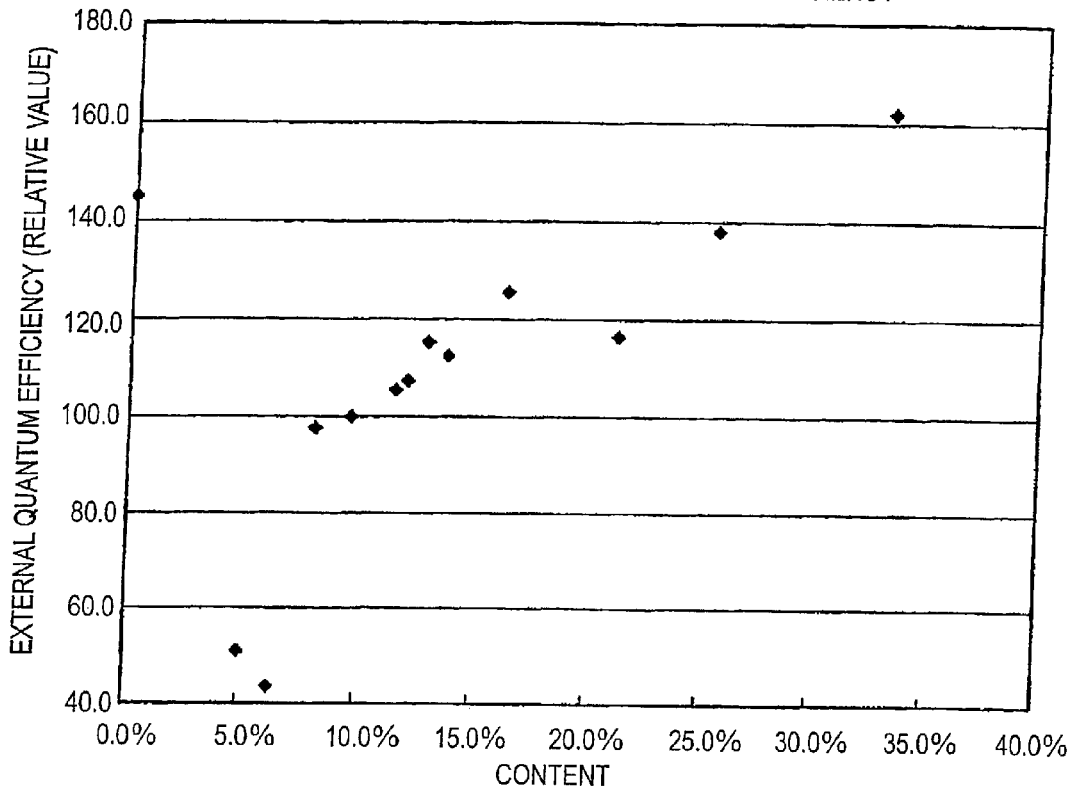
FIG. 4 is a graph plotting a relation between a fluorine atom content and an external quantum efficiency of each compound in Example 1.

(a) External Quantum Efficiency:

Each of the devices was subjected to light emission upon being impressed with a direct current voltage using a source measure unit MODEL 2400, manufactured by Toyo Corporation. Its brightness was measured using a brightness meter BM-8, manufactured by Topcon Corporation. An emission spectrum and a light emission wavelength were measured using a spectral analyzer PMA-11, manufactured by Hamamatsu Photonics K.K. An external quantum efficiency at a brightness in the vicinity of 1,000 cd/m$^2$ was calculated based on the thus measured values according to the brightness conversion method. For the purpose of clarification, the external quantum efficiency was expressed as a relative value while defining a value of Device 1 which is concerned with a working example of the invention as 100. Also, a graph plotting a relation between a fluorine atom content and an external quantum efficiency is shown in FIG. 4.

(b) Driving Durability:

Each of the devices was continuously subjected to light emission upon being impressed with a direct current voltage such that the brightness was 1,000 cd/m$^2$. A time required until the brightness reached 800 cd/m$^2$ was defined as an index for the driving durability and expressed as a relative value while defining a value of Device 1 which is concerned with a working example of the invention as 1.

(c) Chromaticity Change:

A chromaticity change was calculated from CIEx and CIEy values determined from an emission spectrum measured at 20° C. (using an emission spectrum measuring system (ELS-1500), manufactured by Shimadzu Corporation).

TABLE 2

| | Light emitting material | Host material | CIE Chromaticity x | CIE Chromaticity y | External quantum efficiency (Relative value) | Durability (Relative value) |
|---|---|---|---|---|---|---|
| Device 1 of the invention | 1 | H-1 | 0.14 | 0.22 | 100.0 | 1 |
| Device 2 of the invention | 3 | H-1 | 0.13 | 0.2 | 161.8 | 1 |
| Device 3 of the invention | 5 | H-1 | 0.13 | 0.2 | 107.3 | 1.2 |
| Device 4 of the invention | 6 | H-1 | 0.14 | 0.19 | 125.5 | 1.1 |
| Device 5 of the invention | 7 | H-1 | 0.13 | 0.19 | 112.7 | 0.95 |
| Device 6 of the invention | 8 | H-1 | 0.14 | 0.22 | 94.6 | 0.97 |
| Device 7 of the invention | 9 | H-1 | 0.16 | 0.28 | 101.8 | 1.2 |
| Device 8 of the invention | 10 | H-1 | 0.14 | 0.18 | 116.4 | 0.9 |
| Device 9 of the invention | 15 | H-1 | 0.14 | 0.17 | 138.0 | 0.91 |
| Device 10 of the invention | 19 | H-1 | 0.13 | 0.17 | 97.8 | 0.85 |
| Device 11 of the invention | 1 | H-2 | 0.14 | 0.22 | 101.8 | 1.1 |
| Device 12 of the invention | 3 | H-3 | 0.13 | 0.21 | 118.2 | 1.1 |
| Comparative Device 1 | ref-1 | H-1 | 0.14 | 0.24 | 43.6 | 0.9 |
| Comparative Device 2 | ref-2 | H-1 | — | — | <5.0 | 0.02 |
| Comparative Device 3 | ref-4 | H-1 | 0.16 | 0.22 | 145.2 | 0.12 |

TABLE 2-continued

|  | Light emitting material | Host material | CIE Chromaticity x | CIE Chromaticity y | External quantum efficiency (Relative value) | Durability (Relative value) |
|---|---|---|---|---|---|---|
| Comparative Device 4 | ref-5 | H-1 | — | — | <5.0 | 0.05 |
| Comparative Device 5 | ref-6 | H-1 | 0.2 | 0.25 | 51.1 | 0.35 |

From the results shown in Table 2, it is noted that Devices 1 to 12 of the invention are excellent in the blue hue and high in the external quantum efficiency and do not lower the durability. Comparative Device 1 is a device using Material ref-1 disclosed in US-A-2008/297033 and is low in the luminous efficiency as compared with the devices of the invention. Also, though the device using Material ref-4 disclosed in the same patent document is enhanced in the efficiency, it is largely lowered in the device durability. Though Material ref-2 or ref-5 disclosed in JP-A-2008-311607 has a substituent adjacent to the metal-coordinating atom, the devices using such a material did not substantially display the light emission. It may be supposed that this was caused due to the fact that the coordination bond to the metal is expanded due to the substituent and becomes instable, whereby the deactivation process becomes a main route.

Example 2

Figure 5:
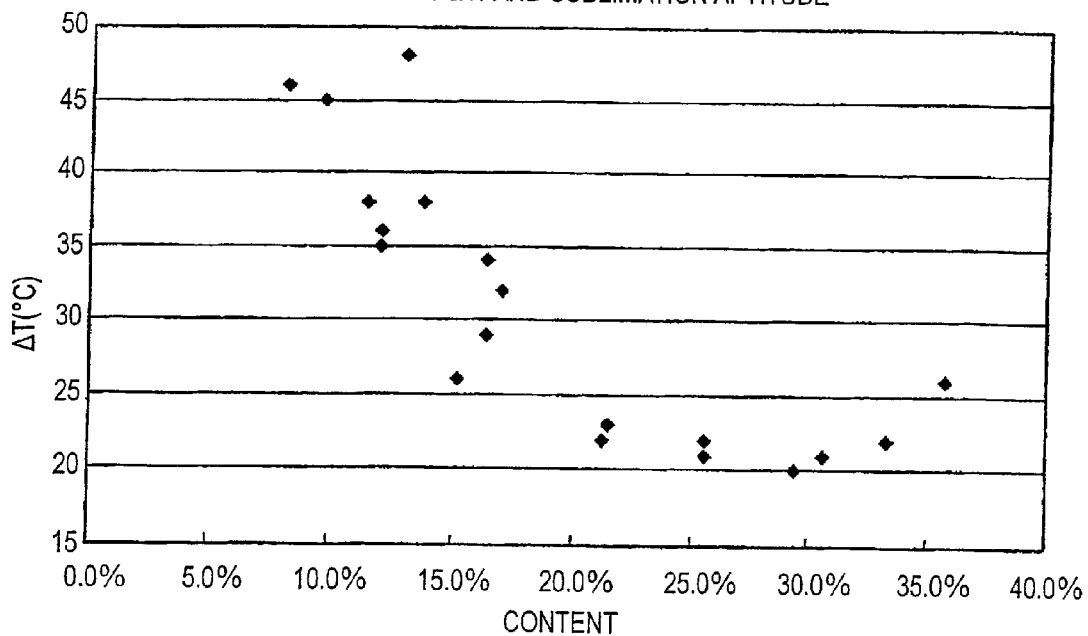
FIG. 5 is a graph plotting a relation between a fluorine atom content and a sublimation aptitude (ΔT) of each compound in Example 2, wherein 2 denotes Substrate, 3 denotes Anode, 4 denotes Hole injection layer, 5 denotes Hole transport layer, 6 denotes Light emitting layer, 7 denotes Hole blocking layer, 8 denotes Electron transport layer, 9 denotes Cathode, 10 denotes Organic electroluminescence device (organic EL device), 11 denotes Organic layer, 12 denotes Protective layer, 14 denotes Adhesive layer, 16 denotes Sealing vessel, 20 denotes Light emission unit, 30 denotes Light scattering member, 30A denotes Light incident surface, 30B denotes Light outgoing surface, 32 denotes Fine particle, and 40 denotes Illumination unit.

With respect to each of the compounds of the invention and the comparative compounds, a TG curve at $1 \times 10^{-2}$ Pa was measured in a sample amount of 20 mg, and a temperature (T(−5%)) at a [(weight loss percent)−5%] point (since all of purities of the samples are 97% or more in terms of an HPLC area ratio, the −5% point was regarded as a temperature at which sublimation and evaporation were started) and a temperature (T(end)) at a point where the weight loss was completed were measured. In this respect, all of the measurements are carried out while elevating the temperature at a rate of 1° C. per minute. Also, sublimation purification was carried out at the temperature T(end) in a starting weight of 500 mg under the same pressure, and a purification yield thereof was evaluated. Also, a graph plotting a relation between a fluorine atom content and a sublimation aptitude ($\Delta T$) is shown in FIG. 5.

Next, a device having the following constitution was prepared using the obtained material.

First layer: CuPc (copper phthalocyanine), film thickness: 120 nm

Second layer: NPD (N,N'-di-α-naphthyl-N,N'-diphenyl)-benzidine), film thickness: 7 nm Third layer: CBP (4,4'-di(9-carbazoyl)biphenyl), film thickness: 3 nm Fourth layer (light emitting layer): Dopant (9% by mass), H-1 (91% by mass), film thickness: 30 nm Fifth layer: First electron transport material (BAlq), film thickness: 30 nm 1 nm-thick lithium fluoride and 100 nm-thick metallic aluminum were vapor deposited in this order thereon, thereby forming a cathode. The obtained laminate was placed in a nitrogen gas-purged glove box without being exposed to the air and sealed using a stainless steel-made sealing can and a ultraviolet ray-curable adhesive (XNR5516HV, manufactured by Nagase-CHIBA Ltd.), thereby obtaining Device 2-1 which is concerned with a working example of the invention.

Each of the devices obtained by the foregoing method was impressed with a direct current voltage such that the brightness was 1,000 cd/m², and a driving voltage V1 was measured. Thereafter, the light emission was continued at a constant current density until the brightness reached 500 cd/m², and at that time, a driving voltage V2 was measured. A ratio V2/V1 between these two driving voltages was defined as an index showing voltage maintenance when the device was deteriorated.

TABLE 3

|  | Material | T (−5%) (° C.) | T (end) (° C.) | ΔT (° C.) | Purification yield (%) | V2/V1 |
|---|---|---|---|---|---|---|
| Material 2-1 of the invention | 1 | 335 | 380 | 45 | 42 | 1.11 |
| Material 2-2 of the invention | 2 | 301 | 336 | 35 | 54 | 1.01 |
| Material 2-3 of the invention | 3 | 298 | 320 | 22 | 90 | 1.03 |
| Material 2-4 of the invention | 4 | 330 | 364 | 34 | 56 | 1.04 |
| Material 2-5 of the invention | 5 | 305 | 341 | 36 | 55 | 1.06 |
| Material 2-6 of the invention | 6 | 328 | 357 | 29 | 66 | 1.09 |
| Material 2-7 of the invention | 7 | 302 | 340 | 38 | 49 | 1.06 |
| Material 2-8 of the invention | 8 | 301 | 349 | 48 | 40 | 1.04 |
| Material 2-9 of the invention | 9 | 325 | 361 | 36 | 50 | 1.06 |
| Material 2-10 of the invention | 10 | 360 | 382 | 22 | 86 | 1.08 |
| Material 2-11 of the invention | 11 | 336 | 362 | 26 | 78 | 1.08 |
| Material 2-12 of the invention | 12 | 356 | 377 | 21 | 90 | 1.01 |
| Material 2-13 of the invention | 13 | 325 | 357 | 32 | 59 | 1.06 |
| Material 2-14 of the invention | 14 | 320 | 343 | 23 | 83 | 1.03 |
| Material 2-15 of the invention | 15 | 294 | 316 | 22 | 86 | 1.00 |
| Material 2-16 of the invention | 16 | 291 | 317 | 26 | 73 | 1.14 |
| Material 2-17 of the invention | 17 | 326 | 346 | 20 | 91 | 1.02 |
| Material 2-18 of the invention | 18 | 340 | 361 | 21 | 90 | 1.03 |
| Material 2-19 of the invention | 19 | 331 | 377 | 46 | 41 | 1.10 |
| Material 2-20 of the invention | 20 | 299 | 337 | 38 | 50 | 1.14 |
| Comparative Example 2-1 | ref-1 | 332 | 415 | 83 | 23 | 1.35 |
| Comparative Example 2-2 | ref-2 | 305 | 401 | 96 | 6 | 1.6 |
| Comparative Example 2-3 | ref-3 | 309 | 410 | 101 | 19 | 1.46 |

TABLE 3-continued

| | Material | T (−5%) (° C.) | T (end) (° C.) | ΔT (° C.) | Purification yield (%) | V2/V1 |
|---|---|---|---|---|---|---|
| Comparative Example 2-4 | ref-4 | 340 | 420 | 80 | 24 | 1.31 |
| Comparative Example 2-5 | ref-5 | 314 | 413 | 99 | 8 | 1.82 |

Metal Complexes 1 to 20 which are concerned with a working example of the invention are small in ΔT as compared with Metal Complexes ref-1 to ref-5 which are concerned with a comparative example, and following this, the purification yield is large. With respect to Compounds ref-2 and ref-5, it is confirmed that a tar-like material which is seemed to be a thermal decomposition product is obtained in a residue, and it is noted that the yield of sublimation purification is also extremely low due to instability of the compound itself. Also, in comparing the devices prepared using the obtained complex, even the devices having been deteriorated through continuous driving can be driven at a substantially equal voltage according to the working example of the invention. It may be estimated that this was caused due to the fact that a composition in which a decomposition product which will be a cause of voltage elevation during the deterioration is hardly induced is formed through sublimation purification.

In the case of a light emitting unit, a display unit or an illumination unit, it may be assumed that the device is driven over a long period of time. On that occasion, when the voltage is largely increased due to deterioration of the device, a consumed power amount increases; and in the case of a white device, there is a possibility that color drift is caused due to the fact that a difference in driving voltage from a device of other color becomes large. Since the luminescence device of the invention has such a characteristic that even when driven over a long period of time, the voltage hardly increases, the luminescence device of the invention can be advantageously utilized at this point.

Example 3

An indium tin oxide (ITO) film-provided glass substrate having a thickness of 100 μm and a size of 2.5 cm in square (manufactured by Geomatec Co., Ltd., surface resistance: 10Ω/□) was put in a washing vessel, ultrasonically washed in 2-propanol and then subjected to a UV-ozone treatment for 30 minutes. The following organic layers were successively vapor deposited on this transparent anode (ITO film) by means of vacuum vapor deposition.

First layer: CuPc (copper phthalocyanine), film thickness: 120 nm

Second layer: NPD (N,N'-di-α-naphthyl-N,N'-diphenyl)-benzidine), film thickness: 7 nm Third layer: Charge transport material, film thickness: 2 nm Fourth layer (light emitting layer): Dopant (12% by mass), host material (88% by mass), film thickness: 30 nm Fifth layer: First electron transport material (BAlq), film thickness: 30 nm 1 nm-thick lithium fluoride and 100 nm-thick metallic aluminum were vapor deposited in this order thereon, thereby forming a cathode.

The obtained laminate was placed in a nitrogen gas-purged glove box without being exposed to the air and sealed using a stainless steel-made sealing can and a ultraviolet ray-curable adhesive (XNR5516HV, manufactured by Nagase-CHIBA Ltd.). There were thus obtained Devices 3-1 to 3-15 which are concerned with a working example of the invention.

(Performance Evaluation of Organic Electroluminescence Device)

An external quantum efficiency as the performance of each of the obtained devices was evaluated in the same manner as in Example 1. For the purpose of clarification, the external quantum efficiency was expressed as a relative value while defining a value of Device 3-1 which is concerned with a working example of the invention as 100.

TABLE 4

| | Charge transport material | Light emitting material | Host material | External quantum efficiency (Relative value) |
|---|---|---|---|---|
| Device 3-1 of the invention | CBP | 1 | H-1 | 100.0 |
| Device 3-2 of the invention | CBP | 1 | H-2 | 101.0 |
| Device 3-3 of the invention | CBP | 1 | H-3 | 95.0 |
| Device 3-4 of the invention | CBP | 1 | H-4 | 105.0 |
| Device 3-5 of the invention | CBP | 1 | H-5 | 106.4 |
| Device 3-6 of the invention | CBP | 1 | H-6 | 101.2 |
| Device 3-7 of the invention | CBP | 1 | H-7 | 100.8 |
| Device 3-8 of the invention | CBP | 2 | H-3 | 91.0 |
| Device 3-9 of the invention | CBP | 2 | H-6 | 103.0 |
| Device 3-10 of the invention | CBP | 2 | H-7 | 104.0 |
| Device 3-11 of the invention | CBP | 13 | H-2 | 135.4 |
| Device 3-12 of the invention | HT-1 | 13 | H-2 | 154.6 |
| Device 3-13 of the invention | HT-2 | 13 | H-2 | 151.9 |
| Device 3-14 of the invention | HT-3 | 13 | H-2 | 149.5 |
| Device 3-15 of the invention | HT-4 | 13 | H-2 | 101.2 |

In the working example of the invention, though even when the host material is properly changed, a high efficiency is obtainable, in particular, by using the compound represented by the formula (4-1) or (4-2) in the light emitting layer, a higher efficiency can be obtained. Also, when each of Compounds HT-1 to HT-3 represented by the formula (a) is used as the charge transport material, the charge transporting properties into the light emitting layer are enhanced, and the efficiency is further enhanced due to an increase of a probability of recombination in the inside of the light emitting layer.

INDUSTRIAL APPLICABILITY

According to the invention, an organic electroluminescence device displaying excellent luminous efficiency and durability and having a favorable hue can be provided. Also, a material for organic electroluminescence device which is excellent in productivity can be provided.

This application is based on Japanese patent application No. 2009-201146 filed on Aug. 31, 2009, the entire content of which is hereby incorporated by reference, the same as if set forth at length.

The invention claimed is:

1. A material for an organic electroluminescence device, comprising:
a phosphorescent metal complex represented by the following formula (A10):

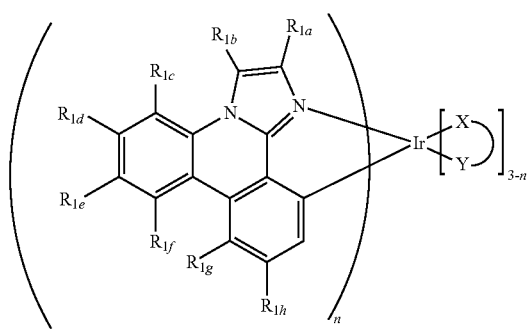

(A10)

in formula (A10),
each of $R_{1a}$ to $R_{1h}$ independently represents
a hydrogen atom,
a fluorine atom,
a methyl group, an ethyl group, an isopropyl group, an n-butyl group, an isobutyl group, a neopentyl group, an n-hexyl group,
a phenyl group or a naphthyl group, each of which may be substituted with a methyl group, an isopropyl group or a neopentyl group,
a methyl group, an ethyl group, an isopropyl group, an n-butyl group, an isobutyl group, a neopentyl group or an n-hexyl group, each of which is substituted with 1 or more and not more than 10 fluorine atoms, or
a phenyl group or a naphthyl group, each of which may be substituted with a methyl group, an isopropyl group or a neopentyl group, each of which is substituted with 1 or more and not more than 10 fluorine atoms;
$R_{1a}$ to $R_{1h}$ may be bonded to each other to form a ring;
X-Y represents a monoanionic bidentate ligand represented by the following I-1, I-4 or I-5; and
n represents 2 or 3:

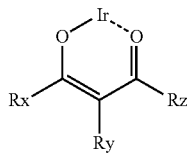

I-1

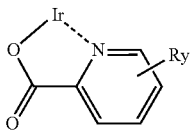

I-4

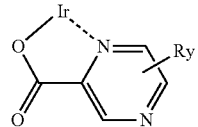

I-5 wherein
each of Rx, Ry and Rz independently represents a hydrogen atom, a fluorine atom, an alkyl group having not more than 6 carbon atoms, a phenyl group, an alkyl group having not more than 6 carbon atoms and substituted with one or more fluorine atoms, or a phenyl group substituted with one or more fluorine atoms,
provided that a content of a fluorine atom in the phosphorescent metal complex is 7% by mass or more.

2. The material for an organic electroluminescence device according to claim 1,
wherein the phosphorescent metal complex represented by the formula (A10) is a phosphorescent metal complex represented by the following formula (A10-1):

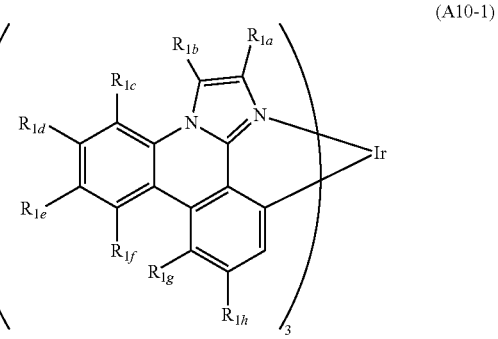

(A10-1)

in formula (A10-1),
$R_{1a}$ to $R_{1h}$ are synonymous with $R_{1a}$ to $R_{1h}$ in the formula (A10).

3. The material for an organic electroluminescence device according to claim 1,
wherein the phosphorescent metal complex represented by the formula (A10) is a phosphorescent metal complex represented by the following formula (A20):

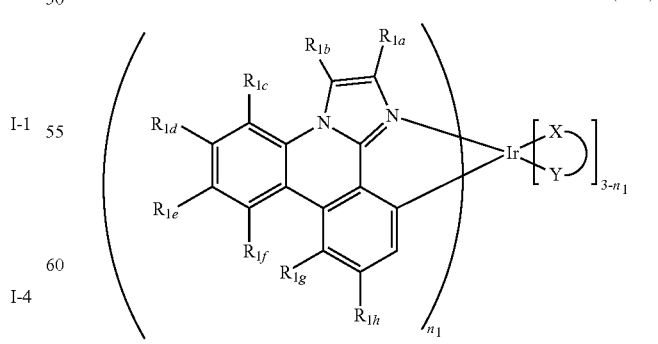

(A20)

in formula (A20),
each of $R_{1a}$ to $R_{1c}$ independently represents
a hydrogen atom, a methyl group, an ethyl group, an isopropyl group, an n-butyl group, an isobutyl group, a neopentyl group, an n-hexyl group, or a phenyl group or a naphthyl group, each of which may be substituted with a methyl group, an isopropyl group or a neopentyl group;

$R_{1a}$ to $R_{1h}$ may be bonded to each other to form a ring;

$n_1$ represents 2; and

X-Y, Rx, Ry and Rz are synonymous with X-Y, Rx, Ry and Rz in the formula (A10).

4. An organic electroluminescence device, comprising:

a substrate having thereon a pair of electrodes; and at least one layer of organic layers including a light emitting layer between the electrodes, wherein the material for an organic electroluminescence device according to claim 1 is contained in at least one layer of the organic layers.

5. The organic electroluminescence device according to claim 4, wherein the material for an organic electroluminescence device is contained in the light emitting layer.

6. A light emitting unit that uses the organic electroluminescence device according to claim 4.

7. A display unit that uses the organic electroluminescence device according to claim 4.

8. An illumination unit that uses the organic electroluminescence device according to claim 4.

* * * * *